United States Patent [19]

Mills

[11] Patent Number: 5,221,518
[45] Date of Patent: Jun. 22, 1993

[54] DNA SEQUENCING APPARATUS

[76] Inventor: Randell L. Mills, R.D. #2, Cochranville, Pa. 19330

[21] Appl. No.: 744,697

[22] Filed: Aug. 13, 1991

Related U.S. Application Data

[60] Division of Ser. No. 120,339, Nov. 13, 1987, Pat. No. 5,064,754, which is a continuation-in-part of Ser. No. 681,842, Dec. 14, 1984, abandoned.

[51] Int. Cl.$^5$ .................. C12P 19/34; G01N 33/00
[52] U.S. Cl. ........................ 422/62; 422/67; 422/82.05; 435/291; 436/89
[58] Field of Search .............. 422/62, 67, 82.05; 436/89, 94, 161, 173; 435/6, 291

[56] References Cited

U.S. PATENT DOCUMENTS

| | | | |
|---|---|---|---|
| 4,720,483 | 1/1988 | Jansz et al. | 514/11 |
| 4,863,849 | 9/1989 | Melamede | 435/6 |
| 4,942,124 | 7/1990 | Church | 435/6 |
| 5,006,465 | 4/1991 | Anderson et al. | 435/69.52 |
| 5,104,621 | 4/1992 | Pfost et al. | 422/67 |
| 5,106,585 | 4/1992 | Minami et al. | 422/68.1 |

Primary Examiner—James C. Housel
Assistant Examiner—David Redding
Attorney, Agent, or Firm—Lahive & Cockfield

[57] ABSTRACT

The DNA sequencing apparatus contains the following components. A first reaction vessel contains a reaction chamber into and out of which can be transferred reagents, reactants and reaction products. A device for separating individual oligonucleotides and polynucleotides on the basis of length, such as an electrophoretic unit, receives reaction products from the first reaction vessel. A second reaction vessel is designed for oxidizing pentose sugars. It comprises a reaction chamber having a device for transferring reactants and reagents into the reaction chamber and gaseous by-products of a reaction out of the reaction chamber. Separated oligonucleotides and polynucleotides can be selectably transferred from the separating device alternatively into the first or the second reaction vessel. The device also includes a second transfer device for transferring the gaseous by-products out of the second reaction vessel and a collection chamber for collecting the gaseous by-products. The collection chamber is in communication with the second transfer device. Finally, the apparatus contains an analyzer for analyzing the relative abundance of the components of the gaseous by-product by mass such as a mass spectrometer, the analyzer being in communication with a transfer device for transferring gaseous by-products from the collection chamber to the analyzer.

13 Claims, 13 Drawing Sheets

FIG. 4

```
         XI X2 X3 X4 X5 X6 X7 X8 X9 XIO XII
GACTACGA TG C  C  T  A  G  T  G  C   T
```

| | | | | |
|---|---|---|---|---|
| | | | GACTACGAXI-X8 | GACTACGAXI-X7 |
| | | ACTACGAXI-X9 | ACTACGAXI-X8 | ACTACGAXI-X7 |
| | CTACGAXI-XIO | CTACGAXI-X9 | CTACGAXI-X8 | CTACGAXI-X7 |
| TACGAXI-XII | TACGAXI-XIO | TACGAXI-X9 | TACGAXI-X8 | TACGAXI-X7 |
| ACGAXI-XII | ACGAXI-XIO | ACGAXI-X9 | ACGAXI-X8 | ACGAXI-X7 |
| CGAXI-XII | CGAXI-XIO | CGAXI-X9 | CGAXI-X8 | CGAXI-X7 |
| GAXI-XII | GAXI-XIO | GAXI-X9 | GAXI-X8 | GAXI-X7 |
| AXI-XII | AXI-XIO | AXI-X9 | AXI-X8 | AXI X7 |
| XI-XII | XI-XIO | XI-X9 | XI-X8 | XI X7 |

FIG. 4 CONT.

```
            X1 X2 X3 X4 X5 X6 X7 X8 X9 X10 X11
GACTACGA     T  G  C  C  T  A  G  T  G  C   T
```

| | | | | | |
|---|---|---|---|---|---|
| GACTACGAX1-X6 | GACTACGAX1-X5 | GACTACGAX1-X4 | GACTACGAX1-X3 | GACTACGAX1-X2 | GACTACGAX1 |
| ACTACGAX1-X6 | ACTACGAX1-X5 | ACTACGAX1-X4 | ACTACGAX1-X3 | ACTACGAX1-X2 | ACTACGAX1 |
| CTACGAX1-X6 | CTACGAX1-X5 | CTACGAX1-X4 | CTACGAX1-X3 | CTACGAX1-X2 | CTACGAX1 |
| TACGAX1-X6 | TACGAX1-X5 | TACGAX1-X4 | TACGAX1-X3 | TACGAX1-X2 | TACGAX1 |
| ACGAX1-X6 | ACGAX1-X5 | ACGAX1-X4 | ACGAX1-X3 | ACGAX1-X2 | ACGAX1 |
| CGAX1-X6 | CGAX1-X5 | CGAX1-X4 | CGAX1-X3 | CGAX1-X2 | CGAX1 |
| GAX1-X6 | GAX1-X5 | GAX1-X4 | GAX1-X3 | GAX1-X2 | GAX1 |
| AX1-X6 | AX1-X5 | AX1-X4 | AX1-X3 | AX1-X2 | AX1 |
| X1-X6 | X1-X5 | X1-X4 | X1-X3 | X1-X2 | X1 |

FIG. 5 CONT.

| POLYNUCLEOTIDE (RNA UNDERLINED) | COMPOSITION | Δ | TERMINAL |
|---|---|---|---|
| 1 <u>GAC</u>TACGATGCCTAGTGCT | 4A 5G 5T 5C |  | T |
| 2 <u>GAC</u>TACGATGCCTAGTGC | 4A 5G 4T 5C | T | C |
| 3 <u>GAC</u>TACGATGCCTAGTG | 4A 5G 4T 4C | C | G |
| 4 <u>GAC</u>TACGATGCCTAGT | 4A 4G 4T 4C | G | T |
| 5 <u>GAC</u>TACGATGCCTAG | 4A 4G 3T 4C | T | G |
| 6 <u>GAC</u>TACGATGCCTA | 4A 3G 3T 4C | G | A |
| 7 <u>GAC</u>TACGATGCCT | 3A 3G 3T 4C | A | T |
| 8 <u>GAC</u>TACGATGCC | 3A 3G 2T 4C | T | C |
| 9 <u>GAC</u>TACGATGC | 3A 3G 2T 3C | C | C |
| 10 <u>GAC</u>TACGATG | 3A 3G 2T 2C | C | G |
| 11 <u>GAC</u>TACGAT | 3A 2G 2T 2C | G | T |
| 12 <u>GAC</u>TACGA | 3A 2G 1T 2C | T | A |
| 13 <u>GAC</u>TACG | 2A 2G 1T 2C | A | G |
| 14 <u>GAC</u>TAC | 2A 1G 1T 2C | G | C |
| 15 <u>GAC</u>TA | 2A 1G 1T 1C | C | A |
| 16 <u>TACGAT</u>GCCTAGTGCT | 3A 4G 5T 4C |  | T |
| 17 <u>TACGAT</u>GCCTAGTGC | 3A 4G 4T 4C | T | C |
| 18 <u>TACGAT</u>GCCTAGTG | 3A 4G 4T 3C | C | G |
| 19 <u>TACGAT</u>GCCTAGT | 3A 3G 4T 3C | G | T |
| 20 <u>TACGAT</u>GCCTAG | 3A 3G 3T 3C | T | G |
| 21 <u>TACGAT</u>GCCTA | 3A 2G 3T 3C | G | A |
| 22 <u>TACGAT</u>GCCT | 2A 2G 3T 3C | A | T |
| 23 <u>TACGAT</u>GCC | 2A 2G 2T 3C | T | C |
| 24 <u>TACGAT</u>GC | 2A 2G 2T 2C | C | C |
| 25 <u>TACGAT</u>G | 2A 2G 2T 1C | C | G |
| 26 <u>TACGAT</u> | 2A 1G 2T 1C | G | T |

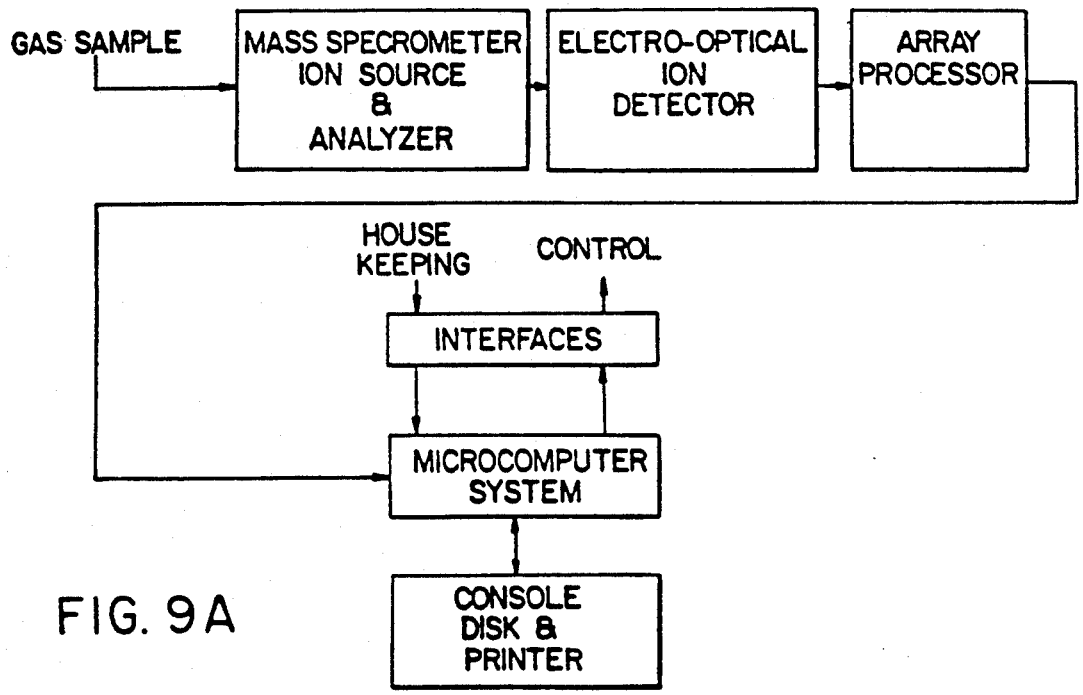
FIG. 9A
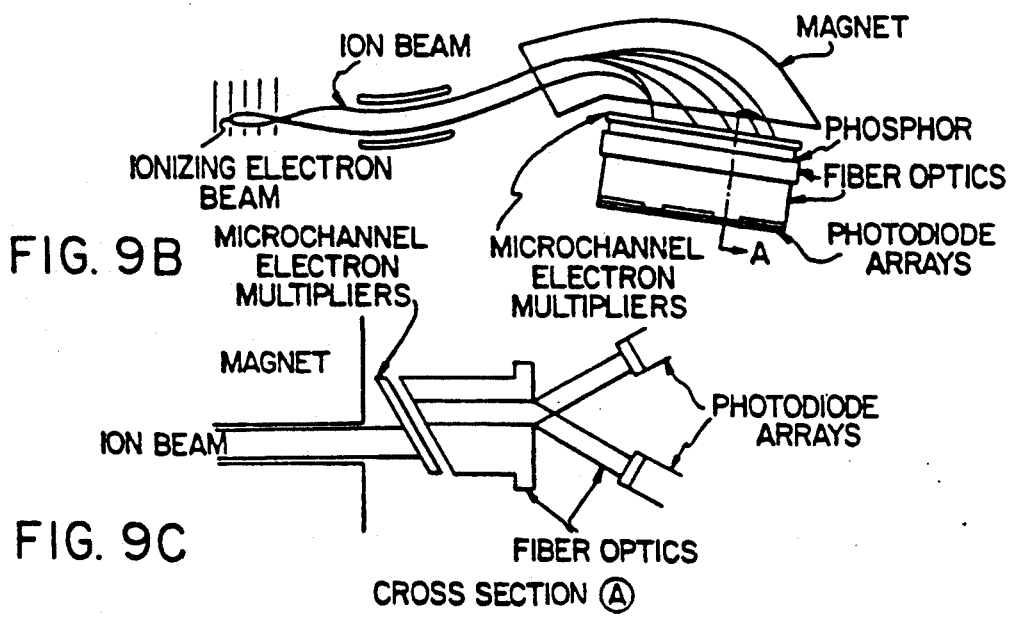
FIG. 9B
FIG. 9C
CROSS SECTION Ⓐ

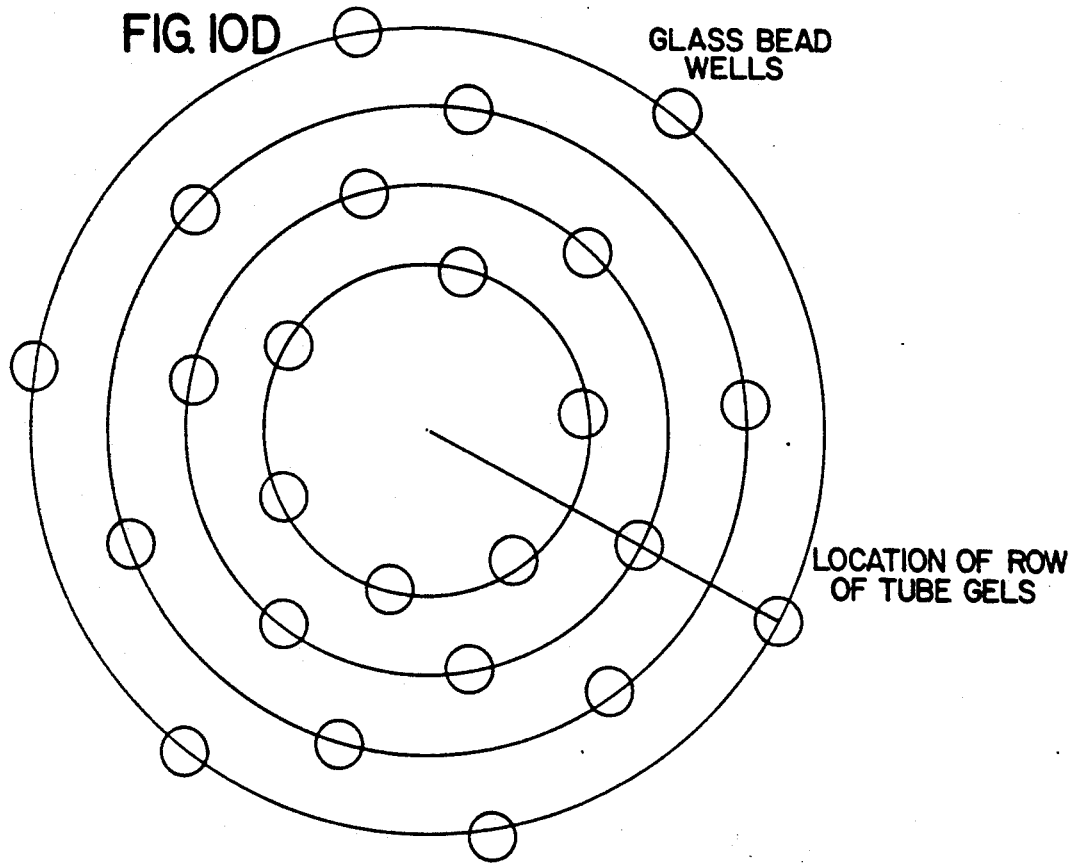
FIG. 10D — GLASS BEAD WELLS, LOCATION OF ROW OF TUBE GELS
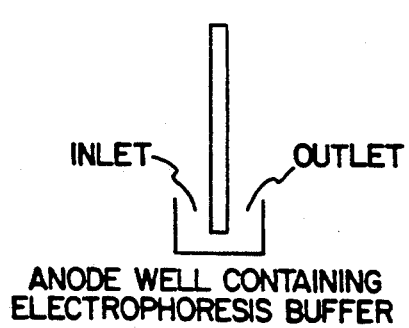
FIG. 10E — TUBE GEL, INLET, OUTLET, ANODE WELL CONTAINING ELECTROPHORESIS BUFFER

DNA SEQUENCING APPARATUS

CROSS REFERENCE TO RELATED APPLICATIONS

This is a divisional, of application Ser. No. 07/120,339, filed Nov. 13, 1987, now U.S. Pat. No. 5,064,754, which is a continuation-in-part of Ser. No. 06/681,842, filed Dec. 14, 1984, now abandoned.

BACKGROUND OF THIS INVENTION

Deoxyribonucleic acid (DNA) is the primary genetic material. DNA is an informational molecule which encodes all of the proteins which make up a living organism. This capacity it serves in all living organisms.

DNA consists of two intertwined polynucleotide chains, the double helix. Each chain is a polymer made up of nucleotides. The nucleotide constituents consist of a sugar, a phosphate and a nitrogenous heterocyclic base. Interchain pairing between the bases, via hydrogen bonding, holds the two chains together in the helical coil.

The nucleotides of DNA contain the sugar 2-deoxyribose and are designated deoxyribonucleotides. Nucleotides which contain the sugar D-ribose are called ribonucleotides: these are the building blocks of ribonucleic (RNA), the intermediary transcript of DNA which serves as the actual template for protein synthesis.

In all nucleotides the sugar moiety is attached to the nitrogenous base via the glycosidic carbon (1' carbon of the ribose). This combination of sugar and base is called a nucleoside. Phosphorylation of a nucleoside at the 5' carbon of the sugar gives a nucleotide. The backbone of the DNA polymer is formed of phosphodiester bonds between 2'-deoxynucleoside 5'-monophosphates. (3', 5'-phosphodiester bridges).

The nucleotides of DNA differ only in the nitrogenous base. There are two types of nitrogenous bases in nucleotides, pyrimidines and purines. The pyrimidines are uracil, thymine and cytosine (abbreviated U, T, and C respectively). Nucleotides containing uracil are found primarily in RNA whereas thymine is found in DNA. The major purines are adenine and guanine (abbreviated A and G respectively). In the DNA helix, complementary DNA chains are held together by base pairing. The sugar-phosphate backbones are on the outside of the DNA molecule and the purine and pyrimidine bases on the inside. Adenine (A) can pair only with thymine (T) while guanine (G) can pair only with cytosine.

The genetic information of DNA is stored in the linear sequence of the four nucleotides. Most nucleotides along a strand of DNA make up genes which code for specific polypeptides. The nucleotide sequence of DNA is read in groups of three nucleotides. Each triplet is a "code-word", or codon, for an amino acid. As there are 4 different nucleotides in DNA (distinguished by the bases A, T, G, and C) there are 64 different codons. These codons comprise the entire genetic code. Most of the codons designate an amino acid; some serve as start and stop signals for protein translation. The genetic code is degenerate because there is more than one codon for most of the amino acids. For example, the amino acid alanine is coded for by the codons CGA, CGG, CGT and CGC. (In RNA, the triplets are GCU, GCC, GCA and GCG.)

Several techniques have been developed for determining the nucleotide sequence of DNA. Among the more widely practiced are the methods of Maxam and Gilbert and of Sanger.

In the DNA sequencing technique of Maxam and Gilbert, a segment of DNA is labeled at one end with radiolabeled phosphate. The labeled DNA is divided into four samples and each sample is treated with a chemical that specifically destroys one or two of the four bases in the DNA. The "nicked" molecules are then treated with piperidine which breaks the DNA backbone at the site where the base has been destroyed. This generates a series of labeled fragments the lengths of which depend on the distance of the destroyed base from the labeled end of the segment. The labeled polynucleotides are separated according to size on an acrylamide gel. The gel is autoradiographed and the patterns of bands on the X-ray film determine which base was destroyed to produce each radioactive fragment. From this information the position of the destroyed bases can be determined and the overall sequence of the DNA deduced.

The DNA-sequencing technique of Sanger is an enzymatic procedure which entails the synthesis of radiolabeled DNA polynucleotides from the DNA strand to be sequenced. Chain-terminating dideoxynucleoside triphophates are used to stop synthesis at a particular nucleotide. A Sanger sequencing reaction includes a DNA strand to be sequenced, a labeled primer complementary to the end of that strand, a carefully controlled ratio of one particular dideoxynucleotide with its normal deoxynucleotide and the other 3 deoxynucleotides. When DNA polymerase is added, normal polymerization begins from the primer; when a dideoxynucleotide is incorporated, the chain is terminated. This results in a series of labeled polynucleotides whose lengths depend upon the location of a particular base relative to the end of the DNA strand.

Four separate polymerase reactions are conducted each containing one type of dideoxynucleotide. Radiolabeled fragments are separated by size on an acrylamide gel. The pattern of polynucleotides gives the DNA sequence.

The methods of Sanger and Maxam and Gilbert are convenient ways of sequencing single fragments of DNA of about 400 base pairs or less in length. To sequence large pieces of DNA, overlapping fragments of suitable length must be generated and sequenced individually. The overlapping sequence information among fragments provides the sequential relationship of the fragments so that their relative order can be assigned. From this information, the entire sequence of the parent piece of DNA can be pieced together.

With these approaches it is apparent that as the length of the DNA strand to be sequenced increases, the probability of obtaining fragments of a DNA strand which overlap sufficiently to eliminate the random occurrence of corresponding sequence decreases. Consequently, the number of randomly generated fragments of the strand necessary for accurate sequencing increases. For DNA strands even two orders of magnitude less than the length of a human chromosome the number of randomly generated fragments is immense. Thus, the technique is impractical for sequencing molecules of this size.

The Sanger technique of sequencing long strands of DNA requires DNA cloning procedures because DNA polymerization requires a primer. This is overcome by cloning the fragment into a vector so that it is contiguous with a region of known sequences so that the complementary primer may be provided. Because of this dependency on cloning technology, the procedure is difficult to automate.

DISCLOSURE OF THE INVENTION

This invention pertains to a method of sequencing DNA which entails the generation of a specific set of polynucleotides from the DNA to be sequenced, determining the nucleic acid base composition and terminal base of these molecules, and solving the base sequence of the molecules and thus, the sequence of the DNA, by an algorithm called the matrix method of analysis.

The molecules generated from the DNA to be sequenced comprise families of polynucleotides. Each family corresponds to a segment of the DNA to be sequenced and is made up of a longest polynucleotide (the length of which is selected to be within the analyzable limit of the procedure used to determine base composition and identity of the terminal base) and shorter polynucleotides which form a "sequential subset" of the longest polynucleotide. Grouped heirarchically from the longest to the shortest polynucleotide, each polynucleotide of the family is progressively one nucleotide shorter than the preceding polynucleotide and has the same sequence except that it lacks the one nucleotide. A further restraint on the elements of the family is that there is a specific dinucleotide of the sequence contained in each element. The molecules can be envisioned as being built around an "axis" which is at the mid position of the common dinucleotide. The "axis" constitutes an internal reference point. The polynucleotides vary around the "axis", each containing one less nucleotide on the 3' or 5' end than its longer predecessor in the group. All such molecules are included in the family, from the longest to the shortest, a dinucleotide.

In the preferred embodiment of the invention, the polynucleotides are RNA/DNA hybrid molecules generated from the DNA to be sequenced. To form these hybrids, DNA to be sequenced is broken into fragments and each fragment used as a template to form one or more RNA transcript(s). The RNA transcript(s) is then extended on the original intact DNA template with deoxyribonucleotides to form the DNA portion of the hybrid(s). The extension is terminated randomly by addition of dideoxynucleotides to the polymerase reaction. This yields RNA/DNA hybrid molecules which are "random" in length at the 3' end. The molecules can then be randomized at the 5' (RNA) end preferably by using an RNA exonuclease which under appropriate conditions, degrades the 5' RNA portion. The result of this procedure is a family of polynucleotides having the characteristic set forth above. The "axis" referred to above is the dividing line between the RNA and DNA and it immediately follows the 3' most ribonucleotide of all the hybrid molecules.

The sequence of the DNA portion from which each family of polynucleotides has been made can be solved by determining the base composition (the number of A's, T's, C's and G's) and the identity of the 3' terminal base of each polynucleotide of the family. A preferred method of analyzing polynucleotide to obtain this qualitative and quantitative data is mass spectroscopic analysis.

In the preferred embodiment the fifth position of the pentose of the nucleotides of the polynucleotide are mass labeled with isotopes of carbon, hydrogen, and oxygen in such a fashion that each possible nucleotide and terminal nucleotide releases a distinct mass labeled molecule (such as formaldehyde) from the fifth position of the pentose when the polynucleotide is degraded to 3' nucleotides or nucleosides and reacted with periodic acid. The relative abundance of the liberated molecules of different massess corresponding to different bases is recorded using a mass spectrometer. The intensities of the signals which correspond to the different bases are normalized with the signal corresponding to the terminal base which serves as the internal standard with a signal of unity. The base composition and internal base identity are given by the normalized data.

The composition and terminal nucleotide data of the elements of each family of polynucleotides are used to solve the sequence of the corresponding DNA portion template by a method of first generating all polynucleotides which can be obtained from a guessed solution of the sequence by successive removal of a 3' or 5' nucleotide consistent with the data of the change in composition between set elements and with the further constraint that a specific dinucleotide of the sequence must be present in all polynucleotides. The terminal nucleotide data is used to determine if a subset of the hypothetical family of polynucleotides exists such that the elements have a one to one correspondence with the data of terminal nucleotide as well as composition. If no such subset exists, the process is repeated for improved guesses until convergence to the correct solution for the sequence occurs.

An algorithm which performs this analysis by testing for the validity of a guess for part of the sequence while solving for the remaining part using the composition and terminal base data independently to execute binary hypothesis testing decisions compatible with computer logic is the matrix method of analysis algorithm.

The matrix method of analysis is analogous to solving a system of n equations in n unknowns where the knowns are: 1) the structural properties of the polynucleotides, 2) the base composition and the identity of the terminal base, 3) the change in composition and change in terminal base between a polynucleotide and the next in the family. Knowledge of the 5' half of the sequence may or may not be known. A different form of the matrix method is used depending on whether the sequence of the 5' half of the polynucleotides is known extrinsically. The method exploits the given information by implementing a reiterative procedure to find a path through a matrix of the possible polynucleotides having sequences consistent with the data. Final assignment of the sequence is made when the entire path finding procedure can be accomplished without contradictions between sequence assignment and actual data.

A major feature of the sequencing procedure of this invention is that it eliminates the obstacle of overlap among sequenced fragments of DNA occurring by chance. Because of the manner in which the polynucleotides are generated, each DNA fragment sequenced can be placed in proper order in relationship to all other fragments because a sufficient portion the 5' end of the flanking DNA fragment is elucidated as the sequence of any DNA fragment is determined. This permits the proper ordering of sequenced DNA fragments of a large DNA molecule to yield the entire sequence of DNA. Thus, an entire gene or even an entire chromosome can be sequenced from one set of restriction enzyme fragments of the gene or chromosome.

For sequencing fragments of DNA containing greater than 400 nucleotides, the methods of Maxam and Gilbert and Sanger rely on the chance overlap of restriction fragments which are isolated from a digest of the DNA to be sequenced. If small fragments are lost during the isolation procedure, then these molecules will not be sequenced; therefore, certain sequence information may be lost on account of the deletions. The strategy of the present invention, however, circumvents this shortcoming because the procedure to sequence any given restriction fragment solves for the sequence of the restriction fragment and sequences into the 5' region of the contiguous restriction fragment; any short fragments which are lost during isolation procedures are sequenced. Thus, no small deletions occur in the solution of the sequence by this method.

In addition, both strands of the template can be sequenced simultaneously; the sequence for any one strand can be verified by the sequence obtained for the antiparallel strand.

Another important attribute of the procedure is that it can be automated with instrumentation. Separation procedures can be automated with instruments such as automated electrophoresis and fraction collectors. A mass spectrometer with a response time of 10 msecs can scan 100 molecules in a second and NMR equipment which can be used to scan NMR labeled molecules has the capacity to scan 80,000 samples in less than one second. The sequence can be solved from the data obtained by using the matrix method of analysis programmed into a high speed computer. Thus, this method constitutes a procedure which is automatable to sequence DNA rapidly on a large scale.

BRIEF DESCRIPTION OF THE DRAWINGS

FIG. 4 is an example of a configuration matrix used to solve a sequence by the Matrix Method of Analysis I.

FIGS. 9A, 9B and 9C are diagrams of the electro-optical ion detector array mass spectrometer.

FIG. 10D is a diagram of the concentric disks containing wells of activated glass beads which rotate independently to collect electrophoresed nucleic acid.

FIG. 10E is a diagram of a single unit of the electrophoresis apparatus where DNA is collected from the units through outlets.

PRINCIPLES BEHIND STRATEGY OF THE METHOD OF THE INVENTION

I. Background

Figure 1:
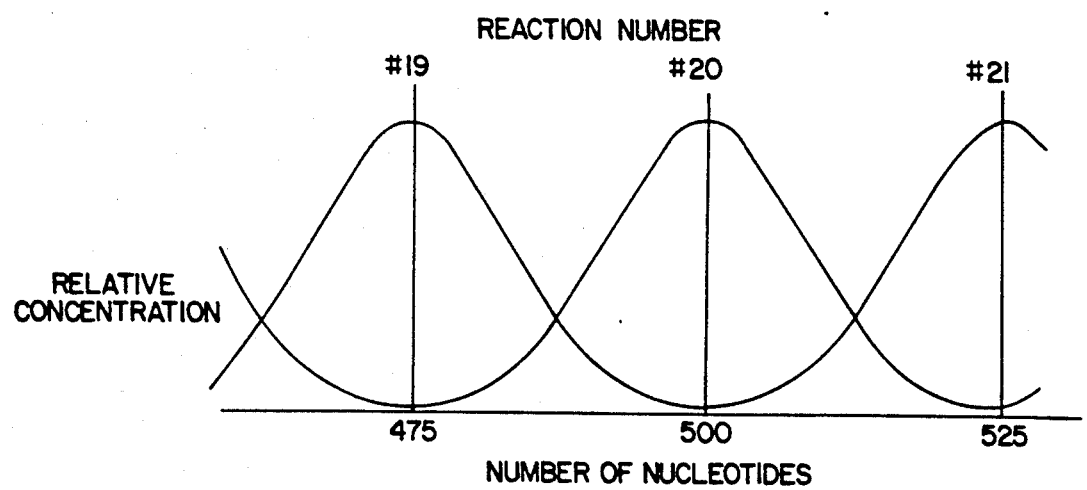
FIG. 1 is a schematic illustration of the Gaussian distribution of polynucleotide reaction products.

Two major techniques have been developed to sequence DNA, a chemical one, the Maxam Gilbert technique, and an enzymatic one, the Sanger technique. The principle of the former involves labeling the 5'-hydroxyl of a DNA strand with $^{32}P$ and establishing chemical conditions that cause the DNA strand to break at the site of occurrence of one specific nucleotide, either A, T, G, or C. The net effect is to produce polynucleotides of differing lengths and the length of these polynucleotides reflects the occurrence of a base at a specific position in a DNA strand.

The principle of the latter technique involves copying a DNA template from a predetermined position on the template and terminating transcription where the terminating nucleotide is known from the specific reagent used during transcription. DNA polymerase I, a 5' to 3' DNA polymerase which requires a free 3'OH, is used with a primer to synthesize a radioactive single strand copy of a template DNA strand whose sequence is to be determined. To each of four reaction mixtures, a blocked derivative of one of the four different nucleotide substrates is added. These reagents are 2', 3' dideoxy analogues of each nucleoside triphosphate; they lack a 3' hydroxyl group. They block further extension of any chain into which they are incorporated. As a result, a series of polynucleotides is formed whose length reflects the position in the polynucleotide of a base corresponding to the analogues.

In both techniques, the reaction products are analyzed by separating them according to length by electrophoresis on a polyacrylamide gel and exposing the gel to x-ray film. The sequence can be read directly from bottom to top of the film. Advancing from one position of radiopacity to the next represents the addition of one nucleotide, and the identity of that nucleotide is assigned from the nature of the reaction that produced the radiopaque band.

These popular methods of DNA sequencing rely on the formation of a set of molecules all of which have a common property, a reference point at the 5' end of the molecule. Each member of the entire set has the following properties: they are superimposable on a portion of the parent molecule of the set of unknown sequence and the nature of the superimposition is such that all of the molecules can be superimposed on the parent when the 5' end of any molecule of the set and the 5' end of the parent molecule are aligned. The molecules make up a subset of the parent where subset denotes the relationship of identical sequence to some portion of the parent molecule and a total number of nucleotides less than or equal to that of the parent while maintaining a common 5' end. The entire subset refers to a group of molecules differing in length by one nucleotide ranging in length from one nucleotide to the number of nucleotides of the parent.

Molecules which differ in length by one nucleotide can be separated on a polyacrylamide gel. For any molecule, up to about 400 base pairs in length, a molecule that is identical except for possessing an additional nucleotide at the 3' end, will have a slower electrophoresis velocity. Thus, the smaller polynucleotide will migrate closer to the anode than the longer. Thus, if the last nucleotide of the molecule at the 3' end is known and all molecules have the same 5' end and are superimposable, the sequence can be determined from the knowledge of the identity of the last nucleotide. This is the basis of sequencing by the Maxam Gilbert and Sanger techniques.

Another strategy can be envisioned where the set of molecules are of length less than or equal to the parent molecule, are superimposable beginning from the 3' end of the parent and contain elements of length from one nucleotide to the number of the parent. In this strategy the common reference point is the 3' end. Utilizing the capability of separating of molecules differing by a single nucleotide and the knowledge of the last nucleotide on the 5' end, this procedure could serve to assign the identity of any 5' nucleotide as the length of the polynucleotide increases by one. The sequence of the parent can be assigned by reiteration of this procedure.

Catalyzed chemical reactions are used to generate the set of molecules in the case of the Sanger technique and chemical cleavage methods are employed to generate the polynucleotide set in the Maxam and Gilbert technique. Chemical or enzymatic reactions of these types have not been developed for the strategy where all the elements of the polynucleotide set have a common 3' end. However, because the approach is essentially the same, except that the opposite end of the parent molecule is chosen as the reference point, any limitations of the Maxam and Gilbert and Sanger techniques would probably apply to this strategy.

All of the described techniques are inadequate for sequencing DNA molecules of length greater than about 400 nucleotides due to inherent shortcomings. To sequence DNA of $10^5$ nucleotides, for example, by any of the above strategies, a set of molecules would have to be generated which contains all set elements that differ in length by one nucleotide from length one to $10^5$ and the molecules would have to be separatable on a polyacrylamide gel. Both requirements result in failure of the above mentioned methods.

Chemical reactions often yield a Gaussian distribution of reaction products. For the Maxam and Gilbert and Sanger techniques, set generation is dependent on chemical reactions for which the yield as a function of length is approximately a Guassian distribution, and for both methods, the average length is about 200 nucleotides.

In addition, molecules migrate at a velocity which is inversely proportional to their molecular weight. As the molecular weight increases, the difference in migration velocity decreases. Thus, molecules that differ by one nucleotide and range in length from one nucleotide to a length greater than 400 nucleotides can not be reliably separated by polyacrylamide electrophoresis to produce a band pattern from which the sequence can be determined. For these reasons, these methods are not appropriate for sequencing DNA molecules greater than 400 nucleotides in length.

To overcome these limitations, an approach of making overlapping fragments of the parent molecule has been widely implemented. The most common method of generating the fragments has been by cleavage with restriction enzymes. These fragments are individually sequenced by the methods of Maxam and Gilbert or Sanger and the total sequence is put together by overlap of the sequences of the fragments. However, this strategy also fails for sufficiently large molecules because of inherent limitations.

With present technology, a single fragment of DNA which contains less than 400 base pairs can be sequenced using the Sanger method of primed synthesis or the method of sequencing with base specific chemical cleavages of Maxam and Gilbert. These methods are described with other less predominant methods in *Methods of Enzymology*, Vol. 65, 1980, pp. 497–701. Both methods are convenient for single fragments of DNA; however, to sequence a very large piece of DNA, both methods rely on overlap of fragments of the larger piece which are independently sequenced. Sets of fragments are generated to produce overlapping sequence information, where the relationship of one set of fragments to another is unknown; any overlap of fragments from different sets is due to chance. With this approach it is apparent that as the length of the DNA fragment to be sequenced even approaches two orders of magnitude less than the size of a human chromosome the probability of obtaining sets of fragments whose sequences overlap each other sufficiently to rule out random overlap, so that the relative order can be assigned and thus allow the assignment of the sequence of the entire parent molecule, goes to zero; thus, the number of different randomly generated sets of differing fragments that are sequenced individually goes to infinity.

Furthermore, the popular method of primed synthesis depends on DNA cloning. DNA polymerase I extends primers from a 3' OH where the primer is bound to the complementary region at the 3' end of the template molecule which is the complement of the molecule which is sequenced. One of the difficulties with the Sanger technique is that suitable primers must be generated which will bind to only the 3' end of the template which is of unknown sequence. This problem can be circumvented by cloning the template into a region of a vector such that both its 5' end, in one orientation, and its 3' end in another orientation are contiguous to a region of the cloning vector of known sequence. Transcription is initiated from a primer which is complementary to this region.

Methods using cloning strategy are set forth in *Methods of Enzymology*, Vol. 101, 1983, pp. 3–122. The strategy of generating random sets of fragments that are individually sequenced until enough sets have been sequenced to provide overlap to assign accurately the relative order of the fragments is discussed in New M13 Vectors for Cloning—Shotgun Cloning, *Methods of Enzymology*, supra pp. 43–47. Sequencing procedures which depend on cloning as an integral part of the procedure are very difficult if not impossible to automate.

II. Strategy of the Sequencing Method of the Invention

The method of this invention is a readily automatable method which circumvents the problems inherent in the Maxam and Gilbert and Sanger techniques. The strategy is to create a group of molecules which contain a reference point which is internal. Initially, location of the reference point is unknown, but it exists in all of the molecules. The molecules are a family of polynucleotides comprising complementary copies of a portion of the parent molecule from which they are generated and are superimposable on the parent by alignment of this internal point of reference. The location of the point of reference or "axis," and the sequence of the parent molecule is solved for simultaneously by an algorithm called the matrix method of analysis.

The family of polynucleotides can be thought of as being all molecules which result from the sequential loss of nucleotides from the 5' and 3' end of the longest polynucleotide of the group. An ordered pattern of terminal nucleotide change and nucleotide compositional change occurs between members of sequential subsets. This algorithm exploits the pattern of ordered or systematic nucleotide compositional change and terminal nucleotide change that a designated longest polynucleotide with a given internal reference point and given nucleotide loss constraints can produce.

III. Criteria of Polynucleotides

The nucleotide sequence of a DNA strand can be solved by generating a family of polynucleotides overlapping portions of the DNA to be sequenced. Each family of polynucleotides forms a "sequential subset" of the longest polynucleotide of the group. The molecules are identical less one nucleotide from either the 5' or 3' end of a given molecule, and the former are defined as sequential subsets of the latter. A family of molecules with this intra member relationship is defined as a proper sequential subset. Also, if all such families are considered collectively, then another type of sequential subsets can be defined. A family of molecules can be selected from this group which are "sequential subsets" in the sense that any molecule of the family contains the exact same base composition less one nucleotide relative to another molecule of the family. The former is defined as an improper sequential subset of the latter if it does not contain the exact same sequence as the latter D less one nucleotide from the 3' or 5' end. The family is defined as "improper sequential subsets" and only one polynucleotide of a given length is present in the family.

The molecules can be depicted as follows:

$$K_{n'} \ldots K_4 K_3 K_2 K_1 X_1 X_2 X_3 X_4 \ldots X_n$$

where the series $K_1, K_2, K_3, K_4 \ldots K_{n'}$ represent the nucleotides of the polynucleotide 5' to the internal reference point, or axis, and the series $X_1, X_2, X_3, X_4 \ldots X_n$ represents the nucleotides of the polynucleotide on the 3' side of the axis. The 5' end with respect to the axis is designated as the "known" portion of the molecules (this does not necessarily imply that this sequence is initially known), and the 3' end of the polynucleotide is designated as the "unknown" portion. Thus, $K_1, K_2, K_3, K_4 \ldots$ represent the "known" sequence and $X_1, X_2, X_3, X_4 \ldots$ represent the "unknown" sequence. The distinction is that in the matrix, as described below, $K_1, K_2, K_3, K_4 \ldots$ appear as nucleotides, whereas the X's represent variables (define). The nucleotides of the "known" portion can be known extrinsically or they can be guessed.

There are at least three strategies of polynucleotide generation which yield a population of molecules from which sufficient data can be derived and analyzed by the proper form of the matrix method of analysis to solve for the sequence of the parent molecule uniquely.

A. Strategy I

According to Strategy I the polynucleotides are governed by the following constraints. No polynucleotide contains $X_2$ without containing $X_1$. In general terms, no polynucleotide contains $X_n$ without containing $X_{n-1}, X_{n-2}, \ldots X_1$. In addition, no polynucleotide contains $K_2$ without containing $K_1$. That is, no polynucleotide contains an unknown without containing all preceeding unknowns and, every polynucleotide contains all succeeding knowns if it contains any given known. As a set, all the polynucleotides satisfy these criteria and vary randomly at the 3' and 5' ends.

The criteria can be represented symbolically as follows:

$X_n \rightarrow X_1$ ($X_n$ implies $X_1$)

$K_{n'} \rightarrow K_1$ ($K_{n'}$ implies $K_1$)

$\ldots K_{n'} - X_{n} \ldots$ (The polynucleotides are random at the 5' and 3' ends; the knowns and unknowns are variables where K=Known, X=Unknown, n'=1 to 4 ... and n=1 to 4 ...)

B. Strategy II

All polynucleotides of a family conform to the following criteria. As in strategy I, no polynucleotide contains $X_2$ without containing $X_1$ and no polynucleotide contains $X_3$ without containing $X_2$ and $X_1$, and so on. In general terms, no polynucleotide contains $X_n$ without containing $X_{n-1}, X_{n-2}, \ldots X_1$. However, no restrictions are placed on the "known" nucleotides $K_1, K_2, K_3, K_4 \ldots$ As a set, all polynucleotides conform to these criteria and vary randomly at the 3' and 5' ends.

These criteria can be represented symbolically as follows:

$X_n \rightarrow X_1$ ($X_n$ implies $X_1$)

$K_{n'} \nrightarrow K_1$ ($K_{n'}$ does not imply $K_1$)

$K_{n'} - K_{n''}$ (The knowns are 3' and 5' random; the knowns are variables where the range of n' and n'' is 1 to 4 ...

$K_{n'} - X_n$ (the polynucleotides are 5' and 3' random; the knowns and unknowns are variables, where K=known; X=Unknown, n=1 to 4 ... and n'=1 to 4 ...)

C. Strateqy III

All polynucleotides of each family must conform to the following criteria. No polynucleotide contains $X_2$ without containing $X_1$ and no polynucleotide contains $X_3$ without containing $X_2$ and $X_1$, and so on. In general terms, no polynucleotide contains $X_n$ without containing $X_{n-1}, X_{n-2}, \ldots X_1$. However, no restrictions are placed on the "known" nucleotides; that is all possible polynucleotides of known with unknowns is possible as long as the first rule is satisfied. Furthermore, a change in known nucleotides of any two polynucleotides of the same composition implies that they have different terminal nucleotides. All polynucleotides adhere to these criteria and vary randomly at the 3' and 5' ends.

These criteria can be represented symbolically as follows:

$X_n \rightarrow X_1$ ($X_n$ implies $X_1$)

$K_{n'} \rightarrow K_1$ ($K_{n'}$ does not imply $K_1$)

For $K - X_{T1}$ and $K' - X_{T2}$, $\Delta K$ and $\Delta K'$, $X_{T1} \neq X_{T2}$ (Given two polynucleotides which begin with knowns and end with unknowns and have the same composition, a change in knowns for both implies that the terminals are not the same.)

$K_{n'} - X_n$ (the fragments are 5 and 3, random; the knowns and unknowns are variables, where K=known; X=unknown; n'=1 to 4 ... and n=1-4 ...)

An entire set of polynucleotides is defined as a family which satisfies all criteria of one of these three strategies. By determining the base composition and terminal base for sequential subsets, the sequence of the polynucleotides, and therefore, the sequence of the original DNA strand (the parent), can be solved by the matrix method of analysis.

IV. Principles of Matrix Method of Analysis

The basis of the matrix method of analysis is that there exists in all molecules, as described, a reference point which is a nucleotide position relative to the parent. These molecules compromise a sequential subset of a polynucleotide copy of a segment of the parent DNA. Nucleotides are lost from the 5' or 3' end. All the set elements are superimposable on the parent about this point of reference. The change in composition and terminal nucleotide and the order in which this change occurs is unique moving from one set element to the next, from the longest to the shortest element of the set.

The matrix method of analysis is a method that exploits the information that is known from the design of the polynucleotide generating reactions and the data obtained from the polynucleotides. The information is as follows:

1) the composition and change in composition of a polynucleotide as a result of random loss of one nucleotide from either the 3' or 5' end at each step; 2) the constraints on the random 3' and 5' loss described under criteria of polynucleotides; 3) the identity of the terminal base and the change in terminal base at each step; and 4) the order at which these changes occur.

The matrix method of analysis entails setting up a rectangular matrix where the designated longest polynucleotide appears at position (1,1). The sequence of one half of this molecule is "known" and the nucleotide sequence at the other one half of the molecule is designated "unknown" and represented by variables. The term "known" does not necessarily imply that the nucleotide sequence at the parent molecule is known initially. The division between the "knowns" and "unknowns" is the internal reference point. The location of the reference point is not necessarily known initially and can be changed by changing the knowns so that this sequence superimposes a different region of the parent molecule. That is, when the sequence is solved, it will be superimposable upon a region of the parent and the location of the internal reference point will be fixed. The location on the parent is at the line dividing the "knowns" and the "unknowns". If the 5, end of the sequence (and consequently the entire sequence) were superimposable on a different region of the parent, the location of the internal reference point would be different. Thus, the location of the internal reference point relative to the parent molecule is determined by the "knowns".

An exemplary matrix is shown below for polynucleotides which conform to the criteria set forth for Strategy I. For a designated longest polynucleotide which contains a total of eight (8) nucleotides the matrix consists of 5 rows and 4 columns.

constructed such that all the constraints governing the polynucleotides are satisfied and all possible polynucleotides are recorded in the matrix according to the described format.

The determination of the sequence of the polynucleotides proceeds as follows: starting at position (1,1) in the matrix, the base which has been lost is determined by the difference in base composition between the longest polynucleotide and the next longest of the set. The change is consistent with a move to position (1,2) and/or (2,1) of the matrix. The step is repeated for each polynucleotide of the family. These moves are down a column and/or across the row from left to right. Moves down a column or across a row from left to right are designated from/to moves. The result can be recorded, e.g. in a "lattice" which contains all coordinate positions arranged in levels such that each successive level from top to bottom corresponds to all possible from/to moves, and each successive level from bottom to top corresponds to all possible to/from moves. A to/from move is a movement up a column and/or across a row from right to left.

General Lattice

```
                    11
                  /    \
                12      21
              /    \  /    \
            13      22      31
          /    \  /    \  /    \
        14      23      32      41
      /    \  /    \  /    \  /    \
K₄K₃K₂K₁  24    33      42      51
      \  /    \  /    \  /    \  /
   K₃K₂K₁  34      43      52
         \  /    \  /    \  /
        K₂K₁  44      53
            \  /    \  /
             K₁      54
```

| Polynucleotide | Lattice Coordinate Position |
|---|---|
| $K_4K_3K_2K_1$ | 15 |
| $K_3K_2K_1$ | 25 |
| $K_2K_1$ | 35 |
| $K_1$ | 45 |

For each step, the base which could have been lost from the 3' or 5' end is determined and the appropriate move to a position in the matrix is made. This establishes the appropriate path in the matrix which can be designated by connecting the corresponding coordinates in the lattice. This procedure is repeated until all consistent from/to moves are recorded in the lattice. At least one path is formed from coordinate position (1,1) to a point of convergence, i.e., a coordinate position from which no further from/to moves can be made.

The next step is to determine which path is the correct path. This is accomplished by starting at a point of convergence and determining which to/from steps for $$K_4\ K_3\ K_2\ K_1\ X_1\ X_2\ X_3\ X_4$$

| $K_4K_3K_2K_1X_1X_2X_3X_4$ | $K_4K_3K_2K_1X_1X_2X_3$ | $K_4K_3K_2K_1X_1X_2$ | $K_4K_3K_2K_1X_1$ |
| $K_3K_2K_1X_1X_2X_3X_4$ | $K_3K_2K_1X_1X_2X_3$ | $K_3K_2K_1X_1X_2$ | $K_3K_2K_1X_1$ |
| $K_2K_1X_1X_2X_3X_4$ | $K_2K_1X_1X_2X_3$ | $K_2K_1X_1X_2$ | $K_2K_1X_1$ |
| $K_1X_1X_2X_3X_4$ | $K_1X_1X_2X_3$ | $K_1X_1X_2$ | $K_1X_1$ |
| $X_1X_2X_3X_4$ | $X_1X_2X_3$ | $X_1X_2$ | $X_1$ |

The matrix columns contain polynucleotides which have lost nucleotides at the 5' end; the rows are formed of polynucleotides which have lost from the 3' end. Nucleotides are lost from the 5' end down any column and lost from the 3' end across any row. The matrix is all single or binary decisions are consistent with the terminal base data as moves are made back to position (I,1) from the point of convergence. Assignment of a base to the 3' or 5' end is made by a to/from move which does not contradict the change in base. For all to/from moves, if the path that is chosen from one coordinate to another corresponds to a move across a row from right to left, then the base is assigned to the 3' end which is consistent with the move. That is the base change determined from the data occurred from the 3' end therefore the base lost is assigned to the 3' end. A contradiction arises if this assignment is inconsistent with terminal base data for the polynucleotide represented at the coordinate position or if the change in terminal base for this step is inconsistent with the data.

For all to/from moves, if the path that is chosen from one coordinate to another corresponds to a move up a column then the base change for that step indicates which base to assign to the 5' end. A contradiction would arise if the next "known" up the column in the matrix is different from that indicated by the base change.

The sequence is solved when at least one path is found from (1,1) to a point of convergence by from/to moves and to the (1,1) position from the point of convergence by to/from moves at each data step without contradictions.

The matrix method of analysis yields a unique solution for a matrix of all possible polynucleotides of size ($\frac{1}{2}M+1$, $\frac{1}{2}M$) that conform to the constraints for polynucleotides of Strategy I, or of size ($\frac{1}{2}M+1,M$) for polynucleotides of Strategy II, for any set of data of $M-1$ polynucleotides that are successively one nucleotide less and are sequential subsets from $M-1$ nucleotides to a dinucleotide. (The longest polynucleotide is M nucleotides in length.)

The key to the matrix method of analysis is that there is convergence to at least one of the terminal possibilities (point in the matrix at which no further from/to moves can be made). It may converge to more than one (e.g., if the sequence contained only A, or T, or C, or G bases, then it would converge to all possible termini of the matrix that yields the solution of the sequence). Once any terminus is determined to be correct, it can serve as an initiation point, that is, a point, or coordinate position from which the initial to/from move is made. A terminus representing a single nucleotide or single variable in the matrix is correct if it is consistent with the data. The sequence can be deciphered by making decisions at branch points and by taking the return path that is determined to be correct by the data, i.e. the terminal base and the change in the terminal base at each step. If more than one path is correct, anyone of the correct paths will yield the sequence.

For a given set of polynucleotides which terminate in the leftmost terminus ($K_4K_3K_2K_1$) (see lattice, page 25,) if the data contains $K_1$, $K_2$, $K_3$, $K_4$, then this coordinate (1,5) can not be excluded as an initiation point. But, if the sequence, $K_4K_3K_2K_1$, is known then this is an initiation point from which to initiate the path which gives the sequence.

In the special case, where only proper subsets, (i.e., polynucleotides which have the same sequence but differ by one nucleotide) were chosen and the 5' knowns are assigned from extrinsic information, if the sequence of the polynucleotide at the step at which a terminus is reached is not known but contains the same base composition as the terminus polynucleotide represented in the matrix, then this path can be determined to be correct if no other path exists or is consistent with the data. That is, it is proven correct by exclusion. Furthermore, if the data converges in this fashion, and also to one or more other possibilities then, a terminus containing no variables may be an initiation point, but it may also not be. The initiation point cannot be validated unless the sequence is known extrinsically at this point. In all cases, an initiation point is chosen that is consistent with the data; there will always be at least one. And, in the special case described, if it does not exist directly then it exists by exclusion.

In the case where polynucleotides conform to the rules of Strategy II where all possible polynucleotides of the knowns may be present in the set to be analyzed, these polynucleotides would occupy the appropriate position in the matrix and the additional coordinates would become part of the lattice at the proper level. Thus, sequential subsets could result in convergence to one or more of these new coordinate positions which would serve as initiation points. This is discussed in more detail under matrix method of analysis II. A special matrix and lattice is discussed under matrix method of analysis I.

For a population of molecules with special properties specified in Strategy III, a special form of the matrix method of analysis will yield a unique solution where information that was required to solve the sequence with data from a population of molecules generated with different constraints are not needed under these special conditions. In general, the "knowns" of any given parent molecule at position (1,1) can be defined by two different procedures which have implications as to the type of polynucleotides which can be generated.

The "knowns" can be assigned extrinsically. That is, a reiterative procedure can be implemented such that when the 3' half of the sequence of one set of polynucleotides is solved the 5' half, the "knowns", for the adjoining group of polynucleotides is solved. When a method is used which does not solve for the next contiguous half, the 5' half ("knowns") can be guessed. As described above, in essence, this amounts to a guess of the position of the axis on the parent molecule. Alternately, the axis in the case where the "knowns" are assigned extrinsically may be guessed independently which conversely determines the "knowns."

Sequential subsets, as defined previously, can be polynucleotides of the exact same composition and sequence as the predecessor minus one nucleotide, i.e. a proper sequential subset, or each polynucleotide of the set could be a molecule that has the exact same composition minus one nucleotide, but a different sequence, an improper sequential subset. All of these variables have implications with regard to the nature of the set of generated molecules and the analysis of these molecules.

As will be described under Matrix Method of Analysis I and Matrix Method of Analysis II, implementation of the Matrix Method of Analysis requires that the solution for the position of the "axis" be guessed (Matrix Method of Analysis II) or requires that both the position of the "axis" and the "knowns" must be guessed (Matrix Method of Analysis I). Furthermore, a proper set of sequential subsets must be guessed for both methods. Also, a guess can be made for the position of the axis, and the set of proper sequential subsets with or without the composition of the 5' one half of the polynucleotide being known extrinsically and an unambiguous solution can be found by the matrix method only if the correct guesses are put forth.

. From data, the sequence is verified by the absence of contradictions; conversely, fictitious data can be proposed from guesses for the sequence other than the correct sequence and the fictitious data may be consistent with the base composition and the terminal base of each true polynucleotides, but the matrix generated from the incorrect guess will not yield an unambiguous solution using the real data. The matrix method of analysis reconstructs the sequence in the exact order that the nucleotides are successively eliminated from the 3' and 5' end. From other guesses a set of polynucleotides consistent with the data may be proposed but a different order of elimination must be imposed and the matrix method will only yield the correct order for the correct matrix which is unique to each guess. Also, the four data properties are unique due to the way the polynucleotides were generated and the combination of a unique data set and matrix yields contradictions unless all variables are guessed correctly. When that occurs, the sequence is unambiguously determined. If a contradiction is encountered, depending on the strategy of analysis and strategy of polynucleotide generation, one or more of the following procedures is followed: new sequential subsets are chosen, the position of the axis is shifted, or a new guess is made for the "knowns".

For example, if the 5' end of the parent is known initially and an improper sequential subset is chosen, then a contradiction will arise. The molecule has the same composition and reference point as a proper sequential subset but when it is aligned with the reference point on the parent and superimposed, it is readily apparent that the 3' and 5' ends of the improper sequential subset occurs at a different positions along the parent then a proper sequential subset. The matrix converges on a path which is an ordered record of the nucleotides that were lost from the 3' and 5' end relative to the axis; therefore, assigning an improper subset to a matrix position corresponding to a proper one gives rise to a contradiction in later analysis. The C ordered-loss from the 3' and 5' end must be different relative to the reference point for this polynucleotide because it is a different polynucleotide and this will be apparent in the analysis when a from/to step is forced in the matrix which commits the molecule to a path that represents a different loss pattern from that which actually occurred due to the analysis constraint that any polynucleotide which contains $X_n$ must contain all previous unknowns including $X_1$. The contradiction will be noted with one of the to/from moves. At this point a new set of sequential subsets is guessed. When all the variables are guessed correctly, no contradictions will arise and the sequence is unambiguously assigned.

Examples of Solving Sequences by the Matrix Method of Analysis

To further illustrate the matrix method of determining sequence, examples of its application are given below. In each example a matrix for a polynucleotide family of eight nucleotides in length is shown. The lattice diagram shows all possible matrix from/to moves consistent with the change in composition data. The column labeled "path" represents the possible to/from moves in the matrix which are consistent with the terminal base data and the change in terminal base. The path which determines the solution to the sequence is read from bottom to top.

EXAMPLE 1

Example 1

1 4 6 7   5 3 2
A T T C G C T A
$X_1 X_2 X_3 X_4$

| | 1 | 2 | 3 | 4 |
|---|---|---|---|---|
| 1. | $ATTCX_1X_2X_3X_4$ | $ATTCX_1X_2X_3$ | $ATTCX_1X_2$ | $ATTCX_1$ |
| 2. | $TTCX_1X_2X_3X_4$ | $TTCX_1X_2X_3$ | $TTCX_1X_2$ | $TTCX_1$ |
| 3. | $TCX_1X_2X_3X_4$ | $TCX_1X_2X_3$ | $TCX_1X_2$ | $TCX_1$ |
| 4. | $CX_1X_2X_3X_4$ | $CX_1X_2X_3$ | $CX_1X_2$ | $CX_1$ |
| 5. | | $X_1X_2X_3X_4$ | $X_1X_2X_3$ | $X_1X_2$ | $X_1$ |

| Lattice | Composition Data | Δ | Terminal Nucleotide | Path | Sequence |
|---|---|---|---|---|---|
| 11 | 3T,2C,1G,2A | A | A | 1,1 | ATTCGCTA |
| 12  21 | 3T,2C,1G,1A | A | A | 2,1 | TTCGCTA |
| 13  22 | 3T,2C,1G | T | T | 2,2 | TTCGCT |
| 14  23  32 | 2T,2C,1G | T | C | 2,3 | TTCGC |
| ATTC  24  33  42 | 1T,2C,1G | C | C | 3,3 | TCGC |
| TTC  34  43  52 | 1T,1C,1G | T | G | 3,4 | TCG |
| TC  44  53 | 1C,1G | C | G | 4,4 | CG |
| C  54 | 1G | | G | 5,4 | G |

EXAMPLE 2

Example 2

1 2 5 7   6 4 3
A G T C A T T G
$X_1X_2X_3X_4$

| | 1 | 2 | 3 | 4 |
|---|---|---|---|---|
| 1. | $AGTCX_1X_2X_3X_4$ | $AGTCX_1X_2X_3$ | $AGTCX_1X_2$ | $AGTCX_1$ |

-continued

| | Lattic | Composition Data | Δ | Terminal Nucleotide | Path | Sequence | |
|---|---|---|---|---|---|---|---|
| 2. | GTCX$_1$X$_2$X$_3$X$_4$ | GTCX$_1$X$_2$X$_3$ | | | GTCX$_1$X$_2$ | GTCX$_1$ | |
| 3. | TCX$_1$X$_2$X$_3$X$_4$ | TCX$_1$X$_2$X$_3$ | | | TCX$_1$X$_2$ | TCX$_1$ | |
| 4. | CX$_1$X$_2$X$_3$X$_4$ | CX$_1$X$_2$X$_3$ | | | CX$_1$X$_2$ | CX$_1$ | |
| 5. | X$_1$X$_2$X$_3$X$_4$ | X$_1$X$_2$X$_3$ | | | X$_1$X$_2$ | X$_1$ | |

```
              11         3T,2G,1C,2A       G     1,1 1,1   AGTCATTG   AGTCATTG
            /    \                      A
          12      21     3T,2G,1C,1A       G     2,1 2,1   GTCATTG    GTCATTG
         /  \   /  \                    G
       13    22     31   3T,1G,1C,1A       G     3,1 3,1   TCATTG     TCATTG
      /  \  /  \  /  \                  G
     14    23    32     3T,1C,1A          T     3,2 3,2   TCATT      TCATT
    /  \  /  \  /  \                     T
 AGTC   24   33    42   2T,1C,1A          T     3,3 4,2   TCAT       CATT
    \  /  \  /  \  /                     T
  GTC    34    43       1T,1C,1A          T     4,3 4,3   CAT        CAT
      \  /  \  /                         T
       TC    44         1C,1A             A     4,4 4,4   CA         CA
         \  /                            C
          C    54       1A                A     5,4 5,4   A          A
```

V. Approaches to Overlapping Sequences

A. Preferred Approaches

At least two approaches exist for generating polynucleotides which conform to the criteria set forth above and provide overlapping portions of the DNA to be sequenced.

In one approach where the polynucleotides conform to the criteria set forth under Strategy III, the DNA to be sequenced is digested into restriction fragments using the same procedures that are used in sequencing long polynucleotides by the conventional Maxam and Gilbert and Sanger techniques. However, there is a major departure from the strategy and methods of the conventional techniques from this point. From each DNA restriction fragment an RNA transcript(s) is/are made. The transcripts are then extended using the original DNA as template. Extension on this template produces overlapping sequence data so that the sequence data from the single set of restriction fragments can be ordered appropriately. In other words, the RNA copy serves as a primer for extension into the region that the appropriate RNA copy made from the 5' contiguous restriction fragment, would bind. Because all of the RNA transcripts are extended, overlap data is generated for all copies, and at the same time, for all restriction fragments, because the information is complementary. Therefore, the entire parent molecule can be sequenced from one set of restriction fragments. The method is described in more detail below.

The second approach of producing overlapping polynucleotides is to use the principle that the graph of the average polymerization reaction product length as a function of time has a positive slope which can be determined experimentally. For any given reaction time concentrations of the polymerization reaction products of various lengths will be approximately Guassian in distribution and centered about an average length. (See FIG. I). Manipulation of reaction parameters can alter the average and standard deviation of the yield distribution of the polynucleotide lengths. Because polymerization proceeds in a 5' to 3' direction the sequence can be solved successively by using a reiterative methodology where the reaction products of reaction n are related to or are used to determine the distribution of reaction products of reaction n + 1, where n is the reaction number and a higher number indicates a distribution of products with a longer average length.

Various schemes of polynucleotide generation can be devised to produce polynucleotides described in Strategy I and II and which exploit the principles of the time dependence of the polymerization reaction and the principle that the products from reaction n can be used to determine the reaction product distribution of reaction n+1.

In its simplest form, polymerization reactions can be run for increasing periods of time with mass labeled nucleotides. That is, the larger the reaction number, n, the longer the polymerization reaction occurs. The reaction is timed so that a series of overlapping Guassian product distributions are obtained as illustrated in FIG. 1. Then, a portion of the reaction products from reaction n is transfered to reaction n + 1, and the transferred polynucleotides bind to 5' end of the template and the 5' end of all longer polynucleotides are displaced by the shorter transfered polynucleotides. All displaced DNA is selectively digested and a set of polynucleotides random at the 3' and 5' ends is generated. The polynucleotides of this set are separated on the basis of size and nucleotide composition. Each polynucleotide of the set contains all of the preceeding "unknowns" if it contains any unknown and all succeeding "knowns" if it contains any "known" and the axis is at the position of the 3' terminal of the longest polynucleotide from reaction n.

To sequence by this second strategy of generating overlapping polynucleotides, the final polynucleotide distribution must be such that if all of the polynucleotides were superimposed on the parent, then the solved for region of the "unknown" part of the parent, which is less than or equal to the total "unknown" region of superimposition, and the "known" region must be superimposed to at least this extent. "Known" in this case refers to the sequence that has been elucidated in previous reactions. Because of the nature of the last method described above for polynucleotide generation, the shorter the smallest polynucleotides in reaction n and n+1, the greater the total area of superimposition on the parent. Another way to look at this effect is to consider that shorter polynucleotides cause the total number of different polynucleotides generated to increase. To decrease the total number of different final polynucleotides, the shorter polynucleotides can be selectively eliminated. Procedures that follow represent schemes for polynucleotide generation all of which contain a method to eliminate small polynucleotides. The extent of this elimination can be controlled to create the desired distribution of lengths in the final polynucleotides which are those from which data is obtained.

A scheme which uses this approach to polynucleotide generation to produce polynucleotides of Strategy II, is to generate primers and displacers by running the polymerization reactions for varying lengths of time; transferring the products from reaction n to n+1, and then digesting all displaced DNA and the part of the template which does not have any annealing DNA. The primers and displacers are produced by making a copy of the template which is not digested with and without mass labeled nucleotides and using half of the products as the primers which are mass labeled to extend with mass labeled nucleotides on the template and half which are not labeled as displacers to randomly displace the 5' end of the extended products. The displaced DNA is digested. The resulting distribution is random at the 3' and 5' end, contains all previous unknowns for any given unknown and the axis is at the position of the 3' terminal from the longest polynucleotide from reaction n.

A third method is to run successive RNA polymerization reactions for a longer time. The products are then transferred from reaction n to reaction n+1 and the longer polynucleotides are products are allowed to displace the shorter polynucleotides; the longer polynucleotides and the annealed polynucleotides are precipitated selectively; the shorter polynucleotides are removed; the precipitated polynucleotides are resuspended and the transcripts are extended with mass labeled deoxynucleotides and terminated with mass labeled dideoxynucleotides and the primers are selectively degraded. The product would be random at the 3' and 5' ends and would contain all preceeding "unknowns" for any given "unknown" and the axis would be at the position of the 3' terminal of a primer.

This precipitate procedure could be implemented in the absence of transfer from reaction n to n+1. And, the distribution is determined by the time dependence of the polymerization reaction. These methods are discussed in more detail below. The latter two methods are shown schematically in FIG. 3.

B. Additional Methods of Generating Polynucleotides

In the previously described methods for generating polynucleotides, which are random at the 3' and 5' end, RNA was extended with DNA and the RNA was hydrolyzed to make the strands 5' random. (This applies to the primer extender method and the precipitate methods, but not to the restriction enzyme method). An alternative method for forming these hybrid polynucleotides is to reverse the order. DNA can be extended with RNA and the RNA can be terminated by polymerizing the RNA with RNA polymerase in the presence of a DNA polymerase and the 4 dideoxyribonucleoside triphosphates, that are mass labeled, or just DNA polymerase with $Mn^{2+}$ substituted for $Mg^{2+}$. The DNA can then be selectively degraded by the exonuclease that degrades DNA but not RNA. The purpose of this alteration is that it may be possible to polymerize polynucleotides of DNA that are much greater in length than RNA polynucleotides. Furthermore, in any method using RNA synthesis from a primer that requires production of very long strands, a viral, bacteriophage, or bacterial RNA promoter can be ligated to the 5' end of the DNA to be sequenced and this will have high activity and since the promoter is not found in human DNA, transcription into RNA will only occur from this point. Examples of bacteriophage promoters which demonstrate this phenomenon are Sp6 and Tn7.

Best Mode of Carrying Out the Invention

Figure 2:
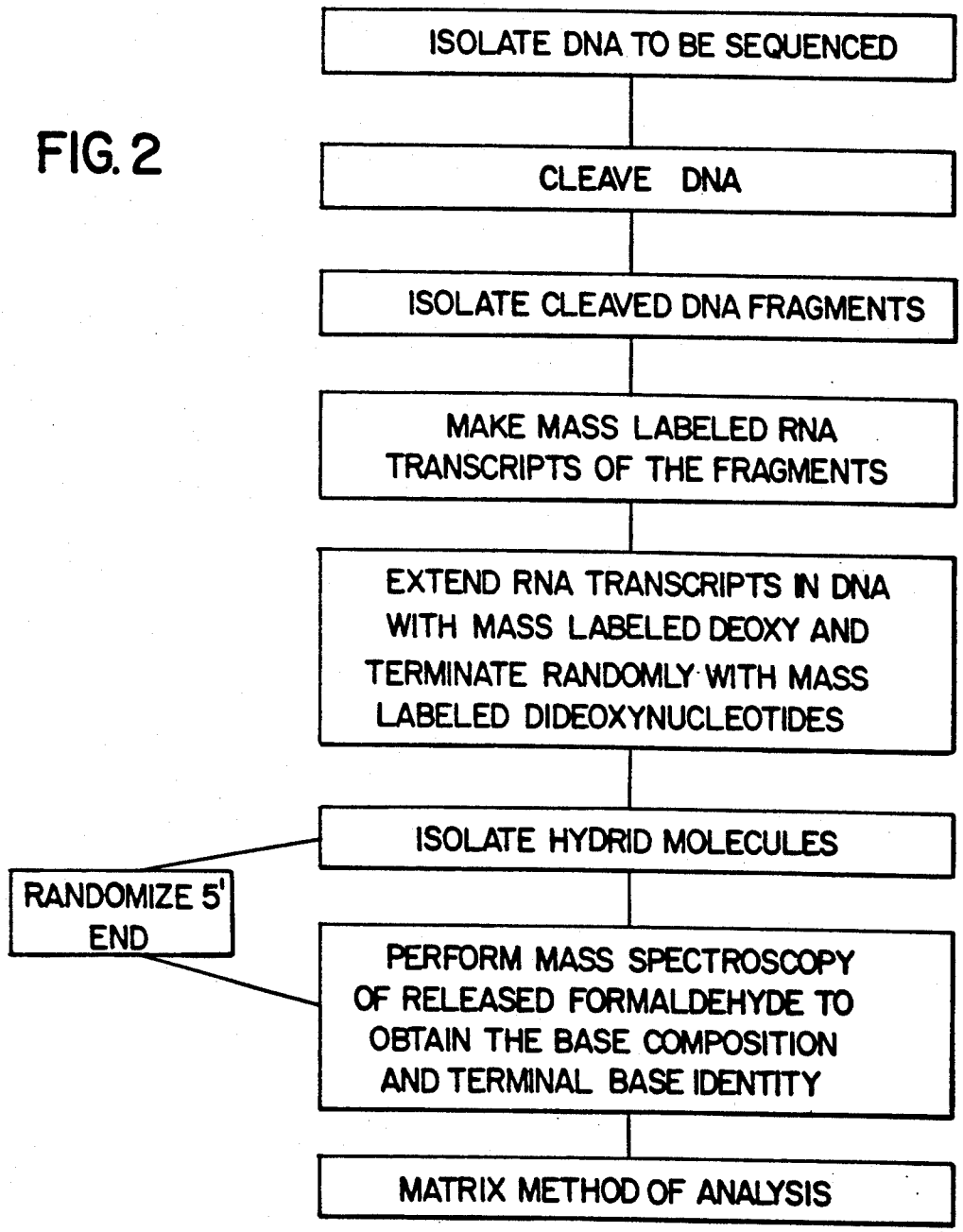
FIG. 2 is a flow chart of the steps of the Best Mode of Carrying Out the Invention.

This mode is shown schematically in FIG. 2.

I. Isolation of DNA to be Sequenced

DNA can be isolated and purified for the sequencing procedure from cells by various methods.

From eukaryotic cells, cell nuclei can be separated from other cellular organelles by differential centrifugation. An aqueous homogenate of the nuclei can be then formed and proteins can be removed from this homogenate by extraction with phenol or chloroform or a mixture of these two solvents.

If desired, individual chromosomes of eukaryotic cells can be isolated by methods such as flow cytometry. The chromosomes can then be digested into smaller fragments for sequencing by partial enzymatic digestion with a restriction endonuclease or cleaved by other techniques such as ultrasound.

To provide ample DNA for the sequencing techniques, DNA may be cloned. Gene libraries of genomic DNA can be created by taking the total DNA of a cell or chromosome, digesting it into fragments, inserting the DNA fragments into a cloning vector and introducing the vector into yeast or bacterial hosts. The vector will replicate along with its host and provide a convenient source of DNA for sequencing. Large DNA fragments for cloning can be generated by random shearing of DNA or by partial digestion with a suitable restriction enzyme. A variety of cloning vectors can be used to create the gene library. Examples are the yeast artifical chromosomes and bacteriophage vectors. Restriction enzymes may be used to generate DNA fragments with cohesive ends which bind complementary cohesive ends of a cleaved cloning vehicle. The DNA fragment can then be inserted at the cleavage site of the cloning vehicle and yeast or bacterial host transformed with the recombinant vector.

II. Generation of Polynucleotides

The preferred method of generating the polynucleotides which satisfy the criteria set out above under Strategy I, II or III entails the synthesis of a set of mass labeled RNA/DNA hybrid molecules from randomly generated restriction enzyme fragments of the DNA to be sequenced (hereinafter "parent DNA").

A. Preparation of Fragments of Parent DNA

The sample of isolated and purified parent DNA is divided into two portions. One portion is set aside for use in later steps of the procedure. The other portion is used to generate restriction fragments of an average predetermined length. The restriction fragments are generated by digesting the parent DNA with a restriction endonuclease or a combination of restriction endonucleases. The length of the fragments can be estimated by calculating the frequency with which a given recognition site or sites would be expected to occur randomly in the parent. This is based upon the assumption that the recognition sites for restriction endonucleases are distributed randomly along the DNA of an organism. For instance, the tetranucleotide target for the restriction endonuclease Mbo I will occur about once in every 256 nucleotides. Therefore a complete digest of a DNA strand with Mbo I should provide fragments averaging about 256 nucleotides in length. The hexanucleotide site recognized by Bam HI will appear on average once in every 4096 nucleotides.

The restriction enzyme digest is carried out to completion to produce fragments of the desired length. The digestion reaction may be repeated, if necessary, to achieve complete digestion.

The preferred average length of the fragments should be in the range of about 20 to about 400 nucleotides. The upper limit of about 400 represents the limit of reproducible separation of fragments of this size range by electrophoresis.

The fragments resulting from this restriction enzyme digest are then separated according to length. The preferred method of separating the fragments is the standard procedure of agarose or polyacrylamide gel electrophoresis. Gels containing the appropriate amounts of agarose or polyacrylamide can be formulated for optimum separation of fragments in the 20 to 400 nucleotide range. Differential migration of fragments of different length allows separation and individual elution of the separated fragments.

Gels can be formulated which separate double-stranded fragments differing in length by only a single nucleotide.

B. Separation of Complementary DNA Strands

After separation of individual fragments, the complementary DNA strands of each fragment are dissociated and separated. A suitable method for separating the strands entails denaturing the fragment with alkali and then electrophoresing the denatured strand on an agarose or polyacrylamide gel at neutral pH. Because the two dissociated strands generally have slightly different shapes, and consequently different mobilities in the gel, the migrate differently in the gel and can be eluted separately.

Other suitable methods of separating the DNA strands include cesium-chloride gradient ultracentrifugation or the poly (U,G) method and cloning in M13 bacteriophage.

Separated single strands can then be concentrated by precipitation with ethanol or isopropanol. The DNA polyanion is not soluble in alcohol.

C. Synthesis of Mass-labeled RNA Copies of Strands

For each isolated single strand of the fragments, an RNA copy is produced with ribonucleotides labeled with isotopes at the 5th position of the pentose component of the ribonucleotides. (See below for discussion of the theory and procedure for using mass labeled nucleotides).

There are at least two procedures for producing RNA copies of the fragments. The first is primed RNA synthesis. Mass-labeled ribonucleotide primers are synthesized having a sequence complementary to the recognition site of the endonuclease used to generate the DNA fragments from the parent DNA. Polymerase reactions are set up in an appropriate buffer each containing the DNA polynucleotide template, the mass-labeled primer, the four mass labeled ribonucleotides and RNA polymerase. The primer is paired with the tetra- or hexanucleotide recognition site of the DNA fragment and provides a site for RNA polymerase imitation of RNA synthesis. The polymerase will synthesize a RNA copy of the DNA fragment.

In the second procedure, which is the preferred method, RNA copies are made without use of a primer. If ribonucleotides are added to the reaction mixture in high concentration in the absence of sigma factor, which controls initiation of RNA polymerization only from special DNA sequences called promoters, then RNA polymerase initiates RNA synthesis at random points along the DNA template and a free end stimulates initiation at that site. The procedure is carried out in substantially the same way as for primed RNA synthesis except that no primers are added and a concentration of about 2 millimolar ribonucleotides is used.

Upon completion of the reactions by either procedure, a DNAase is added to destroy the template DNA fragment. The resulting RNA transcripts are separated by molecular size.

A preferred method for this separation step is agarose or polyacrylamide gel electrophoresis. The aim is to isolate the longest RNA copy by collecting fractions of eluant from the gels frequently enough to permit collection of discrete RNA bands. Although isolation of the single largest RNA transcript is preferable, the procedure tolerates as many as four different polynucleotides. (See Matrix Method of Analysis I.)

A method of using mass spectroscopic detection of bands containing a single polynucleotide is described in the section entitled Automating the Method.

D. Extension of RNA Transcripts on Parent DNA Template- 3' Randomization

The RNA transcript (or transcripts, up to as many as four) are extended, with the parent DNA serving as template for the extension, with mass-labeled deoxynucleotides to generate RNA/DNA hybrid polynucleotides which are terminated randomly on the 3' end (the DNA end). This can be accomplished by employing the modification of the procedure of Sanger et al.

Polymerase reactions are set up in appropriate buffers, each containing the RNA transcript (or transcripts), a single-strand of the parent (the original template), all four mass-labeled deoxynucleotides, all four mass-labeled dideoxynucleotides, and DNA polymerase I. This polymerase will initiate DNA synthesis at the 3' end of the RNA transcript (which serves as a primer). $Mn^{2+}$ may be substituted for $Mg^{2+}$ in the reaction mixtures to improve the efficiency of DNA synthesis at the RNA primer. This procedure generates a population of RNA/DNA polynucleotides ranging in size from the original RNA transcript with one dideoxynucleotide on the 3' end to molecules roughly 400 nucleotides in length.

Both complementary strands of the parent DNA are used as templates. In each case, the longest RNA transcripts copied from appropriate strands of the smaller restriction fragment made from the parent are used.

If non-complementary RNA interferes with subsequent steps it can be removed by hydrolysis with a 3' to 5' exonuclease that requires a 3' OH, for example, snake venom exonuclease.

Both methods may give rise to either subsets of a single molecule or subsets of more than one molecule; therefore, the data must be treated as if subsets are made from the loss of nucleotides randomly from the 3' and 5' end of the parent polynucleotide and the matrix method of analysis I must be used as described in this discussion.

A single RNA copy of the restriction fragments is desired. The RNA copy's length must be greater than half the length of the restriction fragment or it must be at least 20 base pairs in length and a copy of a portion of the 5' half of the restriction fragment. The latter two conditions eliminates the possibility that the copy will bind elsewhere in the template by random probability and insures that enough of the 5' end will be sequenced to complement the sequence determined for the antiparallel strand, so that the entire polynucleotide and adjoining overlap region with the next restriction polynucleotide is sequenced. Furthermore, if one pure polynucleotide is isolated from either RNA copy procedure with subsequent steps carried out and mass spectrum data obtained, then the sequence is solved for by taking sequential subsets from the first mass scan where the change from a subset to one with the same composition but one nucleotide less in each case assigns the lost nucleotides in order from the 3' to the 5' direction. Using sequential subsets from the mass data from the second scan following the 5' randomization procedure, a gain of a nucleotide from the smallest to the largest polynucleotide assigns those nucleotides in order in the 3' to 5' direction.

If more than one RNA copy of the restriction polynucleotide is isolated, then the Matrix Method of Analysis must be used because using the previous procedure on more than one polynucleotide and overlapping the sequences may result in more than one solution due to interchange of assignment between polynucleotides and/or shifting of the overlap region of the polynucleotides. The solution is discussed under Matrix Method of Analysis I.

E. Separation of RNA/DNA Polynucleotides

RNA/DNA hybrid molecules produced by the procedure outlined above will be about 20014 400 in number. All molecules are comprised of mass-labeled ribonucleotides, deoxynucleotides and a 3' terminal dideoxynucleotide.

The hybrid polynucleotides are then separated by length preferably by polyacrylamide or agarose gel electrophoresis. Each successive molecule differing in length by one nucleotide can be resolved.

The RNA/DNA polynucleotides in bands can be collected as separate fractions from the gel. Bands eluted from the gel can be monitored by mass spectrometry as described in the Automating the Method section, by an absorption at wavelengths of 260 and 280 nanometers or by ethidium bromide fluorescent.

III. Determining Base Composition and 3' terminal Base of Polynucleotides

The separated RNA/DNA hybrid molecules can be reacted to release labeled formaldehyde which is mass spectroscopically analyzed to determine the base composition of each polynucleotide and the identity of the 3' terminal dideoxynucleotide.

IV. Detailed Methodology of the Best Mode (Methods I)

The steps of the preferred method have been outlined above. The method is illustrated in the format of a flow chart in FIG. 2. The detailed methodology of each step is described below.

Step I: Isolation of DNA to be Sequenced

The DNA to be sequenced is isolated from genomic DNA and is separated into two aliquots. One aliquot is set aside for Step III. A restriction digest is performed on the other aliquot so that restriction fragments of an approximate length of 200 base pairs are obtained. The restriction fragments are then made single stranded. The methodology follows.

The individual chromosomes of the human genome can be isolated by flow cytometry to provide pure DNA to make a library or a set of restriction fragments which can be sequenced. See e.g., Gray et al., (1987) *Science* 238, 323-329; Davies et al. (1981) *Nature* 298, 374-376; Batholdi et al., *Cytometry* 3, 395-401; and Leba, (1982) *Cytometry*, 145-154. The chromosomes can be digested with restriction enzymes into fragments of length which can be estimated by the frequency that a given restriction site would occur by chance in a DNA molecule of a given length. Once cleaved, the DNA fragments are separated by size or composition. The preferred method is to separate the fragments by gel electrophoresis, (see e.g. Maniatis et al., *Molecular Cloning, a Laboratory Manual*, Cold Springs Harbor, 1982 (hereinafter "Maniatis"), pps 173-185, 478). Also, the technique of pulse-field gradient electrophoresis could be used as described in D. Schwartz and C. Cantor, *Cell* 37, 67 (1984), and denaturing gradient gels could be implemented. See Fisher and Lerman, *PNAS* 80, 1579 (1983) and Learman et al. *Annu. Rev. Biophys. Bioeng.* 1984, 13:399-423. Methods of visualizing and removing nucleic acids from gels are described in Maniatis, p. 163-172; Vogelstein et al. *PNAS* 76(2):615-619. For removing DNA from polyacrylamide gels, see Maniatis, p. 178.

Other methods include CsCl gradient ultra-centrifugation, see e.g., Maniatis, p 93-94, and various chromotographic techniques such as, reverse phase or ion exchange HPLC. For separation of large DNA or RNA polynucleotides by HPLC, see Larson et al., *J.B.C.* 254:5535-5541(1979); Patient et al. *J.B.C.* 254:5542-5547(1979); Patient et al. *J.B.C.* 254:5548-5554(1979 . For separation of short polynucleotides by HPLC, see Gait et al., *Nucleic Acid Res.* 10(20), 6243-6254(1982); Dizdaroglu et al., *J.Chrom.* 171:32 -330(1979); Pearson et al., *J.Chrom.* 200:137-149(1983); Haupt et al., *J.Chrom.* 260:419-427(1983); McLaughlin et al., *Anal.Biochem.* 124:37-44(1982); McFarland et al., *Nucleic Acid Res.*7(4), 1067-1080(1978). Pure polynucleotides from a restriction digest can also be isolated by cloning methodologies which allows for isolation and amplification of DNA molecules.

Fragments of exogenous DNA that range in size up to several hundred kilbase pairs can be cloned into yeast by ligating, them to vector sequences that allow their efficient propagation as linear artificial chromosomes, see Burke, et al., *Science* 236:806-812 (1987).

Several additional types of vectors can be used to clone fragments of foreign DNA and propagate them in appropriate host cells (e.g., *E.coli*.) These include plasmids, bacteriophage lambda, cosmids, bacteriophage M13. These vectors are discussed in Maniatis, pp. 2-54. Propagation and maintenance of bacterial strains and viruses is discussed in Maniatis, pp. 55-74. Large scale isolation of plasmid DNA is discussed in Maniatis, pp. 75-98. Introduction of plasmid and bacteriophage lambda DNA into *E.coli* is discussed in Maniatis, pp. 247-268. Construction of Genomic libraries is discussed in Mantiatis, pp. 269-308. Plasmid or bacteriophage lambda DNA can be rapidly isolated from plasmids grown as individual colonies or plaques by methods described in Maniatis, pp. 365-373. Cloning methods are also discussed in *Methods of Enzymology*, vol. 101, 1983, pp. 3-123.

The procedure of using restriction digests and separation of the product fragments can be repeated as many times as necessary using any combination of the above referenced strategies until DNA restriction fragments of length between 20 and 400 base pairs is obtained.

A complete method for preparation of double-stranded restriction fragments is given in *Methods of Enzymology*; vol. 65, 564–565, (see preparation of restriction fragments).

Isolated double stranded restriction fragments are made single stranded by electrophoresis on strand separating gels as described in Maniatis pp. 179–185.

The final isolated purified single stranded fragments can be concentrated by the method of precipitation with ethanol or isopropanol described in Maniatis, pp. 461–463.

Step II: Preparation of RNA Transcripts

An RNA transcript of the single stranded restriction fragment is made with mass labeled ribonucleotides. (See Determination of the Base Composition and Terminal Base Identity Section.) There are at least two procedures of making RNA transcripts.

Procedure A. RNA copies of the restriction fragments are made by the primed RNA synthesis procedure described in *Methods of Enzymology*; vol. 65, 1980, pp. 497–499. Mass labeled primers are used. The primers are complementary to the restriction enzyme site which was cleaved to generate the restriction fragment. Mass labeled ribonucleotide triphosphates are used in place of $-32p$ NTP's. RNA copies are separated and bands are collected by a fraction collector during electrophoresis or chromatography. The instrumentation for collecting eluted fractions from an electrophoresis procedure is described below in the sections entitled Electrophoresis Instrumentation and Automating the Method.

Procedure B. RNA transcripts of the single stranded restriction fragments are made using *E. coli* RNA polymerase where the 3' free end of the restriction fragment serves as a promoter for core polymerase (*Nature*, Vol. 223 (1969), pp. 854–55). The polymerization protocol is described in *Methods of Enzymology*: Vol. 65 (1980), pp. 497–99, with the exceptions that all nucleotide triphosphates are mass labeled, that no primer is used, and that 2 mM nucleotide triphosphates are used to stimulate RNA polymerase to initiate at the 3' end without a primer. Yeast B enzyme may be substituted for *E. coli* polymerase. In the presence of denatured DNA the average length of RNA chains synthesized by the yeast B enzyme are larger than those polymerized by the *E. coli* enzyme. With the former enzyme, the average chain-length growth rate at 30° C. is about seven nucleotides per second (*The Enzymes*, Boyer, Vol. X, p. 309).

For each procedure the largest RNA copy is isolated. It is preferable to collect fractions frequently so as to isolate a band containing a single polynucleotide, generally the largest polynucleotide. However, the sequencing procedure will tolerate four different polynucleotides in the band isolated. If five different polynucleotides are isolated, then a different band from the separation procedure may be used or the sequence determined for the antiparallel strand can suffice.

If mass spectrometry is used as a method to monitor the bands, then a band which contains a single polynucleotide can be selected when the peaks corresponding to the possible bases are of integer relative intensity. This method is described in the Automating the Method Section.

Step III: Extension of RNA Transcripts in DNA

The RNA copies are used as primers and are extended on the DNA template with mass labeled deoxyribonucleotides. The extension is terminated randomly with mass-labeled dideoxyderivatives so that the primer is extended to a maximum length of approximately 400 nucleotides, and the product polynucleotides are separated by methods described in Step IV. See also Electrophoresis Instrumentation.

Mass labeled deoxy- and dideoxyribonucleotides are used and the A, T, C, and G reactions are performed as a single reaction with reactant concentration in a final concentration as by Smith DNA Sequence Analysis by Primed Synthesis Primers, *Methods of Enzymology*; vol. 65, pp. 561–580 (1980). DNA polymerase I will initiate DNA systhesis at an RNA primer as described by Lee Huang et al., *PNAS* 511:1022–1028 (1964). $Mn^{2+}$ may be substituted for $Mg^{2+}$ if DNA extension at the RNA primer occurs with low efficiency. The effect of $Mn^{2+}$ on the substrate specificity of DNA polymerase I is described in *DNA Replication*, Kornberg, p. 151 and in *Methods of Enzymology*; vol. 65, p. 572 (1980).

A portion of the parent and a portion of the complementary antiparallel strand are sequenced in two separate reactions. In one extension reaction, the longest RNA copy made from the single stranded restriction fragment serves as a primer where the double stranded parent serves as the template. The longest RNA copy made from the complementary restriction fragment serves as primer for a separate reaction in which double-stranded parent is used as the template. A method by which the double stranded DNA is melted and the primer is allowed to bind to initiate extension is described in *Methods of Enzymology*; vol. 65, pp. 561–580 (1980). The RNA transcript binds only to the complementary strand of the dsDNA; thus it serves as a primer only for this strand. Another method to make hybrid polynucleotides by using the RNA copies as primers is to run two separate extension reactions where both the longest RNA copy of a given restriction fragment and the longest RNA copy of the complementary restriction fragment are added to a reaction mixture containing single stranded parent in one reaction and the complementary single strand in another reaction. Only the appropriately complementary RNA copy serves as a primer for the extension reaction because it will bind to the single stranded template whereas the complementary RNA copy will not. However, the complementary RNA copies may bind to each other and a method by which the double stranded RNA is melted and the appropriate primer is allowed to bind so that extension is initiated only from this primer is described in *Methods of Enzymology*; Vol. 65, pp. 561–580 (1980).

If the noncomplementary RNA copy interferes with subsequent steps, then it can be selectively removed following the above procedure by hydrolysis with a 3' to 5' exonuclease that requires a 3' OH. Venom exonuclease digestion can be performed as described by Tu and Wu, *Methods of Enzymology*; vol. 65, pp. 620–638.

Step IV: Separation of Polynucleotides

The extended primers are separated. The approximate range of the number of hybrids made from each RNA primer is between 200 and 400 and the approximate length of any given hybrid is less than 400 nucleotides. The preferred method of separation is gel electrophoresis as described in *Methods of Enzymology*, vol. 65, pp. 573-575 1980). Other methods of separation are described in Maniatis, pp. 173-185 and in *Methods of Enzymology*, vol. 65, pp. 542-545 (1980).

The fractions can be electroeluted, monitored by mass spectrometry, and collected as described in the Automating the Method Section. Separated fractions can also be collected from the gel on glass beads wells or anode wells of a carousel collector as described in the Electrophoresis Section. The glass bead collection procedure is a modification of Method II described by Vogelstein et al., *PNAS* 76, 615 (1979). Glass beads are present in the lower anode Well and electrophoresis buffer in this well contains saturated NaI as described in the above reference. Following collection, the polynucleotides adherent to the glass beads can be caused to undergo reaction to release formaldehyde which is recorded with a mass spectrometer and/or the polynucleotides are eluted from the glass beads by suspending them in a solution in the absence of NaI.

DNA or RNA bands collected as fractions can be monitored spectrophotometrically at wavelengths of 260 and 280 nm or by ethidium bromide fluorescent quantitation. See Maniatis, pp. 468-469; 163. The preferred method of ethiduim bromide fluorescent quantitation is to use ethidium bromide in the gel or in the anode well at a concentration of about 0.5 ug/ml. See Maniatis, p. 163. Also, it is not necessary to remove ethidium bromide from RNA or DNA to perform primed synthesis of Step III. (See *Methods of Enzymology*, vol. 65, p. 565 (1980)). If the mass labeled nucleotides contain in addition a radiolabel, then the bands can be monitored by a scintilation counter.

Step V: Mass Data Acquition

A portion of a selected purified polynucleotide (polynucleotides) sample(s) is (are) reserved for subsequent steps. The selection criteria is described in the Matrix Method of Analysis I Section.

Each purified polynucleotide sample is reacted to form 3' nucleotides or nucleosides which are further reacted to release labeled formaldehyde molecules from the 5' pentose position of each nucleotide or nucleoside. The released formaldehyde is analyzed with a mass spectrometer.

Step VI: 5' Randomization Procedure

The 5' end of the selected purified polynucleotide (polynucleotides) is (are) made random in length by removing ribonucleotides from the 5' end so that the products are molecules of one nucleotide less from the largest polynucleotide to the molecule containing only DNA or the dinucleotide containing one ribonucleotide and one dideoxyribonucleotide, for the case where the longest polynucleotide consists of RNA with a terminating dideoxynucleotide.

Method A: The 5' end of the hybrids contains RNA; therefore, they can be randomized by a 5' to 3'exoribonuclease. This can be accomplished for example by using yeast ribonuclease as described in *Enzymes*, Dixon and Webb, p. 852 (1979) and in Ohtaka, *J.B.C.* 54:324-327 (1963).

Method B: Reverse transcriptase possesses a polypeptide which selectively degrades the RNA of an RNA-DNA hybrid with a partially processive mechanism. See Maniatis, pp. 128-132 and Gerald, *Biochem.* 20:256-264 (1981).

A partially processive 5' to 3' exonuclease attacks a strand and removes a small number of nucleotides by a processive mechanism and then dissociates to attack a different strand. Thus, extent of hydrolysis at the 5' end at any polynucleotide is a random event. Therefore, the desired distribution of 5' randomized polynucleotides is obtained with this type of enzyme.

An RNAase HI or αB RNAase H reaction is run as described under RNAase H assays, Gerald, supra, with the exception that either appropriate single stranded template is added to the reaction mixture containing the polynucleotide to be 5' randomized, or double stranded parent is added. In the latter case, an annealing procedure is performed to allow separation of the double stranded template and to allow pairing of the polynucleotide with the complementary strand of the added DNA template. The annealing procedure is set forth in *Methods of Enzymology*, vol. 65, p. 567 (1980). The reaction is terminated after a time sufficient to generate a distribution of reaction products as described above. A graph of the extent of hydrolyis as a function of time appears in FIGS. 2 and 3 of Gerald, p. 260 (1981). These plots are indicative of the time length of the 5' randomization reaction. The concentration of the template, polynucleotide, and enzyme, and the times of reaction are adjusted to yield the desired distribution of products. The effect of manipulation of these variables on the products appears in Gerald, supra and in *DNA Synthesis in Vitro*, Wells and Inman, pp. 270-330 and in particular p. 300. Approximate values for these variables are as follows: 2.4 pmole of polynucleotide, 2.9 pmole of template, $10^{-3}$ unit of enzyme, in 1 ul volume run for about 5-20 mins. One advantage of using RNAase H and added template is that the problem of hydrolysis resistant hair pin loops is overcome.

Method C: The hybrid polynucleotides are 5' randomized using an endonuclease that randomly cleaves RNA and produces a 3' OH. The molecule cleaved from the 5' end is hydrolyzed with a processive 3' to 5' exoribonuclease that requires a 3' Ribonuclease can serve as the endoribonuclease. See *Enzymes*, Dixon and Webb, p. 856 (1979); Hiramuru *J.B.C.* 65:701 (1969). Venom exonuclease can serve as the 3' to 5' processive exonuclease that requires a 3' OH. The protocol is described in Tu and Wu, *Methods of Enzymology*, vol. 65, pp. 620-638 (1980).

Method D: 5' randomization can be accomplished by mild RNA hydrolysis designed to overcome the problem of hair pin loops. See *Methods of Enzymology*, vol. 65, pp. 667-669 (1980). This procedure produces single hits of the RNA and a mixture of 2' and 3' phosphates. The 2' or 3' phosphate can be removed to create a 2' and 3'OH. Then a 3' to 5' processive exonuclease that requires a 3'OH can be used to degrade the RNA polynucleotide which was hydrolyzed from the 5' end of the polynucleotide. The 2' or 3' phosphate can be hydrolyzed to an OH by alkaline phosphatase. See *Enzymes*, Dixon and Webb, p. 19; 840. The phosphatase procedure is described in Maniatis, pp. 133-134. Venom exonuclease can serve as the 3' to 5' progressive exonuclease which degrades the RNA polynucleotide which was hydrolyzed from the 5, end of the polynucleotide. The reaction is described in Tu and Wu, *Methods of Enzymology*, vol. 65, pp. 620-638 (1980).

The preferred methods are methods B and D.

Step VII: Separation of 5' Randomized Polynucleotides

The polynucleotides are separated by the procedures described in Step IV.

Step VIII: Second Mass Data Acquisition

Collected fractions are reacted to release labeled formaldehyde which is analyzed with a mass spectrometer as described in Step V.

Step IX: Data Analysis

Approximately 400 nucleotides are sequenced from this data using the procedure discussed under Matrix Method of Analysis I. The data from all the restriction fragments allows the sequence of the entire parent to be determined.

Alternative Modes of Carrying Out the Invention

These modes are based upon the second approach for preparing overlapping sequences. The form of the matrix method for solving the sequence with data from these polynucleotide generating strategies is discussed under Matrix Method of Analysis II.

The following procedure is done as a first step in all subsequent procedures described.

The first 40 or so nucleotides of parent DNA are sequenced. This can be done by replicating the template with mass labeled nucleotides and terminating with mass labeled dideoxyderivatives. The dideoxyderivative of each polynucleotide serves as the internal standard. The replication polynucleotides are separated and the base composition determined by mass spectroscopic analysis. The sequence is solved using the sequential subsets method. This is discussed under Method of Sequential Subsets, page 95.

A. Procedure I: Direct Transfer of Mass Labeled Replication Products

The template is replicated with random termination using deoxyribonucleotides and dideoxynucleotides that are each uniquely mass labeled at the 5th position of the pentose. The polynucleotides uniquely mass labeled at the 5th position of the pentose are reacted to release formaldehyde from this position which identifies each of the 4 different bases and the terminal base of each polynucleotide. The conditions of the polymerization reaction are controlled such that the products of reaction n+1 are on average longer than those of reaction n. For example, this can be accomplished by controlling the time at which dideoxynucleotides are added to the polymerization reaction mixture or the concentration of dideoxynucleotides in the reaction mixture can be made greater in reaction n than in reaction n+1. A portion of the products from reaction n is transferred to n+1 successively for each reaction, so that the 5' end of the reaction products of reaction n+1 are displaced from the template by those from reaction n. The displaced DNA is degraded with SI nuclease, an enzyme which specifically digests single stranded DNA. The polynucleotides are thus made random at the 5' as well as the 3' end. The short polynucleotides are isolated from the transferred fragments and from the remaining template by a method which separates by size and/or nucleotide. Samples are separated by ion exchange or gel filtration chromatography, HPLC, or polyacrylamide gel electrophoresis. The polynucleotides are reacted to liberate formaldehyde which is analyzed by mass spectrometry, and the sequence is determined by the Matrix Method of Analysis II.

B Procedure II: Mass Labeled DNA Primers and Unlabeled DNA or RNA Displacers

The DNA template blocked at the 3' end is partially replicated, starting at the 3' end of the template, using ribonucleotides and RNA polymerase such that the reaction products of reaction n+1 are on the average longer than the reaction products of reaction n. The replication reaction is terminated by denaturing the RNA polymerase enzyme. Polynucleotides of random length at their 3' end are produced. The polynucleotides are transferred from reaction n to reaction n+1 after removing the template from this aliquot and the transferred polynucleotides are allowed to anneal. The longer polynucleotides will anneal over or displace the shorter ones so that the resulting annealed parts are double stranded in length as great as the longest polynucleotides from both reactions and are random at the 3' end. S1 nuclease is used to degrade single stranded RNA and DNA so that only that part of the template that is annealed to RNA remains. The RNA is selectively and completely destroyed. This can be done with RNAase H or base hydrolysis. Two separate replication reactions are run using the remaining part of the template generated in previous reactions (the partial template). In one replication reaction an unlabeled RNA or DNA copy of the partial template is made. When a DNA copy is made, it is generated so that it possesses a 5' hydroxyl.

In another separate reaction a mass labeled copy of the partial template is made. The unlabeled DNA or RNA products from the former reaction are called displacers and the mass labeled DNA products from the latter reaction are called primers. The primers are extended on the original template using mass labeled deoxynucleotides and mass labeled dideoxynucleotides which terminate the replication reaction randomly. The displacer polynucleotides are added to the products of this reaction under conditions which favor the displacement from the template of the 5' end of the extended primers by the displacers. The reaction is incubated with S1 nuclease which destroys single stranded DNA, but not double stranded DNA or double stranded DNA/RNA hybrids and produces 5' nucleotides (i.e. leaves a 5' phosphate). An S1 nuclease digestion may have to be done prior to transferring the displacer. This will prevent the chance annealing of the displacers or displaced fragments to the template 3' to the replication polynucleotides. Thus, the displaced part that is single stranded is selectively degraded and the remaining part that is not degraded possesses a 5' phosphate. The polynucleotides are allowed to denature following inactivation of S1 nuclease.

Next, if DNA displacers are used, the reaction products are incubated with spleen phosphodiesterase. The DNA displacers which contain a 5' OH are selectively degraded because spleen phosphodiesterase degrades RNA or DNA completely and requires a 5' hydroxy terminus. The remaining part of the extended primer is not degraded because it contains a 5' phosphate group.

When RNA displacers are used, then the RNA can be removed completely and selectively by base hydrolysis or by hydrolysis with the enzyme RNAase H.

The labeled polynucleotides are separated by ion exchange chromatography, HPLC, or gel electrophorosis and then reacted to release formaldehyde which is analyzed by mass spectrometry. The base composition and terminal base identity is determined so that the sequence can be solved using the Matrix Method of Analysis II.

C. Procedure III: RNA Primers; RNAase H or Base Hydrolysis

Partial DNA templates are made following the procedure described under procedure II. A complementary RNA copy of the partial DNA templates that vary in length at the 3' end are made by a replication reaction of the partial templates. The RNA replication products are isolated and used as primers in a DNA extension reaction. The primers are extended in mass-labeled DNA. Mass labeled deoxyribonucleotides are used during replication and competing mass labeled dideoxynucleotides are used to terminate the replication reaction. The RNA is completely and selectively digested with RNAase H for example or by base hydrolysis. The DNA polynucleotides are purified; they are random on the 5' end because the primers were 3' random, and they are random on the 3' end because replication was terminated randomly. Furthermore, by the nature of replication the condition $X_n -- X_1$ is satisfied by all of these polynucleotides. Thus, the polynucleotides conform to the criteria of strategy II; therefore, data can be obtained by mass spectrometry of the formaldehyde released from the polynucleotides and the sequence can be solved for using the Matrix Method of Analysis II.

D. Procedure IV: Direct Precipitation

Figure 3:
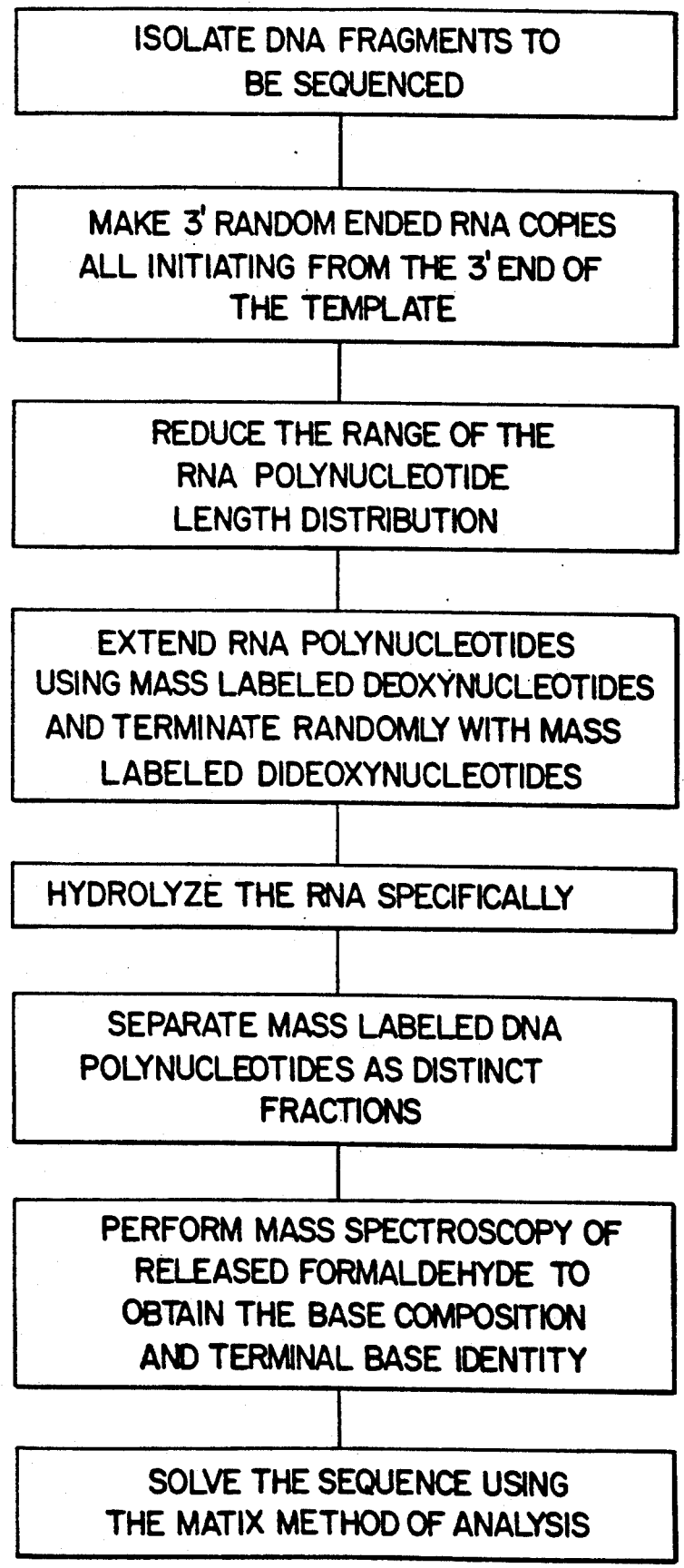
FIG. 3 is a flow chart of the steps of Procedures IV and V of Alternative Modes of Carrying Out the Invention.

An outline of Procedures IV and V are shown schematically in FIG. 3.

The template is partially replicated starting at the 3' end of the template using ribonucleotides and RNA polymerase such that the replication products of reaction n+1 are on the average longer than the reaction products of reaction n. The replication reaction is terminated by denaturing the RNA polymerase enzyme or by a precipitation reaction as follows.

The reaction mixture is titrated with a cation, for example calcium which will precipitate the RNA replication products and the template such that the large polynucleotides are precipitated preferentially over the smaller polynucleotides. The cation concentration, which will precipitate the desired length of polynucleotide while allowing the polynucleotides shorter than this length to remain in solution can be determined experimentally and this predetermined concentration is the end point of the precipitation reaction. It can be monitored with an ion selective electrode for example, or the precipitation reaction can be monitored via light scattering. The small RNA products remaining in solution are removed.

Next, the precipitate is resolubilized and any excess cation is removed by an exchange reaction with another anion where the cation and anion have a much lower $K_{sp}$, solubility constant, than that of the cation and the nucleic acid. The cation can also be removed with a chelating agent. The RNA replication products are used as primers for mass labeled DNA replication. Mass labeled deoxynucleotides are used during replication, and competing mass labeled dideoxynucleotides are used to terminate the replication reaction. Following DNA replication, the RNA part of the hybrid molecules is selectively and completely destroyed. The RNA can be degraded selectively with RNAase H or by base hydrolysis. The resulting DNA polynucleotides which are now random at the 3' and 5' ends are purified by the methods of HPLC, ion exchange chromatography or polyacrylamide gel electrophoresis (see electrophoresis instrumentation). The polynucleotides are reacted to release formaldehyde which is analyzed by mass spectrometry to determine the base composition and terminal base. The sequence is solved by using the Matrix Method of Analysis II.

E. Procedure V: Precipitation After Transfer.

The procedure is the same as for procedure IV, except that the replication products of any given reaction are transferred to the succeeding reaction as part of the method to eliminate small replication polynucleotides.

The template is partially replicated starting at the 3' end using ribonucleotides and RNA polymerase such that the replication products of reaction n+1 are on the average longer than the reaction products of reaction n. The replication reaction is terminated by denaturing the RNA polymerase enzyme.

RNA polynucleotides from reaction n are transferred to reaction n+1 to displace short polynucleotides with the longer polynucleotides of the distribution produced in this reaction; the smaller polynucleotides are then in solution unbound to the large template. A precipitation reaction is carried out to preferentially precipitate the hybridized complexes leaving the small fragments in solution. The precipitate is resolubilized and the replication is resumed in DNA with mass labeled substrate. Mass labeled deoxynucleotides in the presence of mass labeled dideoxyterminators, respectively are used. The RNA is selectively and completely destroyed with RNAase H or base hydrolysis. Following purification of the polynucleotides by polyacrylamide gel electrophoresis, ion exchange chromatography, or HPLC, and following mass spectropscopic analysis of released formaldehyde, the polynucleotides are sequenced by the Matrix Method of Analysis II.

Detailed Methods of Alternative Modes (Methods II)

The following protocols are examples of specific methods to implement the steps outlined in the above Alternative Modes of Carrying Out the Invention.

A. Isolation of Parent to be Sequenced

The parent molecule to be sequence can be isolated by the methodologies discussed earlier under Methods I. Restriction fragments with length on the order of $10^5$ nucleotides are isolated in the present case. Furthermore, a useful method is that of Schwartz and Cantor, *Cell* 37:67-75 (1984) of pulse-field gradient electrophoresis. This technique, which is based on the application of alternating, perpendicular inhomogeneous electric fields to a standard horizontal agarose gel, is capable of resolving DNA fragments of up to 5000 Kb. It has already been applied to the separation of intact DNA strands from yeast chromosomes. This method can be used preparatively to purify very large restriction fragments (200 to 5000 Kb) produced from a digest with enzymes which cut infrequently in human DNA. These purified fragments could then be digested directly with a second, different restriction enzyme and these products cloned in an appropriate vector or DNA fragments of an approximate length of several hundred Kb can be expanded in yeast artifical chromosomes as described by Burke, et al., *Science* 236:806-812 (1987) prior to a second digest and cloning step. The resulting library would have a low complexity and consist solely of sequences contiguous in the human genome.

B. Primary DNA Copies

DNA copies of the template can be made by first adding a 3' polynucleotide tail to the template with terminal nucleotide transferase. The method is described in Maniatis, p. 148; pp. 239-240. A DNA primer complementary to the polynucleotide tail is added and extended by the DNA polymerization protocol described in Primings, DNA Sequence Analysis by Primed Synthesis, *Methods of Enzymology*, vol. 65, pp. 561-580. The procedure is also described by Sanger, *J. of Molec. Bio.* (1975) 94: 441-448. In either case, the reaction is performed in the absence of dideoxy terminating nucleotides. And polymerization is terminated by other means such as denaturing the enzyme by heat.

Mass labeled nucleotides are used when appropriate as described in Alternative Modes of Carrying Out the Invention. For the procedures which require a DNA replication product with a 5 OH, a primer containing a 5' OH that is also complementary to the polynucleotide tail is used.

C. Primary RNA Copies

RNA copies of the template which all initiate from the same point at the 3' end of the template can be made by ligating the template to an efficient bacteriophage promotor, for example SP6. SP6 is a Salmonella phage that encodes an RNA polymerase specific for SP6 promoters (Butler and Chamberlin, *J. Biol. Chem.* 257, 1982, 5772-5778.) One advantage of this in vitro transcription system is that SP6 RNA polymerase initiates transcription exclusively at the SP6 promoter, thus avoiding transcripts that initiate elsewhere. In addition, it is possible to obtain long transcripts and SP6 RNA polymerase is relatively easy to purify in large amounts and is remarkably stable.

SP6 can be ligated to the template in the correct orientation by starting with a double stranded DNA molecule of SP6, ligating a linker to SP6 and then ligating the linker to the double stranded restriction fragment of which one strand serves as the template in subsequent sequencing reactions.

Blunt end cDNA copies of SP6 can be generated by incubating SP6 cDNA with protruding ends with bacteriophase $T_4$ DNA polymerase or *E. Coli* DNA polymerase I. These are enzymes that remove protruding 3' single stranded termini with their 3' to 5' exonuclease activities and fill in recessed 3' ends with their polymerizing activities. These reactions are described in Maniatis, p. 243. The combination of these activities generates blunt ended cDNA molecules, which are incubated with a large excess of linker molecules in the presence of bacteria phase $T_4$ DNA ligase, an enzyme that is able to catalyze the ligation of blunt ended DNA molecules. The products of the reactions are cDNA molecules carrying polymeric linker sequences at one of their ends. These molecules are then cleaved with the appropriate restriction enzyme and ligated with the restriction fragment that has been cleaved with a compatable enzyme, one that creates ends which are complementary to those created by the former enzyme. This method as well as others are discussed in Maniatis, pp. 219-220.

Most linkers are supplied by the manufacturer with 5' hydroxyl ends. Because $T_4$ DNA ligase requires 5' phosphate ends, it is necessary to phosphorylate the linkers before they can be joined to DNA. The kinase and ligase reactions can be carried out sequentially in the same reaction mixture. $T_4$ polynucleotide kinase can be used to phosphorylate the 5' termini of the synthetic linkers prior to ligation. The method is described in Maniatis, pp. 125-126; 394-395. The attachment of synthetic linkers is described in Maniatis, pp. 396-397.

SP6 with the appropriate sticky ends can be ligated to the restriction fragment by methods described in Maniatis, pp. 396-397, where the linkers are molecules of SP6 promoter attached to a linker with sticky ends for the restriction fragments. Sticky ends refers to uneven ends that are created by the endonuclease activity of the restriction enzyme. Complementary ends are produced between two molecules that are cleaved by the same enzyme. Also, SP6 can be bluntly ligated to the restriction fragment by methods described in Maniatis, pp. 396-397, where SP6 is ligated directly to the restriction fragments. Alternatively SP6 can be ligated to the linker to form a hybrid SP6-linker molecule which can be linked to the restriction fragment. The restriction fragment can also be cloned into a vector that contains the SP6 promoter. This method is described for the PBR322 plasmid in Green, Maniatis, Melton, *Cell*, 32:621-694 (1983).

The procedure for splicing a restriction polynucleotide into a vector and amplifying the product is described in Maniatis, pp. 51-54; 270-307, and *Methods of Enzymology*, vol. 101, 1983, pp. 3-123.

RNA transcription is carried out with the SP6 promoter system as described in Green et al. *Cell* (1983), with the modification that the ribonucleotides are not radiolabeled. When a vector system is used, the template is linearized by restriction fragment digestion, (See Green et al., supra, p. 682).

Another method for making an RNA copy of the template initiated only from the 5' end is to first add a polynucleotide tail to the 3' end of the template as described in Method IIB. The complementary RNA primer is added, and the RNA primer is extended with ribonucleotide triphosphates using DNA polymerase in the presence of $Mn^{2+}$. The polymerization reaction with $Mn^{2+}$ is described in *Methods of Enzymology*, vol. 65, p. 572. The procedure is followed as described in *Methods of Enzymology*, pp. 561-580 except that ribonucleotides are substituted for deoxynucleotides, the reaction is run without dideoxynucleotides, $Mn^{2+}$ is substituted for $Mg^{2+}$, and the reaction is terminated by denaturing the enzyme or by the addition of EDTA.

D. Removal of Template Before the Transfer of an Aliquot from Reaction n to Reaction n+1

The DNA template can be selectively destroyed in those cases where RNA copies are transferred from reaction n to n+1 by the following procedure. Incubate the aliquot to be transferred with 20 ug of DNAase I for 20 minutes. The enzyme is then inactivated by the addition of acid, for example. The solution is neutralized by the same equivalent of base.

The template can also be removed by gel electrophoresis as described in Method I or gel or DEAE chromatography. DEAE chromatographic techniques are described in *Cloning, A Laboratory Manual*, Maniatis, p. 130, p. 166. Gel chromatography is described in Maniatis pp. 464-465, where the reaction buffer is substituted for the equilibration buffer and the size range of the gel used is appropriate for the separation of the polymerization products from the template.

For procedure I a 3' to 5' exonuclease could be used to degrade the template, since the replicated fragments contain a dideoxynucleotide at the 3' end and are resistant to degradation. The method is described below under 3' to 5' digest which requires a 3' OH.

E. Hybridization Methods

Procedures described in Alternative Modes of Carrying Out the Invention contain one or more steps which depend on competitive displacement of all or a part of one polymerization product by another. In some cases, displacement can be accomplished where it is thermodynamically unfavorable by increasing the concentration of the competing strand. Methods describing the competitive binding of short DNA polynucleotides to DNA templates, thus, partially displacing large DNA polynucleotides by this mechanism are discussed in *Methods of Enzymology*, vol. 65, 1980, p. 567. The equivalent procedure that involves the hybridization of small polynucleotides of RNA is described in Hozumi, Tonegawa, *PNAS* 73 (10) 3628-3632 (1976).

For cases involving the total displacement of short RNA or DNA polynucleotides by long polynucleotides of RNA or DNA, respectively, the reaction is thermodynamically favorable; therefore, the reaction is carried out as described for the respective unfavorable reaction where the reaction concentrations of the small polynucleotides is not increased. Furthermore, RNA can hybridize to double stranded DNA in the presence of 70% formamide by displacing the identical DNA strand. This reaction probably occurs because of the greater thermodynamic stability of the RNA/DNA hybrid when it is near the denaturation temperature of duplex DNA. Thus, an RNA strand can favorably displace a complementary DNA strand which is all or part of the length of the template. The procedure is described in Thomas, White, Davis, *PNAS* 73 (7) 2294 1976). Also, see *Methods of Enzymology*, vol. 65, 1980, pp. 718-749.

F. 3' to 5' Digest with the Requirement of a 3' OH

DNA can be digested in the 3' to 5' direction by T4 exonuclease. T4 exonuclease degrades single stranded or double stranded DNA completely to 5' mononucleotides and requires a 3' hydroxyl. See Kornberg, *DNA Replication*, p. 321 and Maniatis, p. 118. The reaction procedure is described in Maniatis, pp. 117-120. The reaction is carried out as described in the absence of the four dNTp's.

Also, venom exonuclease can serve as the 3' to 5' processive exonuclease that requires a 3' hydroxyl. The enzyme releases 5' mononucleotides and degrades single stranded RNA and DNA completely (see Kornberg, *DNA Replication* p. 321 and Dixon, *Enzymes* p. 852.) The procedure is described in TU, WU, *Methods of Enzymology*, vol. 65, pp. 625-627.

G. 5' to 3' Digest that Requires a 5' OH

Spleen phosphodiesterase requires a 5' hydroxyl terminus and releases 3' mononucleotides and degrades single stranded RNA and DNA completely (Kornberg, *DNA Replication*, p. 321 and Dixon, *Enzymes*, p. 852.) The reaction protocol is described by Tu and Wu, *Methods of Enzymology*, p. 627.

H. Hydrolysis of Single Stranded DNA without Hydrolysis of Double Stranded DNA S1 nuclease degrades single stranded RNA or DNA to yield 5' phosphoryl mono or oligonucleotides. Double stranded DNA, doubled stranded RNA and DNA/RNA hybrids are resistant, Maniatis, p. 140). The procedure followed to selectively degrade single stranded RNA or DNA to leave a 5' phosphate is described in Favaloro, Treisman, Kamen, *Methods of Enzymology*, vol. 65, 1980, pp. 718-749. In particular, see pp. 729-730.

I. Extension of Primers

DNA or RNA primers may be extended with mass labeled deoxnucleotides and terminated with mass labeled dideoxynucleotides as follows. An RNA or DNA primer is extended on single stranded template with mass labeled deoxynucleotides and terminated randomly with mass labeled dideoxynucleotides. The procedure is described under Primings, Smith, DNA Sequence Analysis by Primed Synthesis, *Methods of Enzymology*, vol. 65, 1980, pp. 561-580. The procedure is also described in Sanger, *Journal of Molecular Biology*, 1975, 94, pp. 441-448. Mass labeled deoxy and dideoxynucleotides are used and the A, T, C, and G reactions are performed as a single reaction with final reactant concentrations as described in the article by Smith, supra. DNA polymerase I will initiate DNA synthesis at an RNA primer (see Kornberg, *DNA Replication*, p. 151; Lee Huang, Cavalier, *Proceedings of the National Academy of Science*, 511, 1022-1028, (1964), Stryer, *Biochemistry*, p. 576). $Mn^{2+}$ may be substituted for $Mg^{2+}$ if DNA extension at the RNA primer occurs with low efficiency (See Kornberg, p. 151; Smith, *Methods of Enzymology*, vol. 65, p. 572.)

DNA primers are extended in RNA by using mass labeled ribonucleotides; the procedure is described in *Methods of Enzymology*, vol. 65, p. 497-499. The RNA extension is terminated randomly by carrying out the reaction in the presence of mass labeled dideoxynucleotides and DNA polymerase I.

J. The Selective Degradation of RNA

RNA can be selectively degraded completely by base hydrolysis. The procedure is described in *Methods of Enzymology*, vol. 65, p. 572. Also, the RNA could be degraded selectively by exoribonuclease H, RNAase H, which catalyzes the exonucleolytic cleavage of the RNA of RNA/DNA hybrids to 5' phosphomonoesters in the 5' to 3' direction. The procedure is carried out as described in Methods I - Method B except that the reaction is allowed to go to completion.

K. Separation of Fragments

Separation of polynucleotides by electrophoresis and/or HPLC is described in Methods I and under Electrophoresis Instrumentation.

Matrix Method of Analysis I

In reference to Methods I, two procedures of producing RNA copies of the single stranded restriction fragments are described. See pages 53-54. Procedure A involves using primed RNA synthesis; Procedure B involves using RNA polymerase under conditions that allow the enzyme to initiate RNA polymerization randomly on a DNA template with high activity. Both methods may give rise to subsets that have a common 5' end. In this case the simple strategy described below is used to solve for the sequence from the data. But, the replication products may not all have a common 5' end; therefore, the data must be treated as if subsets are made from the loss of nucleotides randomly from the 3' and 5' end of the largest polynucleotide and the matrix method of analysis must be used as described in this discussion.

A single RNA copy of the restriction fragment is desired. The RNA copy's length must be greater than half the length of the restriction fragment or it must be at least 20 base pairs in length and be a copy of a portion of the 5' one half of the restriction fragment. The latter condition eliminates the possibility that the copy will bind elsewhere in the template by random probability and the former condition insures that enough of the 5' end will be sequenced to complement the sequence determined for the antiparallel strand, so that the entire fragment and adjoining overlap region with the next restriction fragment is sequenced. If one pure polynucleotide is isolated from either RNA copy procedure with subsequent steps carried out as described in Method I and composition and terminal base identity data obtained, then the sequence is solved for, by taking sequential subsets from the first determination of the composition and terminal base identity described in Methods I, where the change from a polynucleotide to one with the same composition but one nucleotide less 45° initiation line. As described below, what is unique to the designated longest polynucleotide of the first rectangular matrix is that all of the "knowns" are guessed where the "knowns" make up the nucleotide sequence of the 5' one half of the polynucleotide relative to the "axis" which is in the middle of the polynucleotide. Also, these "knowns" represent the sequence that is complementary to the parent and superimposes more 3' on the parent than any other "knowns" in the configuration. To use the matrix method of Analysis I to get a unique solution, the RNA copies (if more than one exists) must overlap each other by at least one nucleotide. This is inferred in the solution. By using the preferred method, polynucleotides which are 5' randomized must be chosen so that their length is greater than that of the polynucleotide represented at the matrix position (1,½m) in the first rectangular matrix generated from the 1st designated longest polynucleotide as previously described. And, polynucleotides 5' randomized must contain different 3' terminal nucleotides. Also, the smallest hybrid polynucleotides must be 5' randomized.

|   |   |   |   | $GTACX_1X_2X_3X_4$ | $GTACX_1X_2X_3$ | $GTACX_1X_2$ | $GTACX_1$ |
|---|---|---|---|---|---|---|---|
|   |   |   | $TACX_1X_2X_3X_4X_5$ | $TACX_1X_2X_3X_4$ | $TACX_1X_2X_3$ | $TACX_1X_2$ | $TACX_1$ |
|   |   | $ACX_1-X_6$ | $ACX_1X_2X_3X_4X_5$ | $ACX_1X_2X_3X_4$ | $ACX_1X_2X_3$ | $ACX_1X_2$ | $ACX_1$ |
|   | $CX_1-X_7$ | $CX_1-X_6$ | $CX_1X_2X_3X_4X_5$ | $CX_1X_2X_3X_4$ | $CX_1X_2X_3$ | $CX_1X_2$ | $CX_1$ |
| $X_1-X_8$ | $X_1-X_7$ | $X_1-X_6$ | $X_1X_2X_3X_4X_5$ | $X_1X_2X_3X_4$ | $X_1X_2X_3$ | $X_1X_2$ | $X_1$ |

Example of matrix used to solve the sequence if more than one RNA copy of the restriction fragment is isolated. The first rectangular matrix is solved first then that information is used to move along 45° initiation line and solve for more of the complement to the parent sequence.

in each case assigns the lost nucleotide successively in order from the 3' to the 5' direction. Second, using sequential subsets from the composition and terminal base identity data from the second determination following the 5' randomization procedure described in Methods I, a gain of a nucleotide from the smallest to the largest polynucleotide assigns those nucleotides successively in order in the 3' to 5' direction.

If more than one RNA copy of the restriction fragment is isolated, then the Matrix Method of Analysis must be used because using the previous procedure on more than one polynucleotide and overlapping the sequences may result in more than one solution due to interchange of assignment between polynucleotides and/or shifting of the overlap region of the polynucleotides. For example, when any given polynucleotides have the same base pair composition and terminal base, then their identity is lost. That is, it is impossible to distinguish which base was gained by which polynucleotide of the next step in the progression.

The matrix used to solve sequences by the Matrix Method of Analysis I is a form which consists of a series of rectangular matrices where the (1,1) positions of all of the matrices are aligned such that they form a "45° line" and all of the matrices at least partially overlap each other. This line is called the "45° initiation line" and all of the polynucleotides which abut this line can serve as the longest designated polynucleotide at position (1,1) to define a rectangular matrix for implementing the matrix method as was previously described. The rules described previously apply to the entire configuration or to any rectangular matrix which is a part of the entire configuration. That is, that bases are lost from the 5' end down any column and bases are lost from the 3' end across any row. The first rectangular matrix contains more rows and fewer columns than any other rectangular matrix with a different designated longest polynucleotide at the designated position (1,1) along the In general, polynucleotides are chosen for randomization so that a unique solution can be obtained when the sequential subsets are guessed to be proper and the "knowns" are guessed being that sequence 5' to the axis is not known extrinsically. The "knowns" are the nucleotides which represent the sequence 5' to the "axis" of the first designated longest polynucleotide of the first rectangular matrix. And, a solution of this matrix is attempted by using the data to find from/to moves from coordinate position, (1,1), to (½M+1, ½M) and to/from moves to (1,1) from (½M+1, ½M) in the absence of any contradictions, as was described previously. If no contradiction arises and the stated rules of randomization are followed, then the sequence is assigned uniquely for the preferred method except in the case where the smallest polynucleotides 5' randomized contain the same terminal nucleotide. In this case, the ability to find sequential subsets which allow from/to steps down any column, except the last column, in the solved matrix, in the absence of any contradiction will verify the sequence. In the solved matrix the variables are replaced by the appropriate nucleotides.

Once the 3' end of the sequence, the "unknown" sequence, is solved for in the first rectangular matrix, then this information can be used to assign "known" nucleotides 5' of the new "axis" which is in the middle of the next designated longest polynucleotide along the 45. initiation line. Sequential subsets are guessed as being proper and a solution is attempted. If no set can be found which solves the sequence using this new designated longest polynucleotide, then the next polynucleotide moving along the 45° initiation line is designated the longest polynucleotide and the solution is reattempted. This is repeated until all the polynucleotides along the 45° line are exhausted. In general, the solution process consists of moving along the 45° initiation line from upper right to lower left and finding proper sequential subsets that result in the solution of the rectangular matrix from an initiation point along this line to the coordinate position (½M+1, ½M) where (½M+1,M) is the position assigned relative to the first rectangular matrix of the configuration matrix and back to position (1,1) without giving rise to a contradiction. Movement along the 45° initiation line will solve for more of the sequence in the 3' direction of the complementary sequence of the parent.

In the case of more than one RNA copy, separation by size may yield mass data of mixtures of polynucleotides. However, this data can be solved to yield the composition and terminal nucleotide of the component polynucleotides by solving multiple equations in multiple unknowns. Consider an example where 3 RNA copies are isolated, extended in DNA and separated by size where each band contains 3 polynucleotides of different composition but the polynucleotides in each band are the same length. If one of the bands which contains 3 polynucleotides is 5' randomized, then each band resulting from the separation by size of this population may contain 3 polynucleotides each, except for the last 3 bands (which will contain 3, 2, and 1 polynucleotide respectively.) The mass data yields 8 equations, 4 from the signal due to A, T, G and C in any polynucleotide and 4 due to A,T,G and C terminal bases. If a band contains 3 polynucleotides, then the relative amounts of each polynucleotide is unknown; this represents three unknowns. The last band contains only one base, the terminal. For the next to the last band 2 polynucleotides exist, one in proportion x and the other in proportion y where X and Y are variables. The one polynucleotide contains the same terminal but gains a 5' nucleotide, N, the second contains the same base as present in band 1 in the 5' position, but gains a terminal, T. Therefore, there are eight equations and four unknowns. The same reasoning applies to the three polynucleotides containing 3 bases. In successive bands each polynucleotide gains a nucleotide 5' to the existing nucleotides and these 3 bases represent 3 unknowns and the relative proportions of each polynucleotide represents 3 additional unknowns; therefore, there are 8 equations and 6 unknowns. At the limit, the 8 equations can be solved simultaneously to produce the composition and terminal base data for 4 polynucleotides in each band. This represents a capability which will not be exceeded during implementation of the preferred method.

FIG. 4 shows the matrix used to solve the sequence G A C T A C G A T G C C T A G T G C T.

The following fragments shown in FIG. 4 are 5' Randomized #6, #15, #18, #26. The data from this procedure is shown below.

| Polynucleotide (RNA underlined) | Composition | Δ | Terminal |
|---|---|---|---|
| #6 | | | |
| 6 GACTACGATGCCTA | 4A3G3T4C | G | A |
| 27 ACTACGATGCCTA | 4A2G3T4C | A | A |
| 28 CTACGATGCCTA | 3A2G3T4C | C | A |
| 29 TACGATGCCTA | 3A2G3T3C | T | A |
| 30 ACGATGCCTA | 3A2G2T3C | | A |
| #15 | | | |
| 15 GACTA | 2A1G1T1C | G | A |
| 31 ACTA | 2A1T1C | A | A |
| 32 CTA | 1A1T1C | C | A |
| 33 TA | 1T1A | | A |
| #18 | | | |

| Polynucleotide (RNA underlined) | Composition | Δ | Terminal |
|---|---|---|---|
| 18 TACGATGCCTAGTG | 3A4G4T3C | T | G |
| 34 ACGATGCCTAGTG | 3A4G3T3C | A | G |
| 35 CGATGCCTAGTG | 2A4G3T3C | C | G |
| 36 GATGCCTAGTG | 2A4G3T2C | G | G |
| 37 ATGCCTAGTG | 2A3G3T2C | A | G |
| 38 TGCCTAGTG | 1A3G3T2C | | G |
| #26 | | | |
| 26 TACGAT | 2A1G2T1C | T | T |
| 39 ACGAT | 2A1G1T1C | A | T |
| 40 CGAT | 1A1G1T1C | C | T |
| 41 GAT | 1A1G1T | G | T |
| 42 AT | 1A1T | | T |

Figure 5:
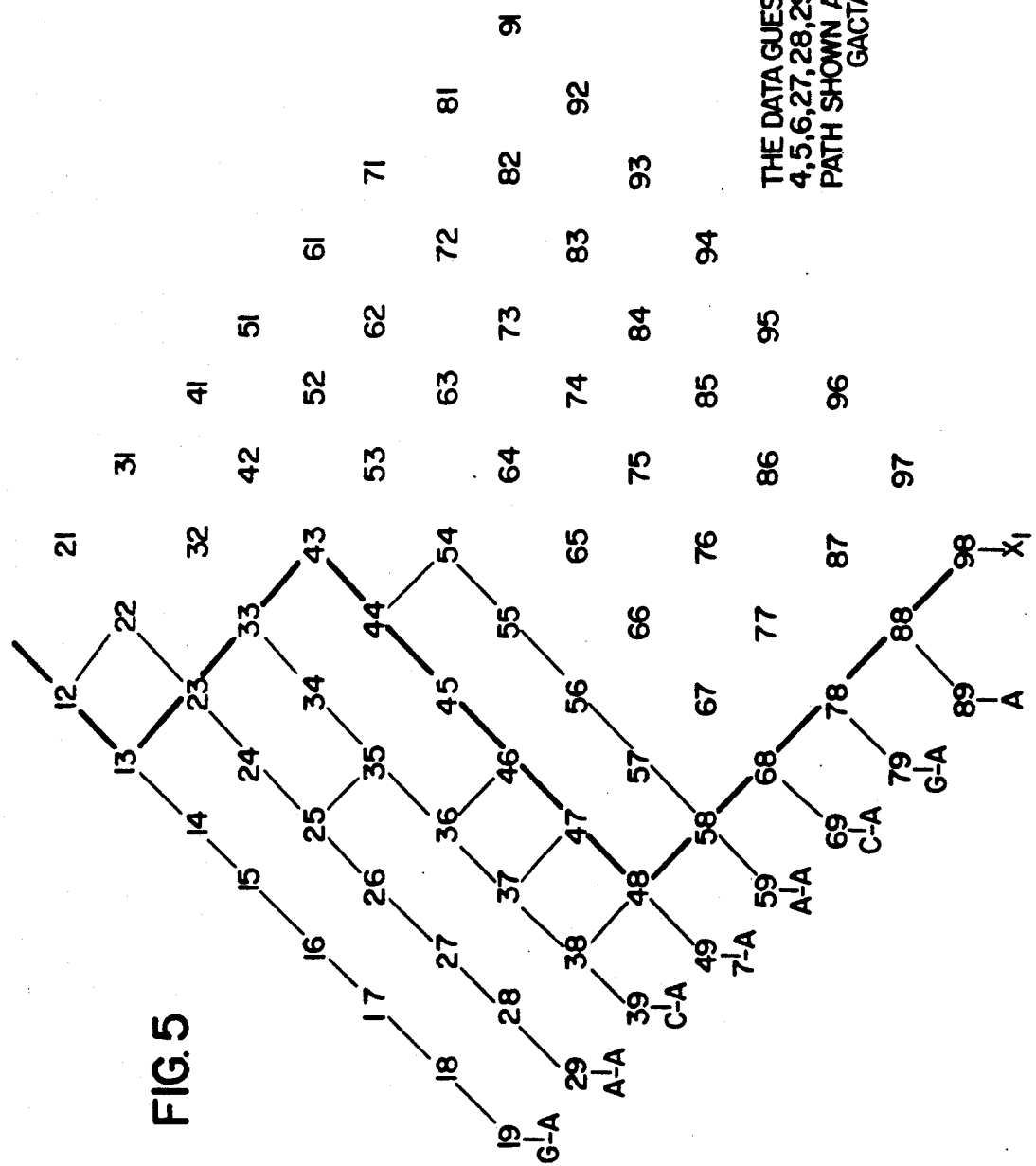
FIG. 5 is a lattice used to solve the first rectangular matrix of FIG. 4.
Figure 6:
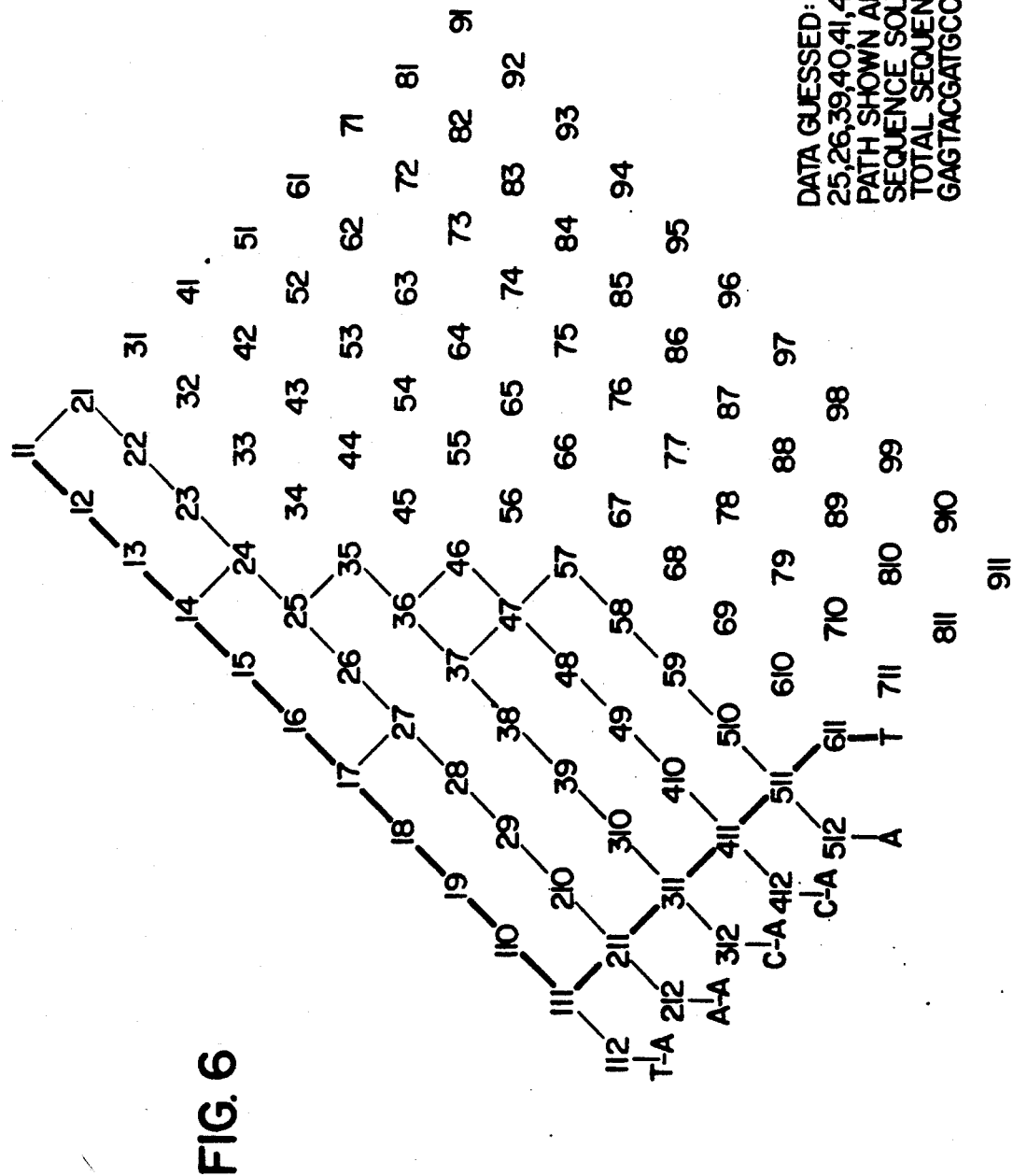
FIG. 6 is a lattice used to solve the fourth rectangular matrix of FIG. 4.

The connected coordinate positions in the lattices shown in FIGS. 5 and 6 represent all possible from/to moves consistent with the change in composition data. The heavy lines represent the to/from moves consist with the terminal base and change in terminal base data as verified in the matrix.

Matrix Method of Analysis II

For families of molecules generated by the second approach to overlapping sequences, the 5' portion of the molecule is known extrinsically. The reason is that 5' portion of the sequence of any family of polynucleotides corresponds to the 3' portion of the family of polynucleotides generated, from the adjoining segment of DNA. This is the region of overlap. Thus, when the entire sequence for any polynucleotide family is solved, the 5' end of the downstream set of polynucleotides is solved concomitantly. Thus, the letters $K_1$, $K_2$, $K_3$, $K_4$ ... represent the "known" sequence and $X_1$, $X_2$, $X_3$, $X_4$ ... represent the "unknown" portion of the sequence to be solved. This means that the sequence of any DNA strand can be solved sequentially by moving along the strand in the 5' to 3' direction. As the sequence of one polynucleotide family is deciphered, the 5' portion of the adjoining family is obtained and so on. This, of course, does not apply to the first polynucleotide family sequenced.

However, there are several strategies for determining the sequence of initial polynucleotide family. (See Sequential Subsets Method). Furthermore, it was demonstrated in the Examples of Solving Sequences by the Matrix Method of Analysis that the set of polynucleotides generated for analysis could contain the 5' known      unknown 3'

$K_5K_4K_3K_2K_1/X_1X_2X_3X_4...$ preceeding "known" in the 5' direction only if it contained the succeeding "knowns". For example, $K_4$ could only be present if $K_3 - K_1$ were also present in any polynucleotide. Also it was discussed under Strategy I that any succeeding "unknown" can be present only if all the preceeding "unknowns" were present in the polynucleotide up to the "axis" dividing "knowns" from "unknowns". This condition must be rigidly adhered to; however, the Matrix Method of Analysis can be used to solve uniquely a set of polynucleotides which do not conform rigorously to the first condition; that is, all possible polynucleotides of the "knowns" may be present in the set analyzed.

The solution follows the same procedure as before, except that the polynucleotides of the "known" type which contain base pairs lost in 3' to 5' direction relative to the 'axis' are recorded in the product matrix at the proper position.

The "known" type refers to polynucleotides in the matrix which do not contain variables. Those polynucleotides are recorded in the lattice at the level and position appropriate for the corresponding matrix coordinate position.

An exemplary matrix is shown below for polynucleotides which conforms to the criteria set forth for strategy II. For a designated longest polynucleotide which contains a total of eight (8) nucleotides, the matrix is made of 5 rows and 8 columns.

```
                              K4 K3 K2 K1 X1 X2 X3 X4
K4K3K2K1X1X2X3X4   K4K3K2K1X1X2X3   K4K3K2K1X1X2   K4K3K2K1X1
K3K2K1X1X2X3X4     K3K2K1X1X2X3     K3K2K1X1X2     K3K2K1X1
K2K1X1X2X3X4       K2K1X1X2X3       K2K1X1X2       K2K1X1
K1X1X2X3X4         K1X1X2X3         K1X1X2         K1X1
X1X2X3X4           X1X2X3           X1X2           X1
```

An exemplary lattice is shown below for polynucleotides which conform to the criteria set forth for strategy II. The matrix coordinate positions corresponding to polynucleotides of the "known" type are indicated.

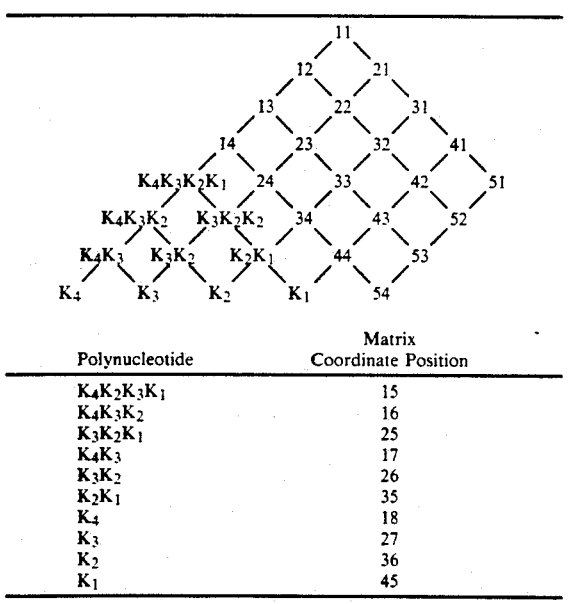

| Polynucleotide | Matrix Coordinate Position |
|---|---|
| K4K2K3K1 | 15 |
| K4K3K2 | 16 |
| K3K2K1 | 25 |
| K4K3 | 17 |
| K3K2 | 26 |
| K2K1 | 35 |
| K4 | 18 |
| K3 | 27 |
| K2 | 36 |
| K1 | 45 |

Furthermore, up to this point it was assumed that there is a "known" half and an "unknown" half to the DNA polynucleotide which is being sequenced in the n+1th reaction, and it is a portion of the overall piece being sequenced. One approach to a solution is to choose the correct "known" part and to set up the corresponding matrix and lattice. Choose one of the polynucleotides from the data which is largest. Guess that half are "knowns" and half are "unknowns" and guess that the axis between the two is at the end of the "knowns" determined in the preceeding reactions. Based on this guess, a matrix is set up and a solution is attempted using the sequential subsets of the chosen polynucleotide. If proper sequential subsets are not guessed initially, then other guesses are tried until a suitable set is determined. If an inconsistency is encountered for every set of sequential subsets, then the axis is shifted one nucleotide in the 5' direction and this is repeated up to a number of times equal to ½ the number of nucleotides in the polynucleotide selected until a solution is found. If this is unsuccessful, a polynucleotide one nucleotide less than the selected one or another polynucleotide of the same length is chosen and the process is repeated. Reiteration of this overall scheme is continued until an unambiguous solution is obtained. From any given data set only one solution is possible.

The following diagram demonstrates the 5' shift of the axis.

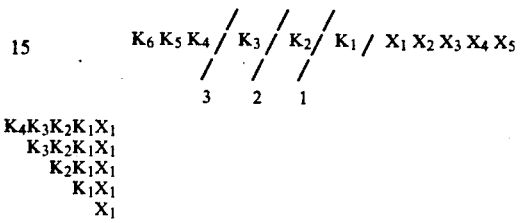

Number of Polynucleotides Necessary to Solve for a Given Number of "Unknown" Nucleotides For the polynucleotide generation method, Procedure I, the products conform to the criteria of Strategy I. The 5' randomization of the 3' random ended polynucleotides in reaction n+1 is carried out by the partial displacement of the 5' end of the polynucleotides from reaction n+1 with the 3' random ended polynucleotides from reaction n, followed by the subsequent destruction of single stranded nucleic acid. The "axis" is at the position that the 3' end of the longest polynucleotide transferred from reaction n would superimpose on the template. Maximum displacement of the 5' end of any polynucleotide in reaction n+1 is due to this polynucleotide; therefore, 3' to this point relative to the complement of the template, the condition that $X_n\ X_1$ is assured. The total number of final polynucleotides to be scanned is $\frac{1}{4}x^2$ where x is a variable. $\frac{1}{2}x$ "unknown" nucleotides are solved from a set of sequential subsets containing $x-1$ elements. The solution is obtained by using the method described in the Matrix Method of Analysis II where the form of the matrix is as appears in examples 1 and 2 of Solving Sequences by Matrix Method of Analysis, pages 35 and 36. The ratio of the number of nucleotides solved to the total number of fragments for a given reaction is:

$$\frac{\frac{1}{2}X}{\frac{1}{4}X^2} = 2/X$$

In methods of polynucleotide generation involving the extension of primers, Procedures II–V, consider the case where every primer is extended in a random fashion so that every primer contains every successive extended polynucleotide containing one more nucleotide than the preceeding polynucleotide up to an extension of n nucleotides. As described previously, if a given primer were superimposed on the template, then the axis relative to the template is at the end of the given primer. Since the primers are extended 5' to 3', then it is impossible to initiate transcription 3' to the "axis", therefore, the condition $X_n - X_1$ is assured. Furthermore, all of the primers are random on the 3, end, and if the longest and shortest differ by y nucleotides, where y is a variable, then by extending each primer randomly up to x nucleotides a total of xy different 3' and 5' random polynucleotides exist following elimination of the primers. The solution is obtained by using a configuration matrix and method of moving along the 45° initiation line as is described in Matrix Method of Analysis I. The configuration matrix in this case contains multiple rectangular matrices of the type described in Matrix Method of Analysis II. And, the lattices used to solve these matrices are of the form described in that section. Also, the "knowns" of the designated longest polynucleotide of the first rectangular matrix are assigned from the solution of the "unknown" part of the sequence from the preceeding reaction. The first rectangular matrix is solved as are other succeeding rectangular matrices using the method described in Matrix Method of Analysis II. In general, the method consists of moving along the 45° initiation line where the "unknowns" solved for in a preceeding rectangular matrix are used as the "knowns" in a succeeding rectangular matrix to solve for more of the sequence of the complement of the parent in the 3' direction. Then the solution of the sequence of these designated longest polynucleotides can be used collectively as knowns for a longer first designated longest polynucleotide in a reiteration of the procedure. This occurs when the first designated longest polynucleotide whose sequence is determined by the procedure of Matrix Method of Analysis II is of length less than the longest polynucleotide isolated. Sequential subsets of $x - 1$ polynucleotides are chosen to solve any given rectangular matrix in which the longest designated polynucleotide contains x nucleotides and at least 2 sets are necessary to solve for a total of x "unknowns" in a given configuration matrix. The ratio or the number of "unknowns" solved to the total number of polynucleotides generated is $x/xy = 1/y$.

For the preferred method, since the 3' random hybrid molecules are 5' randomized by a procedure which only removes RNA, the most 3' junction of RNA and DNA relative to the complement of the parent represents the "axis". Furthermore, if one RNA copy is isolated when following the procedure described in Methods I, then each of the polynucleotides generated from subsequent reactions and scanned, yields the solution of one nucleotide. Thus, the ratio of the number of "unknowns" solved to the total number of polynucleotides generated is one. If more than one RNA copy is isolated, then the ratio is $x/xR = 1/R$, where R is the number of RNA copies isolated.

Method of Sequential Subsets

The method of sequential subsets is based on arranging the polynucleotides in a hierarchial fashion such that any given polynucleotide of the set contains the exact same composition as the next smaller polynucleotide, except that it contains one extra nucleotide. All of these polynucleotides are generated by replicating a template in the 5' to 3' direction from the same initiating point; thus, the order of addition of the nucleotides progressing through the set assigns the sequence of the replicated polynucleotide in the same order from 5' to 3'.

Example of the Method of Sequential Subsets

Resolution of 3 polynucleotides of 3 nucleotides all containing 1-A; 2-T into the Sequences ATT; TTA; TAT.

| Fragment # | Data 1 | Data 2 | Data 3 |
|---|---|---|---|
| 1 | 2-T 1-A | 2-T 1-A | 2-T 1-A |
| 2 | 1-T 1-A | 2-T | 1-T 1-A |
| 3 | 1-A | 1-T | 1-T |
| Reading from the bottom to the top of a column, the sequence is: | | | |
| | ATT | TTA | TAT |

Determination of the Base Composition and Terminal Base Identity of a Polynucleotide The base composition and the identity of the terminal base of polynucleotides can be determined by methods such as chromatography, mass spectrometry, and NMR. For example, isolated polynucleotides can be hydrolyzed to mononucleotide subunits. Each ribonucleotide, deoxyribonucleotide, and dideoxyribonucleotide can be identified by its unique migration time, for example, using techniques such as HPLC, ion exchange chromatography, thin layer chromatography, etc. The relative amounts of each base can be quantified by absorbance, fluorescence, or by scintillation quantification if the nucleotides or bases are radiolabeled. Only a single dideoxynucleotide is present in each polynucleotide; therefore, it serves as the internal standard. All intensity values of signals corresponding to the different bases are normalized by the signal corresponding to the dideoxynucleotide to determine the base composition. Depending on the monitoring technique the intensity values may have to be corrected by a calibration factor before being normalized.

Determination of the Base Composition and Terminal Base Identity by Mass Spectrometry Mass spectrometry can be used to determine the base composition and terminal base. For example, to calibrate the mass spectrometer, spectra of known mixtures of the possible nucleotides or nucleosides are obtained and the intensity as a function of concentration for each nucleotide or nucleoside is determined from the intensities of the corresponding peaks of the spectra. When an unknown polynucleotide is fragmented by the electron beam or is prehydrolyzed to nucleotides or nucleosides and a mass spectrum is obtained, the known correspondence between a peak or peaks of the spectrum and a given base serves to make base assignments, and to determine the relative number of bases in the polynucleotide, the intensity of the peak or peaks corresponding to each base is corrected by the calibration factor. Then the base composition is determined by normalizing the corrected intensities with that corresponding to the dideoxyterminal nucleotide which is present only once in the polynucleotide; thus, it serves as internal standard. Calibration of a mass spectrometer is described by Hawley et al., *Nucleic Acid Research*, Vol. 5, Number 12, December 1978, pp 4949–4956.

Mass spectroscopy of free bases is also used to determined the base composition and terminal base by the same procedure as is used for the nucleotides and nucleosides with exception that base analogues are used as the dideoxynucleotides. Exemplary base analogues are given in the Determination of the Base Composition and Terminal Base Identity by Thin Layer Chromatography Section.

Determination of the Base Composition and Terminal Base Identity by Nuclear Magnetic Resonance Labeling and Spectroscopy The base composition and terminal base identity can be determined via nuclear magnetic resonance spectroscopy (NMR). For this purpose, the polynucleotides are constructed with nucleotides that are labeled with atoms that produce a signal detectable by NMR. The signal corresponding to each possible base and terminal base is distinctive. The base composition and terminal base identity can be determined from the known correspondence between the chemical shift of a given peak and given base and from the normalized intensity of each peak. Normalization is executed using the intensity of the signal corresponding to the dideoxyterminal nucleotide which is singularly present in each polynucleotide; thus, it serves as an internal standard.

Summary of the NMR Mode

The base composition and terminal nucleotide of a polynucleotide can be determined by NMR Spectroscopy using selectively NMR-labeled nucleotides.

Figure 7A:
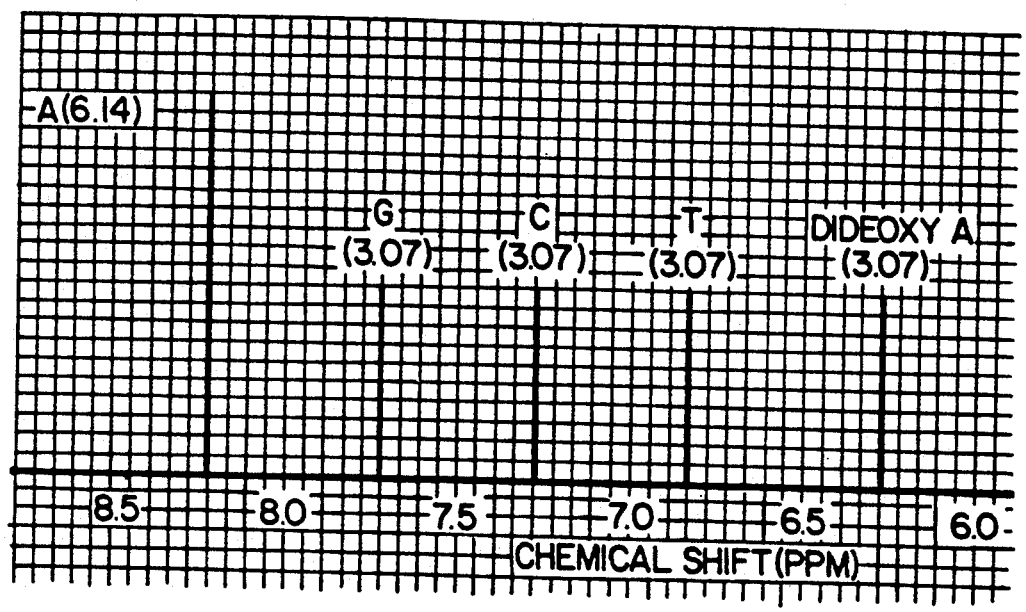
FIG. 7A is an example of NMR data from fragment #15 of FIG. 4.

An atom in each deoxynucleotide or ribonucleotide, U, A, T, G and C and a different atom for each dideoxynucleotide are chosen, where the signals from these atoms occur at chemical shifts which are unique from each other. Since each polynucleotide contains one dideoxynucleotide, it serves as the internal standard of signal intensity of one atom, one nucleotide. Therefore, the identity of the nucleotides present in a polynucleotide is determined from the chemical shift of the signal and the number of such nucleotides in a polynucleotide is determined by normalizing the signal intensity relative to the dideoxy internal standard. An example of NMR data for polynucleotide #15 of FIG. 4 is shown in FIG. 7A.

Nucleotides appropriately labeled for this procedure can be synthesized from properly labeled precursors. The proper atoms for labeling can be determined from an NMR spectrum of the nucleotide. A spectrum of the labeled nucleotides will have peaks present at the same chemical shift as that for the unlabeled spectrum with the absence of the peaks from nonlabeled atoms.

Two atoms useful for NMR-labels are $C^{13}$ and $H^1$. $C^{13}$-labeled nucleotides can be synthesized so that a single $C^{13}$ atom is substituted for a $C^{12}$ atom at a designated position. A different position must be chosen for each nucleotide and for each dideoxynucleotide. Based on the total number of carbon atoms in each nucleotide, the number of replaceable carbon atoms in each of the purine and pyrimidine bases are as follows:

| | |
|---|---|
| cytosine | 3 |
| thymine | 3 |
| adenine | 5 |
| guanine | 5 |

If hydrogen is the isotope detected, nucleotides are synthesized so that all exchangeable and nonlabeled hydrogens are replaced by deuterium atoms. Deuterium produces no signal detectable by NMR. Thus, the non-replaced, non-exchangeable hydrogens serve as the signal-generating species. For each nucleotide a hydrogen is selected which will yield a distinctive chemical shift. The number of non-exchangeable hydrogens on purine and pyrimidine are as follows:

| | |
|---|---|
| cytosine | 2 |
| thymine | 1 and 3 on $CH_3$ group |
| adenine | 2 |
| guanine | 1 |

Because a distinct label is needed for each nucleotide when it is internal and when it is terminating, for guanine, a hydrogen on the ribose can serve as label to satisfy this requirement.

Multiple samples of NMR-labeled polynucleotides can be scanned simulataneously using a field gradient. For deuterium containing nucleotides in a $D_2O$ solvent, the field strength ranges between 5 to 12 Tesla with resonating frequencing between 215 to 516 Megahertz. Therefore, with a chemical shift within any given sample of 10 parts per million in presence of a field gradient ranging from 5 to 12 Tesla, $8 \times 10^4$ samples could be scanned simultaneously; a Fourier transform would produce the frequency spectrum from the equation $F(w) = \int f(t) e^{-jw't} dt$. The Larmor equation, $w = \gamma H$, where the field gradient as a function of the spatial coordinates is known, can be used to assign the frequency spectrum to the individual samples, and, thus, the composition and terminal nucleotide assignment for the individual samples is assigned.

For $C^{13}$ NMR, $H_2O$ can be used as a solvent provided that protons are decoupled by irradiating at their resonance frequency. In using a field gradient, $D_2O$ solvents are unnecessary for a field strength less than 8 Tesla. Over the range of 2 to 8 tesla with corresponding resonances at 1.4 to 85.6 megaherz with a chemical shift of 100 parts per million for $C^{13}$, $1.5 \times 10^4$ samples can be scanned simultaneously and if $D_2O$ is used then higher fields; therefore, more samples can be handled simultaneously. Thus, by using a field gradient in the case of $H^1$, 80,000 samples can be scanned per second vs one per second if, for example, a mechanical belt were used to transport samples as they are scanned one at a time. Furthermore, NMR is accurate quantitatively within 1%; therefore, samples containing as many as 100 of a given nucleotide per strand can be analyzed and the largest polynucleotide from any given reaction can contain as many as 400 nucleotides.

Detailed Description of the NMR Mode

NMR labeled nucleotides can be synthesized chemically by starting with the properly labeled precursors and synthesizing the nucleotides. Methods for the synthesis of nucleotides are described in the following references:

Yamazek, Okotso, *Nucleic Acid Research*, vol. 3, no. 1, 1976, pp. 251-258 (guanine).

Hilbert, Jansen: *Journal of the American Chemical Society*, vol. 57, 1955, pp. 552-554 (cytosine).

Scherp, *Journal of the American Chemical Society*, May 1946, pp. 912-913 (thymine).

Richter, Loeffler; *Journal of the American Chemical Society*, vol. 82, June 1960, pp. 3144-3145 (adenine).

*Berichte Dan Deutschen Gesellschoft*, Jan-April, 1900, p. 1370.

*Berichten der Deutschen Chemischen, Gesellshaft* Band 2, 1897, p. 22; pp. 30-60.

The appropriate atoms for labeling can be determined from the NMR spectra of nucleotides. $C^{13}$ spectral data is set forth in Dorman, Roberts; *Proceedings of the National Academy of Sciences*, vol. 65, No. 1, Jan 1970, pp. 19-26; Jones, Winkley: *Proceedings of the National Academy of Sciences*, vol. 65, No. 1, Jan 1970, pp. 27-30: Mantsch, Smith, *Biochemical and Biophysical Research Communications*, vol. 46, No. 2, 1972; *Topics in Carbon 13 NMR Spectroscopy*, George Levy, John Wiley and Sons, New York, 1976.

$C^{13}$ NMR Studies of Biopolymers, pp. 244-248. Structural and Stereochemical Applications, pp. 469-478.

*CRC Handbook of Chemistry and Physics* E 71-E 75. $H^1$ NMR spectral references are as follows:

*CRC Handbook of Chemistry and Physics* E 71-E 75. Bubienko, Uniack, *Biochemistry*, 1981, 20, 6987-6994. Cheng, Kan, Leutzinger, *Biochemistry*, 1982, 21, 621-630.

$C^{13}$ and $H^1$ are two candidates for NMR labels where the specific signal due to the labeled atom is used to quantitate the number of these atoms present in a sample and therefore the number of molecules of the specific nucleotide in a hydrolyzed or nonhydrolyzed, purified sample. In the case of $C^{13}$ the nucleotides would be synthesized with a single $C^{13}$ atom replacing a $C^{12}$ atom in the designated position in each of the nucleotides and at a different atom for the terminating nucleotides. On the purines and pyrimidines alone the number of replaceable carbons is as follows: cytosine (3), thymine (3), adenine (5), guanine (5). Where hydrogen is the NMR label, nucleotides would be synthesized so that all non-exchangeable hydrogens would be replaced by deuterium which has no NMR signal; the hydrogen which is not replaced by deuterium is the label. For each nucleotide a hydrogen is selected which has a distinct chemical shift and a different hydrogen is selected for each nucleotide to serve as the label for the terminating nucleotides. The number of nonexchangeable hydrogens on the purine and pyrimidine molecules is as follows: cytosine (2), thymine (1+3 on $CH_3$), adenine (2), guanine (1). For guanine, a hydrogen on the ribose is labeled because the base only contains one hydrogen and two distinct hydrogens are necessary to label both the deoxy and dideoxynucleotide.

The cost of synthesizing the nucleotides in either case is not important because in both cases the nucleotides are reusable. With respect to noise $C^{13}$ has an advantage in that any contaminating nucleotides that are $C^{12}$ will not give an NMR signal. However, the natural abundance of $C^{13}$ is 1.1%, whereas the natural abundance of deuterium is 0.015% and the natural abundance of $H^1$ is 99.98%; therefore, there is more background noise when $C^{13}$ labeled nucleotides are used. Furthermore, the signal is much greater for hydrogen because its gyromagnetic ratio is much larger (42.6 for $H^1$; 10.7 for $C^{13}$). $C^{13}$ has a relative signal of $1.59 \times 10^{-2}$ compared to $H^1$.

To achieve a strong signal 50 u moles total of $C^{13}$ vs. 500 n moles total of $H^1$ are necessary. 1 ml solutions in which the total $H^1$ concentration is millimolar whereas 1 ml solutions in which the total $C^{13}$ concentration is at least 50 mM will give rise to a good signal.

For $H^1$, exchangeable hydrogens are replaced by deuterium by evaporating and resolvating the sample in $D_2O$. The NMR sample is less than 1 ml in volume, and the cost of $D_2O$ is $10 for 100 g; therefore, the cost is minor and the $D_2O$ is recoverable. Also, many NMRs use $D_2O$ as a signal lock. The time for scanning $H^1$ is less than 1 second whereas, due to the longer relaxation time, the scanning time of $C^{13}$ is on the order of seconds to minutes depending on the relaxation mechanisms available to the carbon nucleus. Also, pulse patterns are available to shorten the scan time for $C^{13}$ but some are not quantitative.

The equipment used to determine the nucleotide composition and terminal nucleotide can consist of an NMR spectrometer such as the Bruker WM-250, Varian HR-220, Nicolet NT-360 or a Bruker WM-500. Samples can be moved mechanically in and out of the NMR scanner with a belt apparatus for example. The NMR instrument can be designed to implement a field gradient and a Fourier transform algorithm to scan many samples at once. Technology of using a field gradient to assign NMR signal intensities to spatial coordinates in a line or in a plane is described in U.S. Pat. Nos. 4,021,726 and 4,115,730 respectively. NMR signal intensities can be assigned in one dimension. Thus, a field gradient need be applied along one axis. The samples are aligned along this axis and excited with rf signals and the free induction decay signals are read.

Many samples can be scanned at once using a field gradient. For $H^1$ using a $D_2O$ solvent, conventional field strengths range between 5 to 12 Tesla with resonating frequencies between 215 to 516 Megahertz. Therefore, with a chemical shift within any given sample of 10 parts per million in the presence of a field gradient ranging from 5 to 12 Tesla, $8 \times 10^4$ samples could be scanned simultaneously. A Fourier transform would produce the frequency spectrum from the equation: $F(w) = \int f(t)e^{-jwt}dt$. The Larmor equation, $w = \gamma H$, where the field gradient as a function of the spatial coordinates is known, can be used to assign the frequency spectrum to the individual samples. Therefore, the species in each sample can be quantified as described previously. The samples could be arranged either in a line or in two dimensions. In the former case, a single gradient is applied in the direction of the samples, the samples are excited with rf signals, and the free induction decay signals are measured. From this data, intensities of the nucleotides of the individual samples can be obtained as described previously. This method is used in the reconstruction of a line in a plane of a body section and is described in U.S. Pat. No. 4,021,726. This patent discloses a means and method where an additional gradient is necessary to select a plane perpendicular to the gradient along a line in that plane. This method and means are not necessary in the present invention. If the samples are arranged in two dimensions, then the same methods implemented in the above patent to reconstruct a cross sectional plane of the human body can be used to assign the intensity spectrum of the different nucleotides in the individual samples. For example, readout signals which relate to a single line could be obtained as described previously. And, to obtain information for the complete plane, cycle operations are necessary in which the sample is scanned successively along a sequence of lines. Another method is to apply an orthogonal gradient and simultaneously apply selective rf pulses to select strips in the plane and then apply orthogonal field gradients to the samples of such relative magnitudes that each point of the selected strip is subjected to a resultant magnetic field at an amplitude unique to that point. The free induction decay signal is then read out from the strips and the intensity of the signals is assigned spatially. Since the positions of the individual samples are known, the intensity spectrum of the nucleotides in the samples is assigned. A modified apparatus and method as described in U.S. Pat. No. 4,115,730 may be used with the exception that the means and method for isolating a plane do not apply. Additionally, an apparatus and method of implementing the so-called "echo-planar" method of assigning NMR signal intensities spatially may be used. In this method, as it pertains to the present invention, resonance is established in the plane and then two orthogonal gradients provide dispersion in the plane. One gradient is pulsed to space the frequencies of spins in adjacent strips allowing the other gradient to provide dispersion down the strips. The FID signals for each distinct sample so produced can be put in an array and two-dimensionally Fourier transformed to yield the signal intensity spectrum for each sample. The method and apparatus of the present invention is described in U.S. Pat. No. 4,335,282 except that the method and apparatus for selecting the plane does not apply.

For $C^{13}$ NMR, $H_2O$ can be used as a solvent provided that protons are decoupled by irradiating at their resonance frequency. When a field gradient is used, $D_2O$ solvents are unnecessary for a field strength less than 8 Tesla and over the range of 2 to 8 Tesla with corresponding resonances at 21.4 to 85.6 Megaherz with a chemical shift of 100 parts per million for $C^{13}$, $1.5 \times 10^4$ samples can be scanned simultaneously. If $D_2O$ is used, then higher fields and therefore, more samples can be handled simultaneously. Thus, it can be seen that by using a field gradient in the case of $H^1$, 80,000 samples can be scanned per second vs. 1 per second if, for example, a mechanical belt were used to transport samples as they are scanned one at a time. Furthermore, NMR is accurate quantitatively within 1%; therefore, samples containing as many as 100 of a given nucleotide per strand can be analyzed and the largest fragment from any given reaction can contain as many as 400 nucleotides.

An example of the NMR method of the present invention follows:

A family of polynucleotides are separated by polyacrylamide gel electrophoresis where the nucleotides and terminal dideoxynucleotide of each polynucleotide are NMR labeled. Separated fractions can be collected from the gel by instrumentation described in Electrophoresis Instrumentation. In the case that $C^{13}$ nucleotides are used, the fractions may be collected from buffer well or on glass beads (see Electrophoresis Instrumentation). When $H^1$- deuterium labeled nucleotides are used, the preferred method is to collect the DNA on glass beads. This procedure is a modification of Method II described by Vogelstein et al., PNAS 76, 615 (1979). Glass beads are present in the lower anode well and the electrophoresis buffer in this well contains saturated NaI as described in the above reference. Following collection, the glass beads are washed with the NMR buffer containing saturated NaI. This step is implemented to remove hydrogen atoms from the sample that would produce an NMR signal in the same region as the signal of the nucleotides. The DNA is eluted from the beads by suspending them in NMR buffer in the absence of NaI.

The isolated polynucleotides are scanned with an NMR spectrometer.

$H^1$ spectra: If deuterium-$H^1$ labeled nucleotides are used, then samples should be made approximately 1 mM in concentration. The urea and electrophoresis buffer can be removed by ion exchange chromatography. Also, if the glass bead technique is employed as described previously and in the Electrophoresis Instrumentation Section, and the electrophoresis buffer contains urea then the urea and electrophoresis buffer can be exchanged for phosphate buffer and $D_2O$ by first rinsing the beads to which the nucleic acid is adsorbed with this buffer saturated with NaI and then eluting the polynucleotides from the beads by dissolving them in this NMR buffer in the absence of NaI. The proton spectrum may be obtained at 41° C., 1 mM strand concentration at 220 MHZ. If base stacking interactions significantly distort the proton NMR spectra, then the nucleotides can be removed from the ribose or deoxyribose backbone by adding an acid anhydride which will depurinate and depyrimidate the polynucleotides.

$$SO_2 + D_2O \rightarrow D_2SO_3$$

$$SO_3 + D_2O \rightarrow D_2SO_4$$

$$CO_2 + D_2O \rightarrow D_2CO_3$$

$$N_2O_3 + D_2O \rightarrow DNO_2$$

$$N_2O_5 + D_2O \rightarrow DNO_3$$

$$Cl_2O_7 + D_2O \rightarrow DClO_4$$

$$P_2O_3 + D_2O \rightarrow D_3PO_3$$

$$P_2O_5 + D_2O \rightarrow D_3PO_4$$

NaOD can be added to neutralize the solution. When this procedure is used, only a fraction of any polynucleotide sample is used and the remainder is reserved for subsequent steps.

$C^{13}$ NMR Spectra: $C^{13}$ spectra may be gathered at 15.1 MHZ using 25 mM aqueous solutions and 1 percent (v/v) p-dioxane as the internal standard. Spectra can also be obtained using a field gradient as described previously. Proton containing reagents need not be removed, and protons may be decoupled by noise modulation at 600 MHZ. $C^{13}$ NMR spectral methods are discussed by Dorman et al. PNAS 65:19-26 (1970). If base stacking interactions distort the spectra, then part of the sample can be depurinated and depyrimidated with strong acid and neutralized with base.

Determination of the Base Composition and Terminal Base Identity of an Oligo or Polynucleotide by Thin Layer Chromatography and Labeling Mass Spectrometry The preferred methods for determining the base composition and terminal base identity of an oligo- . or polynucleotide containing a dideoxyterminal nucleotide is via thin layer chromatography and labeling mass spectrometry. In one embodiment, nucleotides, nucleosides, or free bases or reaction products of bases are liberated from the oligo- or polynucleotide and are separated by thin layer chromatography. The intensity of distinct chromatographic bands corresponding to different bases is quantified.

In another embodiment the fifth position of the pentose of the nucleotides of the oligo- or polynucleotide are mass labeled in such a fashion that each possible nucleotide and terminal nucleotide releases a distinct mass labeled molecule such as formaldehyde from the fifth position of the pentose when the oligo or polynucleotide is degraded to 3' nucleotides or nucleosides and reacted with periodic acid. The intensity of the liberated molecules of different masses corresponding to different bases is recorded using a mass spectrometer.

In both embodiments, the intensities of the signals which correspond to the different bases are normalized with the signal corresponding to the terminal base which serves as the internal standard with a signal of unity. The base composition and internal base identity are given by the normalized data.

Background

Deoxyribonucleic acid (DNA) and ribonucleic acid (RNA) are chainlike macromolecules that function in the storage and transfer of genetic information. The monomeric units of DNA called deoxyribonucleotides; those of RNA are ribonucleotides. Each nucleotide contains three characteristic components; (1) a nitrogenous heterocyclic base, which is a derivative of either pyrimidine or purine; (2) a pentose; and (3) a molecule of phosphoric acid.

Four different deoxyribonucleotides serve as the major components of DNAs; they differ from each other only in their nitrogenous base components, after which they are named. The four bases characteristic of the deoxyribonucleotide units of DNA are the purine derivatives adenine and guanine and the pyrmidine derivatives cytosine and thymine. Similarly, four different ribonucleotides are the major components of RNAs; they contain the purine bases adenine and guanine and the pyrimidine bases cytosine and uracil.

Deoxyribonucleotides contain as their pentose component 2-deoxy-D-ribose; ribonucleotides contain D-ribose. Both pentoses occur in their furanose forms in nucleotides. The pentose is joined to the base by a B-N glycosyl bond between carbon atom 1 of the pentose and nitrogen atom 9 of purine bases or nitrogen 1 of pyrinidine bases. The phosphate group of nucleotides is an ester linkage with carbon atom 5 of the pentose to form 5' nucleotides or is an ester linkage with carbon atom 3 to form 3' nucleotides. When the phosphate group of a nucleotide is removed by hydrolysis, the structure remaining is called a nucleoside.

DNA and RNA are macromolecules which are polymers of nucleotides joined by phosphodiester bonds of the 3' hydroxyl group of one nucleotide and the 5' phosphate of another nucleotide. These polymers are formed by enzymes which polymerize an antisense copy of an existing polymer by using it as a template by a process called replication where a purine is incorporated into the growing copy by being paired with a pyrimidine of the template, and where a pyrimidine is incorporated into a growing copy by being paired with a purine of the template. Polymerization is terminated when a nucleotide lacking a 3' OH is incorporated into the growing chain, because the next nucleotide can not be linked to form a phosphodiester bond. Such nucleotides which lack a 3' OH have the same base characteristics as deoxyribonucleotides; and contain 2, 3-dideoxy-D-ribose as the pentose are called dideoxynucleotides. They are typically used to randomly terminate replication reactions of a DNA or RNA strand. The resulting products are oligo or polynucleotides which are terminated by a dideoxynucleotide. It is important to determine the base composition and terminal base identity of oligo- or polynucleotides in order to sequence the strand from which they were replicated.

Summary of the Preferred Modes

The component bases nucleosides, and nucleotides of an oligo- or polynucleotide can easily be separated by electrophoretic or chromatographic means. This property is exploited by the present invention to determine the base composition and terminal base identity of an oligo- or polynucleotide by means of thin layer chromatography (TLC).

The oligo- or polynucleotide is degraded to component bases, reaction products of bases, nucleosides or nucleotides. An immobile phase and solvent are chosen which will resolve each degraded component as a unique chromatographic band. The mixture of components are applied to the TLC plate and elution is carried out until the components are resolved. The identity of the bands are determined from known Rf values. The intensity of each band is determined by fluorescence, absorption, reflectance, or radiodecay quantification, and the intensity of the band corresponding to the terminal base is used as the internal standard to normalize the signals of the bases corresponding to the other component bases to give the base composition directly.

An alternative approach to exploiting the different physical properties of bases, reaction products of bases, nucleosides and nucleotides for their separation and quantification is to initially label the pentose of all component nucleotides which are used in a replication reaction of a strand of unknown sequence to produce the desired oligo- or polynucleotide for which the base composition and the terminal base identity information is then determined via mass spectroscopy. Quantification of each component base can be obtained by analyzing the reaction products derived from the nucleotides of the oligo- or polynucleotide to record the intensity of the mass signal from each uniquely labeled reaction product where the correspondence of the mass signal of each labeled reaction product to the particular base is known. Normalization of the signal by that corresponding to the dideoxyterminal, gives the composition directly.

A method of the present invention to determine the base composition and terminal base identity is to uniquely mass label the fifth position of the pentose of each nucleotide. These nucleotides are used as substrates in a replication reaction to synthesize the oligo- or polynucleotide. Following its synthesis and isolation, the oligo- or polynucleotide is degraded to 3' nucleotides or nucleosides, and the B-N glycosyl bond between the base and the pentose of the nucleotides or nucleosides is chemically broken to produce diols of carbons 4 and 5 of the pentose. The reaction mixture is treated with periodic acid to release labeled formaldehyde from only the carbon 5 position of the pentose. The intensity of each distinct mass labeled formaldehyde molecule is recorded with a mass spectrometer, and the signals are normalized with that of the signal corresponding to the dideoxyterminal base. From the known correspondence between the masses of the labels and the bases, the composition and terminal base identity is given directly by the normalized signals.

Detailed Description of the Preferred Modes

Determination of the Base Composition and Terminal Base Identity by Thin Layer Chromatography To determine the base composition and terminal base identity by thin layer chromatography, the oligo or polynucleotide is subjected to a digest or degradation reaction to yield predictable component species such as component bases, reaction products of bases, nucleosides, or nucleotides. The reaction mixture is applied to a TLC plate and is eluted with a suitable solvent until each of the component bases, reaction products of bases, nucleosides, and/or nucleotides are resolved from each other. The intensity of each chromatographic band is quantified by absorbance, reflectance, fluorescence, or radioactivity. All bands are identified from known Rf values, and the signals from all bands are normalized by the signal of the band which contains the component released from the dideoxyterminal of the oligo or polynucleotide. The Rf values and the normalization process gives the base composition and terminal base identity.

The digest of the oligo or polynucleotide can be performed enzymatically with an exonuclease to produce 3' or 5' nucleotides which can be further enzymatically degraded to nucleosides with alkaline phosphatase.

Also, hydrolysis of the B-N glycosyl bond between carbon atom 1 of the pentose and nitrogen 9 or purine bases or nitrogen I of pyrimidine bases can be achieved by heating the oligo or polynucleotide in strong acid to release free bases. And, reactions exist which will selectively break one of the purine or pyrimidine B-N glycosyl bond in the presence of the other. Thus, the pyrimidine and purine composition can be determined, and the terminal base can be identified from the combined results of two separate reactions where equal volume aliquots are used to run separate depurination and depyrimidation reactions followed by separation of the products of each reaction independently by TLC.

The chromatographic bands are quantified and then normalized with the signal of the band corresponding to the terminal base, internal standard. For the case in which free bases or reaction products of free bases are used as the components released from the oligo- or polynucleotide and separated by TLC, it is necessary that each base or the reaction product of each base which is released from each of the four possible terminal nucleotides has a unique mobility so that it can be separated from the other bases and/or reaction products of bases. Thus, the terminal dideoxynucleotide must possess a base analogue which is incorporated into DNA by the polymerase as if it where the base for which it substitutes. Examples include 5-bromouracil and 5-iodouracil as analogues of thymine; tubercidin, toyocamycin, formycin, 7-deazanebularin, 2-aminopurine, sangivamycin, 2-aminoadenine, 2-fluoroadenine, and 8-azaadenine for analogues of adenine; 5-methylcytosine, 5-hydroxymethylcytosine, 2-thiocytosine, N4-methylcytosine, N4-acetylcytosine, isocytosine, and 5-azacytosine as analogues of cytosine; and 7-deazaguanine, crotonoside, 1-methylguanine, N2-methylguanine, N2,N2-dimethylguanine, 7-methylguanine, 6-selenoguanine, and 6-thioguanine as analogues of guanine.

Selective chemistry which exclusively releases purine or pyrimidine bases from the oligo-or polynucleotide is that of the Maxam-Gilbert sequencing reactions. The B-N glycosyl purine bond and pyrimidine bond can be selectively broken by running to completion the G-A formic acid reaction and the T-C hydrazine reaction of the Maxam Gilbert sequencing chemistry, respectively.

An example of the TLC method of the present invention where an exonuclease is used to degrade the oligo- or polynucleotide to component 5' nucleotides which are separated by the TLC and quantified follows.

The oligo- or polynucleotide which contains P32 labeled nucleotides with known activity of approximately $10^6$ dpm/ug are hydrolyzed to 5' nucleotides by incubating with exonuclease as described by Rabin, E.Z., et al., Biochimica et Biophysica. Acta, 259, (1972), pp 50-68.

The nucleotides are separated by TLC and the radioactivity of each band is quantified. The identity of each nucleotide on the TLC plage is identified by its known Rf value. The composition is obtained by normalizing the signal from each nucleotide with the signal from the terminal which serves as an internal standard of one nucleotide.

TLC has many advantages which include sharpness of resolution, picomolar sensitivity, simplicity, speed, and low cost. In general, the method is as follows: the sample is applied from a micropipette 2 cm from the lower edge of a TLC plate as a volume of 0.05–1 ul. The sample can be applied directly without extraction from proteins or change of solvent. (See Methods of Enzymology, XXIX, pp. 618–19.) Furthermore, if the volume is greater than 1 ul, the larger volumes are spotted in portions with intermediate drying. The TLC plate is placed in a developing tank and elution is carried out until the solvent is about 2 cm from the end of the plate. After drying, the nucleotide spots can be located under ultraviolet light or by autoradiography. The nucleotide containing areas can be cut from the support and assayed for radioactivity by putting each spot in a liquid scintillation vial, adding scintillation cocktail and counting in a liquid scintillation counter. Also, quantification can be obtained directly by densitometry as discussed in Haer, F.C., An Introduction to Chromatography on Impregnated Glass Fiber, Ann Arbor Science Publishers Inc., Ann Arbor, Mich., 1969, pp. 55–57. Pertinent references for the Rf values of free bases, nucleosides, nucleotides, and methods of TLC are as follows: CRC Handbook Series in Chromatography, Vol 1, 1972, pp. 618–23. Randerath, K.,.Angew. Chem., 73, 674 (1961) from J. Chromatogr., 9, (1962) p. 35. Coffey, R.G. and R.W. Nenburgh, J. Chromatogr., 11, 376 (1963). Shasha, B. and R.L. Whistler, J. Chromatogr., 14, 532 (1964). Haer, F.C., An Introduction to Chromatography on Impregnated Glass Fiber, Ann Arbor Publishers, Inc., Ann Arbor, Mich., 1969, pp. 1–63 and 143–51. Strickland, R.G., Anal. Biochem., 10, 116 (1965). Grippo, B., Iaccarino, M., Rossi, M., and E. Scarono, Biochim. Biophys. Acta, 95, 1 (1965). Wang, K.T., and I.S.Y. Wang, Biochim. Biophys. Acta, 142, 280 (1967). Dietrich, C.P., Dietrich, S.M.C., and H.G. Points, J. Chromatogr, 15, 277 (1964). Randerath, K. Agew. Chem. Intern. Ed. Engl., 1, 435 (1962). Randerath, K., and Struck, J., J. Chromatogr., 6, 365 (1961). Randerath, K., Biochem. Biophys. Res. Commun., 6, 452 (1961/62). Methods of Enzymology LIX, pp. 62–80. Methods of Enzymology XXIX, pp. 618–19 and 285–91. Methods of Enzymology XII, pp. 323–344. Methods of Enzymology XX, pp. 119–125.

Determination of the Base Composition and Terminal Base Identity By Mass Spectrometry In addition to TLC, the base composition and terminal base identity is also determined by mass spectrometry.

Because DNA is composed of four different bases, eight unique signals are necessary to identify each base and possible terminal base of an oligo- or polynucleotide by mass spectroscopy. The mass spectrum of intact polynucleotides can not be obtained directly because these molecules are nonvolatile. The mass spectrum of each nucleotide and nucleoside is extremely complex. Each spectrum consists of peaks as a function of mass whose relative heights correspond to the relative yield of charged fragments of the masses at which the peaks are found where the charge fragments are generated from the nucleotide or nucleoside as it is broken up by an ionizing electron beam. The relative heights of the peaks is thus a function of the production efficiency of the charged fragments of different masses. The complexity of the spectrum increases for a mixture of nucleotides and/or nucleosides, and the relative intensity of the peaks of a spectrum of a mixture is dependent on the relative production efficiency of the nucleotide and/or nucleoside fragments of different masses which correspond to the peaks of the spectrum as well as the relative concentration of the nucleotides and/or nucleosides of the mixture.

Molecules with less complex mass spectra can be produced chemically from nucleotides or nucleosides. However, if different reactions are performed on different nucleotides or nucleosides or if the reaction product which is mass spectroscopically analyzed is not the same for each base, then the determination of the base composition and terminal base identity becomes complicated. For the former case, the intensity of the peak characteristic of each nucleotide or nucleoside and corresponding to each base is dependent on the extent of the reaction which generates the molecules whose mass spectrum possesses the given peak. For the latter case, the intensity of the peak characteristic of each nucleotide or nucleoside and corresponding to each base is dependent on the production efficiency of the fragment of the peak from the given reaction product. For each base and possible terminal base, the production efficiency and extent of reaction must be calibrated and the intensity signal must be corrected. This necessity is averted by the method of the present invention which entails labeling the fifth position of the pentose of each nucleotide of an oligo or polynucleotide and causing the nucleotides or nucleosides released from this macromolecule to undergo a common reaction to release the same volatile molecule which is analyzed by mass spectroscopy. Because a common reaction is performed on all component pentoses, the dependence of the relative intensities of the signals corresponding to different bases on the extent of reaction is eliminated. And, because the reaction product which is an analyzed by mass spectroscopy is the same for each base, the relative intensity of the signal corresponding to each base is dependent only on the relative concentration of each mass labeled reaction product and not on the ion production efficiency.

The mass labeled molecule which is sensed for all eight possible signals indicating base composition and terminal base identity of any given fragment is formaldehyde. Calibration of ion production efficiency of different sensed species is eliminated where all mass labeled formaldehyde molecules have the same production efficiency. The atoms used for labeling are oxygen, carbon, and hydrogen at the fifth carbon position of the nucleotide pentose. The atoms and isotopes involved in labeling are given below with their natural abundances and half lives.

| Isotope | H1 | H2 | H3 | | | |
|---|---|---|---|---|---|---|
| % Natural Abundance | 99.985 | .015 | 0 | | | |
| Halflife | | | 12.26y | | | |
| Isotope | C12 | C13 | C14 | O16 | O17 | O18 |
| % Natural Abundance | 98.89 | 1.11 | 0 | 99.759 | .037 | .204 |
| Halflife | | | 5730y | | | |

Carbon, hydrogen, and oxygen isotopes are used such that each successive formaldehyde molecule differs by one atomic mass unit. A method of synthesizing sugar molecules labeled in the end position is described by Sowden, John C., *J. Am. Chem. Soc.* 74, (1952) pp. 4377–4379. The mass labeled pentoses are synthesized using this procedure where the appropriate isotopes of carbon, oxygen, and hydrogen are present in the reagents. Possible distinct mass labeled formaldehyde molecules are given as follows:

Exemplary Mass Labeled Formaldehyde Molecules

 (1)

 (2)

 (3)

 (4)

 (5)

 (6)

 (7)

 (8)

 (9)

The oligo or polynucleotide, for which the composition and terminal base data is determined, is hydrolyzed to 3' nucleotides or nucleosides. For all 3' nucleotides, including ribonucleotides, deoxyribonucleotides, and dideoxyribonucleotides and nucleosides, hydrolysis of the B-N glycosyl bond between carbon atom 1 of the pentose and nitrogen 9 of purine bases or nitrogen 1 of pyrimidine bases produces a terminal diol only involving pentose positions 4 and 5. When oxidized with periodic acid the 4–5 diol pentose releases a formaldehyde molecule only from the fifth carbon position which contains carbon atom 5 and the two hydrogen atoms and oxygen atom bound to carbon atom 5. Reactions exist which will selectively break one of the purine or pyrimidine B-N glycosyl bond in the presence of the other. Because the glycosyl bond must be broken to produce a terminal diol in order for formaldehyde to be released from the fifth carbon position, this glycosyl bond breaking chemistry can be used to separately analyze exclusively the purine or pyrimidine components of an oligo or polynucleotide containing both types of bases by the labeling mass spectroscopic method. Examples of methods of determining the purine and pyrmidine components in two separate reactions and as one reaction follows.

Scheme 1

Release of Formaldehyde from Purines and Pyrmidimes as Separate Reactions

For example, exemplary formaldehyde molecules one, two, four, and five are used as molecules to identify the number of adenine and guanine bases and the presence of terminal adenine or terminal guanine in any given oligo or polynucleotide in one reading and to identify the number of thymine and cytosine bases and the presence of terminal thymine or terminal cytosine in any given oligo or polynucleotide by a second reading where the corresponding isotopes of carbon, oxygen, and hydrogen are used to label the fifth position of the nucleotide pentoses corresponding to the different bases. The two independent readings are performed on samples from two separate reactions where each reaction mixture contains an equal volume aliquot of a hydrolyzed oligo or polynucleotide. One reaction liberates labeled formaldehyde from purine nucleotide pentoses, and the other liberates labeled formaldehyde from pyrimidine nucleotide pentoses. It is implicit that the signal given by the terminal nucleotide serves as the internal standard for the signals of the bases in both reactions. The reaction sequence is as follows:

The oligo or polynucleotide is isolated and hydrolyzed to 3' nucleotides or nucleosides. For example, the former reaction can be accomplished with a nuclease such as exonuclease from B. subtilis. Two equal volume aliquots are taken of the hydrolyzed reaction mixture. One aliquot is treated to break purine B—N glycosyl bonds, and the other is treated to break pyrimidine B—N glycosyl bonds where methodology such as that of the Maxam-Gilbert sequencing chemistry is used. For example, formic acid is used in the former reaction, and hydrazine is used in the latter where the reactions are run to completion. In both cases, breaking the B—N glycosyl bond creates a diol involving carbon positions 4 and 5 of the pentoses. A molecule containing such a grouping is oxidized and cleaved by period acid (HIO4). Formaldehyde is released from the fifth carbon only when the glycosyl bond has been broken. The sample is heated to liberate formaldehyde gas. And, only the signals of molecules with mass between 30 and 34 daltons are recorded by mass spectroscopy. Formaldehyde is not released from any other pentose position. Assuming the reactions go to the completion or to the same extent for all pentoses, noise is limited to the purity of the labels. If the 14C labeled nucleotides are used within 83 years and the 3H labeled nucleotides are used within 64 days, the composition and terminal base identity is determined accurately for oligo or polynucleotides of length of approximately 400 nucleotides by this spectroscopic method. Mass spectroscopy offers advantages of a faster processing time and a greater sensitivity than TLC methods. The processing time and sensitivity are a fraction of a second and femtomoles for the former and minutes and picomoles for the latter. And, the formaldehyde molecules differ by at least one atomic mass unit and cover a narrow mass range; thus, an unsophisticated mass spectrometer is adequate. Thus, this technology represents a valuable alternative to TLC methods.

The mass spectrum of formaldehyde consists of three peaks which are each separated by one atomic mass unit. Formaldehyde molecules of different masses can contribute intensity to the same peak; thus, the signal from a mixture of mass labeled formaldehyde molecules must be processed. Signal processing involves subtracting the contribution that one of the lower mass peaks of a heavier formaldehyde molecule makes to the peak of highest mass of a lighter formaldehyde molecule. The initial corrections can be derived by multiplying the spectral peak of highest mass separately by the two calibrated numbers which gives the intensities of the two additional peaks of the formaldehyde molecule corresponding to the spectral peak of highest mass. These contributions to the peaks of one and two atomic mass units less than the most massive peak are subtracted from the respective spectral peaks. The process is then repeated using the now corrected peak of one atomic mass unit less than the spectral peak of highest mass. And, the process is reiterated until the corrected heaviest peak of each formaldehyde molecule is obtained. These processed signals are used to determine the base composition.

Figure 7B:
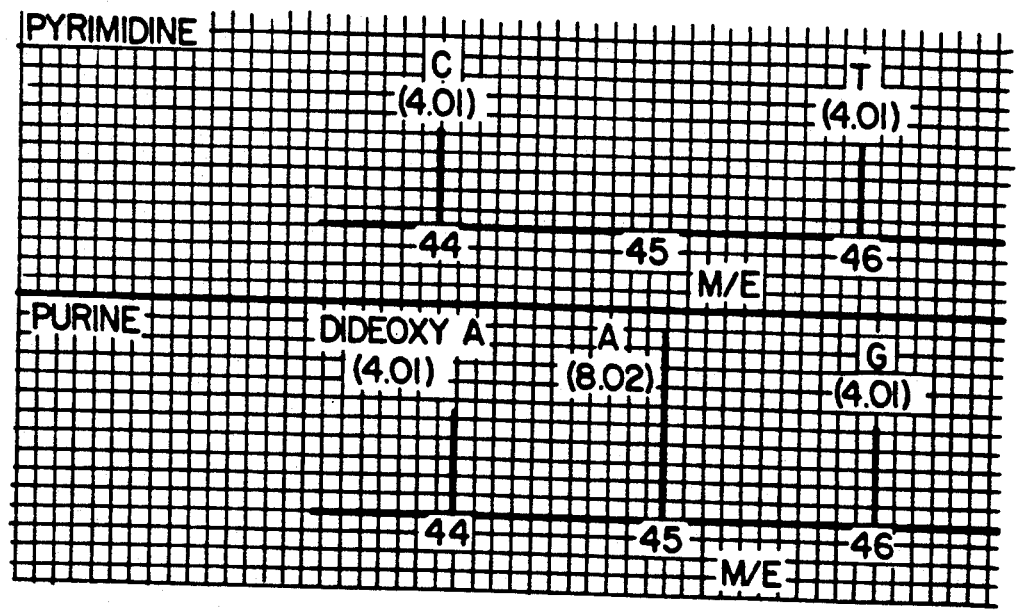
FIG. 7B is an example of mass spectroscopic data from fragment #15 of FIG. 4 where the data was obtained of labeled $CO_2$ using scheme 1 as described in the Determination of the Base Composition and Terminal Base Identity by Mass Spectrometry Section.

Implicit in the case where a label of mass 32 daltons is used is that $O_2$ is removed by a scavenging system such as MnO. Alternatively, GC-Mass spectrometry is used, or formaldehyde is preoxidized to $CO_2$ before recording. Carbon dioxide gives a distinct line signal in mass spectrometry which needs no further processing as is necessary for that of formaldehyde; however, recording $CO_2$ precludes the scheme of additionally labeling the hydrogens of formaldehyde described below. Ultimately, the cost effectiveness of additional labeling and removing $O_2$ and accuracy will determine which scheme to implement for the specific application. FIG. 7B is an example of mass spectroscopic data from fragment #15 of FIG. 4 where the data was obtained of labeled CO2.

Scheme 2

Release of Formaldehyde from Purines and Pyrimidines as a Single Reaction

For example, exemplary formaldehyde molecules one, two, and four through nine are used to identify the number of adenine, guanine, cytosine, and thymine bases and the presence of terminal adenine or thymine or guanine or cytosine where the corresponding isotopes of carbon, hydrogen, and oxygen are used to label the fifth position of the nucleotide pentoses corresponding to the different bases. The oligo or polynucleotide to be analyzed is hydrolyzed to 3' nucleotides or nucleosides as for scheme 1. However, the B—N glycosyl bond for all nucleotides is broken in one reaction mixture. This can be achieved by heating in acid for example. The periodic acid oxidation is run, and formaldehyde of mass 30–38 daltons is released as a gas and quantified with a mass spectrometer. Implicit is that O2 is removed by a scavenging system or by gas chromatography.

Electrophoresis Instrumentation Section

Figure 10A:
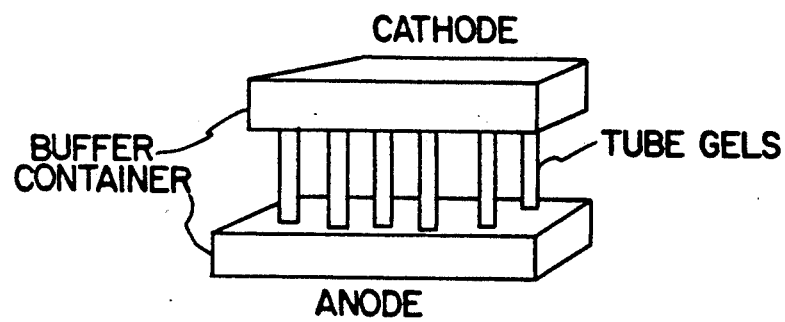
FIG. 10A is a diagram of the electrophoresis apparatus.
Figure 10B:
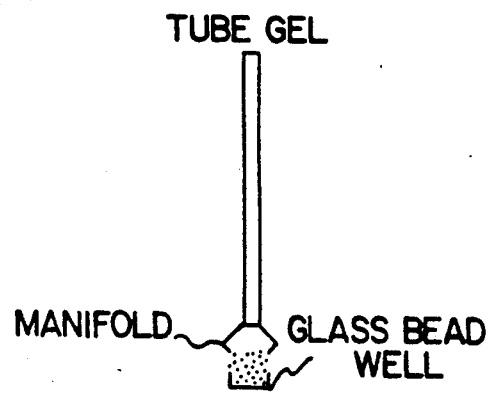
FIG. 10B is a cross section of a tube gel, manifold, and glass bead well.
Figure 10C:
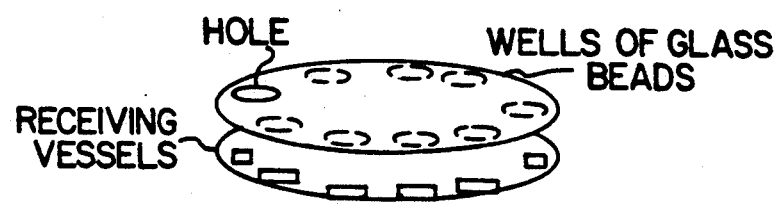
FIG. 10C is a diagram that illustrates the collection of the glass beads in receiving vessels.

For each reaction mixture, load the polynucleotides which differ by one base pair on to X tube gels (where X equals the number of reaction mixtures). The tube gels are arranged in a row and are spaced so that the bottom of each is located on a separate disc of a carousel collector that contains wells of activated glass beads which adsorb the nucleic acid. The carousel collection apparatus comprises concentric disks containing wells of glass beads. The disks rotate independently of each other as electrophoresed bands are collected individually from the tube gel. The apparatus is shown in FIG. 10D. Thus, there are X concentric disks, each having Y wells, where Y is the number of samples to be collected from a single tube gel. The tube gels exist as part of an electrophoresis apparatus shown in FIG. 10A. A super saturated NaI buffer which enhances the binding of the nucleic acid to the beads is used during electrophoresis. The beads are part of the matrix through which the DNA migrates in the presence of the applied electric field, and the solvent completes the circuit because it readily permeates through the glass beads. See FIG. 10B. Absorption of UV light by nucleic acid is monitored at each tube by a photocell (other methods of monitoring bands are mass spectroscopy; scintillation detection of radiolabeled nucleotides, nucleosides, or bases; ethidium bromide fluorescence detection and conductance perturbation detection) and the disk is rotated to move the next well into place following each peak. For the case where NMR labeled nucleotides are used, after the separation procedure is finished, the solvent is removed; the glass beads are mildly washed with $D_2O$, and then the disks are rotated so that the wells successively align with a hole through which the samples of glass beads fall into receiving vessels as depicted in FIG. 10C. The nucleic acid is removed from the glass beads by vigorous solvation in $D_2O$. The polynucleotides are hydrolyzed in acid anhydride and an NMR scan is performed. For the case where mass labeled nucleotides are used, the polynucleotides adherent to the glass beads can be reacted to release formaldehyde directly or the polynucleotides can be liberated from the glass beads by washing the beads with or suspending the beads in a solvent which does not contain NaI.

Such as recovery of the polynucleotides is necessary for any subsequent sequencing reactions and/or enzymatic digests to release nucleotides or nucleosides which are analyzed by chromatography. Free bases of the polynucleotide are released from the glass beads by heating them is strong acid where analysis of the liberated bases is by chromatography.

DNA can also be collected as fractions by removing DNA from a small anode well (via outlet) which is refilled with electrophoresis buffer (via inlet) after each collection. The electrophoresis apparatus is as described previously and also appears in FIG. 10A. One unit of the collection apparatus is demonstrated in FIG. 10E, where the collection apparatus consists of X units—one for each of the tube gels. Each band is collected individually; thus, Y collections are performed during the electrophoresis procedure.

Automating the Method

The general system design of an automated apparatus for the labeling strategy of scheme 2 is as follows:

a) a first reaction vessel comprising a reaction chamber having means for transfer of reagents, reactants and reaction products into and out of the chamber;

b) means for separating individual oligonucleotides and polynucleotides on the basis of length, the separating means having means for receiving reaction products from the first reaction vessel;

c) a second reaction vessel for oxidizing pentose sugars comprising a second reaction chamber having means for transfer of reactants and reagents into the chamber and gaseous by-products of a reaction out of the chamber;

d) means for selectably transferring separated oligonucleotides and polynucleotides from the separating means alternatively into the first or the second reaction vessel;

e) a second transfer means for transferring the gaseous by-products out of the second reaction vessel;

f) a chamber for collecting the gaseous by-products, the chamber being in communication with the second transfer means;

g) third transfer means for transferring gaseous by-products from the collection chamber to the analyzing means; and h) means for analyzing the relative abundance of the components of the gaseous by product by mass, the analyzing means being in communication with the third transfer means.

Figure 8:
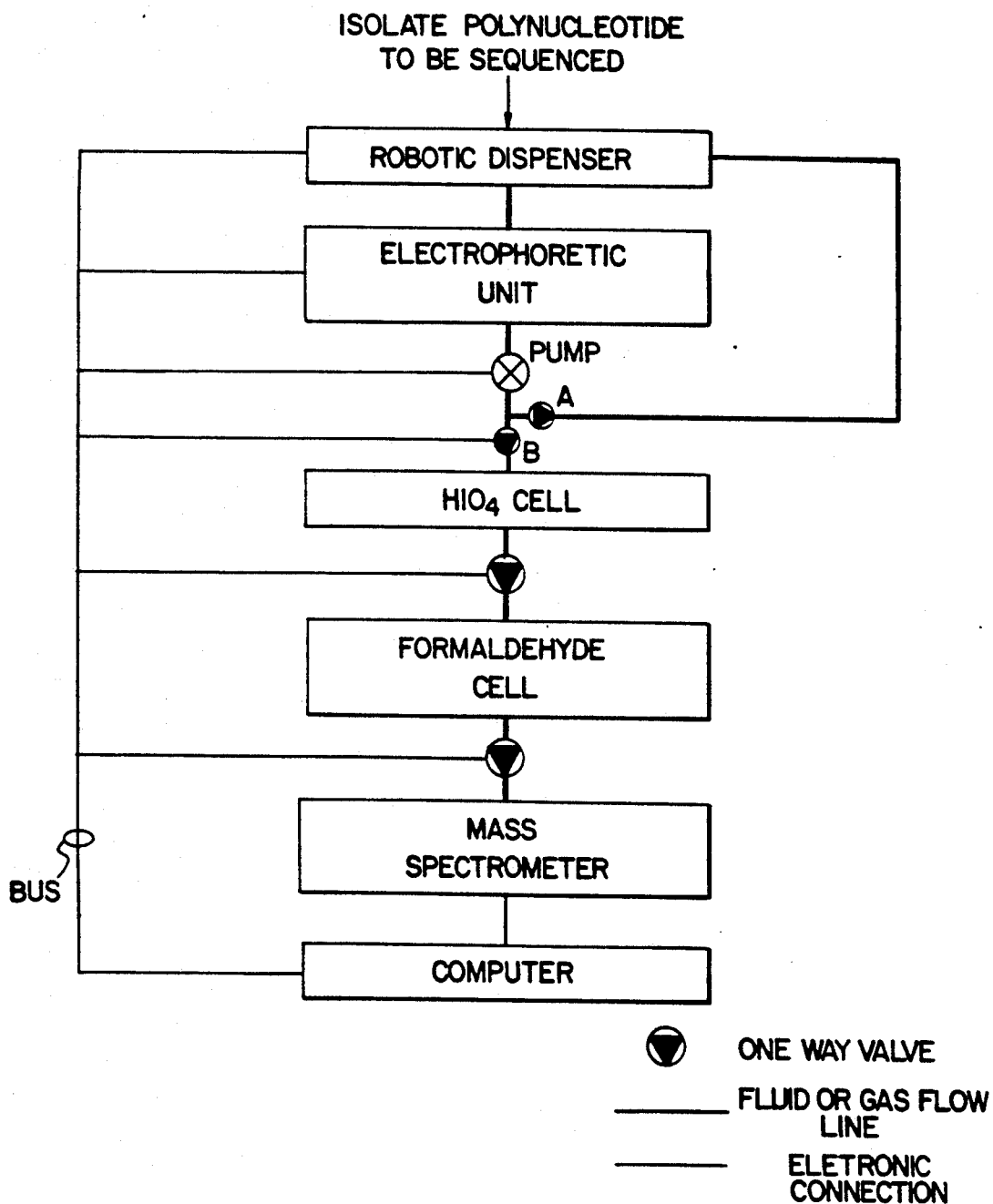
FIG. 8 is an automation scheme which parallels the flow chart of FIG. 2.

The preferred system design of the apparatus to automate the preferred method shown schematically in FIG. 2 which uses the labeling strategy of scheme 2 is shown in FIG. 8. The automation procedure implementing the apparatus of FIG. 8 is as follows. The isolated polynucleotide fragment is transcribed in RNA using for example a first reaction vessel comprising reaction chamber and a computer controlled robotic dispenser comprising means to transfer reagents into and out of the chamber to carry out the reaction. This programmable instrument which performs this and other reactions does so under controlled conditions by dispensing stock solutions of precise volume and by controlling variables such as the temperature and time of reaction. This instrument automatically performs the tasks of pipeting reaction products to or from a reaction mixture.

The product RNA copies are separated electrophoretically using the electrophoretic unit. The electrophoretic bands are electroeluted from the gel and pumped using a fluid pump through the open one way valve B of a selectable two way valve comprising one way valves A and B into a continuous flow period acid oxidation cell. The polynucleotide is hydrolyzed to release pentoses which are oxidized to release formaldehyde. The liberated formaldehyde is collected in the formaldehyde cell and injected into the mass spectrometer. The mass spectroscopic signal is used to monitor the electrophoretic bands. A pure electrophoretic band will produce a mass spectroscopic signal containing peaks from the individual bases at integer ratios, and the absolute intensity as a function of time of each peak of the signal will follow a Gaussian curve. In response to the signal of a pure band, the computer executes the closing of one way valve B and the opening of one way valve A. The peak is collected in the reaction vessel. The isolated RNA fragment is extended in DNA and terminated randomly by performing the replication reaction in the presence of all four possible dideoxynucleotides in a single reaction using the robotic dispenser to perform the reaction. The reaction products are separated on the electrophoretic unit. The electrophoretic bands are electroeluted from the gel and pumped through the open one way valve B and into the continuous flow periodic acid oxidation cell. The liberated formaldehyde is collected in the formaldehyde cell and injected into the mass spectrometer which serves the dual purpose of monitoring the electrophoretic bands and determining the base composition and terminal base identity of the polynucleotide of each band. In response to the signal from each pure band containing a polynucleotide to be 5' randomized, the computer executes the closing of one way valve B and the opening of one way valve A. A portion of the band is collected in the reaction vessel. The isolated hybrid molecule is 5' randomized in a reaction using the robotic dispenser to perform the reaction. The 5' randomized reaction products are separated electrophoretically using the electrophoretic unit. The electrophoretic bands are pumped through the open one way valve B into the continuous flow periodic acid oxidiation cell. The liberated formaldehyde is collected in the formaldehyde cell and injected into the mass spectrometer where the signals give the base compositions and terminal base of each 5' randomized polynucleotide.

All steps of this process such as driving the robotic dispenser, the electrophoretic unit, the valve openings and closings, the pump activation and deactivation, and the formaldehyde sample injection into the mass spectrometer are controlled by the computer. The computer monitors the automation of the preferred method using sensors such as temperature sensors for monitoring the chemical reactions and current and voltage sensors to monitor the electrophoretic unit. The computer stores the data of the mass spectroscopic signals in its memory and processes it to generate the base composition and terminal base identity data of each polynucleotide analyzed. The computer is programmed to identify pure electrophoretic bands and select the RNA band to be extended in DNA and the band or bands to be 5' randomized. The computer uses the data to solve the sequence of the fragment by implementing the matrix method of analysis algorithm.

In another embodiment the system design of the apparatus to automate the preferred method shown schematically in FIG. 2 which uses the labeling strategy of scheme 1 is as that shown in FIG. 8 with the following exceptions: 1) there exists a means to transfer reaction products from the reaction vessel to the periodic acid oxidizing cell directly and 2) there exists a further oxidizing cell which receives formaldehyde gas and oxidizes it to carbon dioxide which is collected by a carbon dioxide cell (which replaces the formaldehyde cell shown in FIG. 8).

The automation procedure implementing this apparatus is the same as for the preferred mode described above except that each polynucleotide fraction which is analyzed to determine the base composition and terminal base identity is first collected in the reaction vessel comprising a reaction chamber and a robotic dispenser and hydrolyzed to 3' nucleotides or nucleosides. The 3' nucleotides or nucleosides are selectively depurinated or depyrimidated and then transferred to the periodic acid acid oxidation cell. The released formaldehyde gas is transferred to a further oxidizing cell where it is oxidized to carbon dioxide which is collected in a carbon dioxide cell and injected into the mass spectrometer. The fraction collections, reactions, transfers, oxidations, and mass spectroscopy are controlled by a programmable computer.

The automation apparatus can be expanded by the addition of reaction vessels (each comprising a reaction chamber and a robotic dispenser), electrophoretic units, oxidation cells, and gas chambers which interface a common mass spectrometer. The signal to noise ratio of a mass signal of a polynucleotide can be improved by acquiring it as an integration by accumulating multiple mass signals from a given polynucleotide. Multiple mass signals of polynucleotide products of the sequencing reactions of multiple fragments can be accumulated with a multichannel analyzer where the mass data for each polynucleotide is stored with its channel as the mass spectrometer is timeshared between the polynucleotides. Reactions to sequence different fragments can be performed in parallel to increase the sequencing rate by a factor of the number of fragments being sequenced simultaneously.

For multiple fragments sequenced in parallel, the sequencing rate is limited by the time required for the common mass spectrometer to obtain a mass spectrum over the entire mass range. Such as mass spectrum can be obtained for subfemtomole amounts of a polynucleotide by using a spectrometer of the design described in *Nature*, Vol 310, pp. 105-111 (1984) and developed by Hunkapillar, et al.

Gas samples are injected into the ion source of the mass spectrometer. Ions derived from the sample are accelerated, separated according to mass/charge ratio by the fixed electric and magnetic fields of the mass spectrometer, and focused onto an integrating detector which uses electro-optical methods to generate and amplify a computer compatible signal representative of the total charge accumulated in each ion beam. The signals generated by several thousand discrete detector elements placed along the ion focal plane are fed into a real-time array processor. The partially processed data are stored on a hard disk for later access by the computer which calculates the base composition and terminal base identity of each sample.

The mass spectrometer simultaneously monitors all ion beams over the possible mass range with sufficient signal to noise ratio to detect the arrival of single ions at the focal plane. An exemplary mass spectrometer of this type is that developed by Hunkapillar et al. described in the above reference and shown schematically in FIG. 9. Its electro-optical ion detector array has 25,000 electron-multipler detector units per centimeter along the focal plane. Ions impinging on one of the detector elements produce an electron pulse which is converted to a photon pulse from a phosphor screen ($10^6$ total complication). By means of fiber optics, an image of the focal plane is obtained on an array of 5,120 photodiodes, corresponding to a mass range of 25-500 atomic mass units with 0.1 AMU discrimination. As the accumulated charge across a capacitor in each photodiode is a measure of the number of ions reaching the corresponding part of the focal plane, the entire mass spectrum can be integrated over times as short as milliseconds with sensitivity limits below femtomoles. For a total scan time of 10 milliseconds, 100 base pairs per second can be sequenced where multiple fragments are sequenced in parallel.

Fourier transform ion cyclotron resonance spectroscopy represents an additional method of simultaneously quantifying the mass range of interest. This instrument is described in the following references: Comisarow, M.G., and Marshall, A.G., *Chem. Phys. Lett.*, 25, (1974) p. 282. Comisarow, M.B., *Adv. Mass Spec.*, 7, (1978) p. 1042.

Industrial Applicability

Sequence information determined via the rapid sequencing method will lead to the development of new pharmaceuticals, diagnostic tools, basic science information, and new cells and organisms which can produce desired chemicals, foods, energy, antibiotics, and therapeutic proteins such as insulin and plasminogen activating factor. Three general procedures in which the ability to rapidly sequence DNA can be used to obtain a desired gene product. They are as follows:

General Procedure I

1) Find a cell that naturally synthesizes the desired product.
2) Isolate the cell and raise it in tissue culture.
3) Irradiate a portion of the stock.
4) Select mutants which are normal except that they no longer produce the active product.
5) Sequence the non-irradiated stock and the mutants.
6) Identify the region of mutation for each mutant.
7) Isolate the identified gene from the nonirradiated stock by using restriction enzymes and electrophoresis where the restriction digest products are predicted from the known sequence.
8) Clone in an appropriate expression system.
9) Harvest the desired protein.

General Procedure II

1) Determine the sequence of a large fragment of DNA known to contain the gene of interest.
2) Produce separate, different digests of the fragment using restriction enzymes which cut the DNA in a predictable fashion based on the elucidated restriction sites in the fragment.
3) Clone each digest separately into a system which is capable of expressing the gene product.
4) Determine whether the gene product is expressed for each separate set of clones by assaying for the same product. The product will not be expressed for those digests which cut in any interior region of the gene.
5) By comparing activity vs. nonactivity to the predicted restriction digest sites, the location of the gene in the fragment can be determined.
6) Isolate the gene from the original fragment by using restriction endonucleases and electrophoresis, where the products of the digest are predicted from the known sequence.
7) Clone the gene in an appropriate expression system.
8) Harvest the desired protein.

General Procedure III

The protein of interest can be obtained in large, pure quantities by elucidating the nucleotide sequence. From the sequence, together with the genetic code which is the sequences of three nucleotides in DNA or RNA that specify amino acids when translated into polypeptide chains, a polypeptide can be synthesized. Then a monoclonal antibody can be made to this polypeptide and the protein of interest can be isolated by affinity chromatography using the monoclonal antibody.

Products

Enzyme systems can be cloned which can be used to synthesize desired organic molecules. This represents a method of chemical synthesis that does not rely on fossil fuels and occurs under conditions of low pressure and temperature. Also, the products are reasonably pure because side reactions are minimal.

The rapid sequencing method could be instrumental in developing organisms that use waste products as carbon sources to produce fuels such as long chain hydrocarbons, methane, and butane.

Further, in the field of food production, genetic information obtained by this sequencing method would be instrumental in developing nitrogen fixation in cereal grains, prolific super hybrids, and plants with herbicide, insecticide, and draught resistance.

Applications in medicine include discovering genes, the products of which are responsible for controlling developmental processes or for revascularization. Cloned products of these genes may be used to regenerate diseased organs. Also, diagnostic markers can be developed such as hybridization probes for genes associated with birth defects or oncogene rearrangements which represent a diagnostic tool for cancer. Furthermore, by establishing the capability to isolate specific gene products, the method would be invaluable in developing gene products such as insulin and plasminogen activating factor which are useful in the treatment of diseases as well as vaccines for the prevention of disease. An Elisa assay for oncogene products that can be used to diagnose cancer can be developed by sequencing the oncogene. From the sequence together with the genetic code, a polypeptide of a portion of the gene can be synthesized. A monoclonal antibody against the polypeptide can be made and this antibody can be used in an assay for the detection of oncogene products in patients suspected of having cancer.

The potential uses in basic science research are enormous. A small sample of the possibilities follows. By using a procedure similar to that described above as General Procedure I, the elucidation of genes responsible for developmental and for cellular processes is made possible. The mutants in these cases would lack the normal developmental or cellular processes. By directly sequencing the DNA fragment of interest, information regarding heritability can be determined as well as inter and intrachromosomal recombination and other genetic events such as translocation and intra and interchromosomal rearrangements. Also, important discoveries may be made such as the discovery of genes containing long terminal repeat sequences which could be possible heritable or nonheritable genes responsible for disease. Also, chromosomal break points responsible for birth defects and cancer as well as translocation events, of oncogenes which are responsible for the development of cancer can be elucidated via this rapid sequencing method. The information in turn will lead to the development of new treatments and pharmaceuticals.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A DNA sequencing apparatus, comprising:
   a) a first reaction vessel comprising a reaction chamber having a first means for transfer of reagents, reactants and reaction products into and out of the chamber;
   b) means for separating individual oligonucelotides and polynucleotides on the basis of length, the separating means having means for receiving reaction products from the first reaction vessel;
c) a second reaction vessel for oxidizing pentose sugars comprising a second reaction chamber having a second means for transferring reactants and reagents into the reaction chamber and gaseous by-products of a reaction out of the reaction chamber;
d) means for selectably transferring separated oligonucelotides and polynucleotides from the separating means alternatively into the first or the second reaction vessel;
e) a third transfer means for transferring the gaseous by-products out of the second reaction vessel;
f) a collection chamber for collecting the gaseous by-products, the collection chamber being in communication with the third transfer means; and
g) means for analyzing the relative abundance of the components of the gaseous by-product by mass, the analyzing means being in communication with a fourth transfer means for transferring gaseous by-products from the collection chamber to the analyzing means.

2. A DNA sequencing apparatus of claim 1, further comprising a programmable control means for controlling;
a) the transfer of reagents into and out of the first and second reaction vessels;
b) the delivery of reaction products from the first reaction vessel to the separating means;
c) the separation of oligonucleotides and polynucleotides by the separating means;
d) the collection of separated oligonucleotides and polynucleotides from the separating means;
e) the delivery of collected, separated oligonucleotides and polynucleotides to the first and second reaction vessels;
f) the collection of gaseous by-product by the collection chamber;
g) the transfer of gaseous by-products to the analyzing means; and
h) the storing and processing the data generated by the analyzing means.

3. A DNA sequencing apparatus of claim 1, wherein said first means for transferring reagents and reactants into the first reaction vessel and transferring reaction products out of the first reaction vessel is a robotic dispenser.

4. A DNA sequencing apparatus of claim 1, wherein the separating means is an agarose or polyacrylamide gel electrophoresis unit.

5. A DNA sequencing apparatus of claim 1, wherein the means for separating includes means for monitoring the separated oligo and polynucleotides.

6. A DNA sequencing apparatus of claim 5, wherein the monitoring means comprises a uv absorption detector, a fluorescence detector or a scintillation detector.

7. A DNA sequencing apparatus of claim 1, wherein the means for selectably transferring comprises a selective two way valve communicating with a fluid pump.

8. A DNA sequencing apparatus of claim 1, wherein the collection chamber for collecting gaseous by-products is a gas cylinder having a piston injector.

9. A DNA sequencing apparatus of claim 1, wherein the analyzing means is a mass spectrometer.

10. A DNA sequencing apparatus of claim 9, wherein the mass spectrometer has means for analyzing the entire mass range of the gaseous by-products simultaneously.

11. A DNA sequencing apparatus of claim 1, wherein the analyzing means is an electro-optical ion detector array mass spectrometer.

12. A DNA sequencing apparatus of claim 2, wherein the programmable control means is a computer.

13. A DNA sequencing apparatus; comprising:
a) a reaction vessel comprising a reaction chamber and a programmable robotic dispensing means for delivering reagents and reactants into the chamber and for transferring reaction products out of the chamber;
b) an electrophoretic unit having means for accepting reaction products from the reaction vessel;
c) a periodic acid oxidation cell having means for transferring reactants and reagents into the cell and gaseous by-products out of the cell;
d) a fluid pump in communication with a selectable two way valve, the electrophoretic unit, the reaction vessel, and the periodic acid oxidation cell;
e) a formaldehyde gas collection cell and piston injector in communication with the periodic acid oxidation cell;
f) a one way valve in communication with the formaldehyde gas collection cell;
g) a mass spectrometer in communication with the one way valve; and a
h) programmable computer for controlling:
 i) the reaction vessel;
 ii) the electrophoretic unit;
 iii) the pump and selectable two way valve;
 iv) the formaldehyde gas collection cell and piston injector;
 v) the one way valve; and
 vi) the mass spectrometer.

* * * * *